US011785948B2

(12) United States Patent
Shin et al.

(10) Patent No.: US 11,785,948 B2
(45) Date of Patent: *Oct. 17, 2023

(54) BACTERIOPHAGE AND COMPOSITION COMPRISING SAME

(71) Applicant: CJ CHEILJEDANG CORPORATION, Seoul (KR)

(72) Inventors: Eun Mi Shin, Seoul (KR); Gi Duk Bae, Seoul (KR); Jae Won Kim, Yongin-si (KR)

(73) Assignee: CJ CHEILJEDANG CORPORATION, Seoul (KR)

(*) Notice: Subject to any disclaimer, the term of this patent is extended or adjusted under 35 U.S.C. 154(b) by 580 days.

This patent is subject to a terminal disclaimer.

(21) Appl. No.: 16/803,710

(22) Filed: Feb. 27, 2020

(65) Prior Publication Data

US 2020/0190483 A1 Jun. 18, 2020

Related U.S. Application Data

(63) Continuation of application No. 15/303,504, filed as application No. PCT/KR2015/002470 on Mar. 13, 2015, now Pat. No. 10,577,590.

(30) Foreign Application Priority Data

Apr. 10, 2014 (KR) .................. 10-2014-0042911

(51) Int. Cl.
| | | |
|---|---|---|
| *A01N 63/40* | (2020.01) | |
| *A23K 20/147* | (2016.01) | |
| *A23K 20/10* | (2016.01) | |
| *A23L 2/52* | (2006.01) | |
| *A61K 35/76* | (2015.01) | |
| *C11D 3/48* | (2006.01) | |
| *C12N 7/00* | (2006.01) | |
| *A23K 20/153* | (2016.01) | |

(52) U.S. Cl.
CPC .............. *A01N 63/40* (2020.01); *A23K 20/10* (2016.05); *A23K 20/147* (2016.05); *A23K 20/153* (2016.05); *A23L 2/52* (2013.01); *A61K 35/76* (2013.01); *C11D 3/48* (2013.01); *C12N 7/00* (2013.01); *A23V 2002/00* (2013.01); *C12N 2795/10121* (2013.01); *C12N 2795/10131* (2013.01); *C12N 2795/10132* (2013.01)

(58) Field of Classification Search
CPC ...... A01N 63/40; A23K 20/10; A23K 20/147; A23L 2/52; A61K 35/76; C12N 7/00; C12N 2795/10121; A23V 2002/00
See application file for complete search history.

(56) References Cited

U.S. PATENT DOCUMENTS

| 7,211,426 B2 | 5/2007 | Bruessow et al. |
|---|---|---|
| 8,021,657 B2 | 9/2011 | Bruessow et al. |
| 10,704,027 B2 * | 7/2020 | Seo .......................... C12N 7/00 |

FOREIGN PATENT DOCUMENTS

| CN | 101724607 A | 6/2010 |
|---|---|---|
| KR | 10-2011-0041670 A | 4/2011 |
| KR | 10-1101376 B1 | 1/2012 |
| KR | 10-1260645 B1 | 5/2013 |
| KR | 10-1381793 A | 4/2014 |
| KR | 10-1381795 B1 | 4/2014 |
| KR | 10-1381797 B1 | 4/2014 |
| KR | 10-1381798 B1 | 4/2014 |
| WO | 2013/073843 A1 | 5/2013 |
| WO | 2013/157813 A1 | 10/2013 |

OTHER PUBLICATIONS

Murthy et al., MX2007005279A (Year: 2008), 15 pages of PDF.*
Bihannic et al., "Identification and detection of three new F17 fimbrial variants in *Escherichia coli* strains isolated from cattle", Veterinary Research, vol. 45, No. 76—12 pages (2014).
Nguyen et al., "Virulence factors in *Escherichia coli* isolated from calves with diarrhea in Vietnam", Journal of Veterinary Science, vol. 12, No. 2—6 pages (2011).
Nagy et al., "Enterotoxigenic *Escherichia coli* (ETEC) in farm animals", Veterinary Research, BioMed Central, vol. 30—27 pages (1990).
Zhang, "Animal Biodiversity: An outline of higher-level classification and survey of taxonomic richness", Zootaxa, vol. 3148—238 pages (Dec. 23, 2011).
Extended European Search Report in corresponding European Patent Application No. 15776278.2—9 pages (dated Nov. 10, 2017).
Endersen et al., "Phage Therapy in the Food Industry", Annual Review of Food Science and Technology, vol. 5, No. 1—25 pages (2014).
Kim et al., "Evaluation of bacteriophages for prevention and treatment of diarrhea due to experimental enterotoxigenic *Escherichia coli* K88 infection of weaned piglets", Korean J Vet Serv., vol. 34, Issue 4—12 pages (2011).
Bourdin et al., "Coverage of diarrhoea-associated *Escherichia coli* isolates from different origins with two types of phage cocktails", Microbial Biotechnology, vol. 7, No. 2—12 pages (2014).
Jamalludeen et al., "Evaluation of bacteriophages for prevention and treatment of diarrhea due to experimental ~nterotoxigenic *Escherichia coli* O149 infection of pigs", Veterinary Microbiology, vol. 136—7 pages (2009).

(Continued)

*Primary Examiner* — Kade Ariani

(74) *Attorney, Agent, or Firm* — Knobbe, Martens, Olson & Bear, LLP

(57) ABSTRACT

The present disclosure relates to bacteriophage ΦCJ28 (KCCM11466P) and a composition containing the same as an active ingredient. Further, the present disclosure relates to a method for preventing and/or treating infective diseases caused by enterotoxic *Escherichia coli* (ETEC) of animals excluding humans by using the composition. A bacteriophage ΦCJ28 (KCCM11466P) has a specific ability to kill enterotoxigenic *Escherichia coli*.

5 Claims, 3 Drawing Sheets

Specification includes a Sequence Listing.

(56) References Cited

OTHER PUBLICATIONS

'Yan et al., "Effect of Bacteriophage Supplementation on the Growth Performance, Nutrient Digestibility, Blood 6 :;haracteristics, and Fecal Microbial Shedding in Growing Pigs", Asian-Aust. J. Anim. Sci., vol. 25, No. 10—6 pages (Oct. 2012).
Brussow, "Phage therapy: the *Escherichia coli* experience", Microbiology, vol. 151—8 pages (2005).
Loc-Carrillo et al., "Pros and cons of phage therapy", Bacteriophage, vol. 1, No. 2—4 pages (2011).
Notice of Allowance of corresponding Korean Patent Application No. 10-2014-0042911—2 pages (dated Jan. 21, 2006).
Office Action of corresponding Japanese Patent Application No. 2016-561675—4 pages (dated Jul. 18, 2017).
Cha et al., "Effect of Bacteriophage in Enterotoxigenic *Escherichia coli* {ETEC} Infected Pigs", Journal of Veterinary Medical Science, vol. 74, Issue 8—3 pages (Jul. 18, 2012).
Dini et al., "Isolation and Selection of Coliphages as Potential Biocontrol Agents of Enterohemorrhagic and Shiga Toxin-producing *E. coli* {EHEC and STEC) in Cattle", Journal of Applied Microbiology, vol. 109, Issue 3—16 pages (2010).
Jamalludeen et al., "Isolation and Characterization of Nine Bacteriophages that lyse O149 Enterotoxigenic *Escherichia coli*," Veterinary Microbiology,vol. 124—11 pages (Jul. 18, 2007).
NCBI, GenBank Accession No. HQ829472.1,—93 pages (Sep. 7, 2011).
International Search Report of PCT/KR2015/002470 and its English translation—4 pages (dated Jun. 18, 2015).
Ayoola, "Influence of the Animal Feed Binders on Optimal Nutritional and Physical Qualities of the Animal Feed Pellets and Feed Production Capacity—A Literature Review", Dept. of Animal and Aquacultural Sciences, Norwegian University of Life Science (Submission Date: Aug. 17, 2020).

* cited by examiner

[Fig. 1]
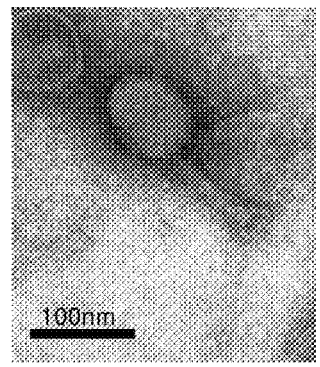
[Fig. 2]
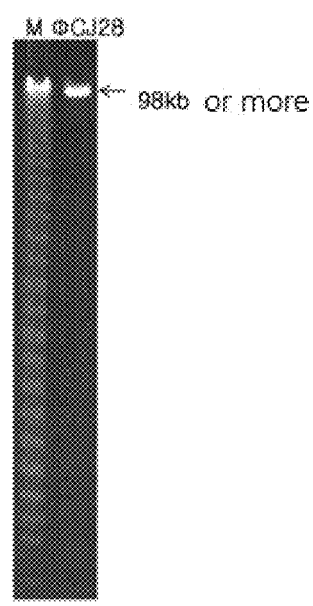

[Fig. 3]
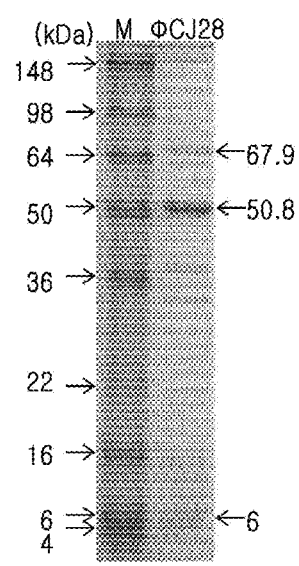

[Fig. 4]
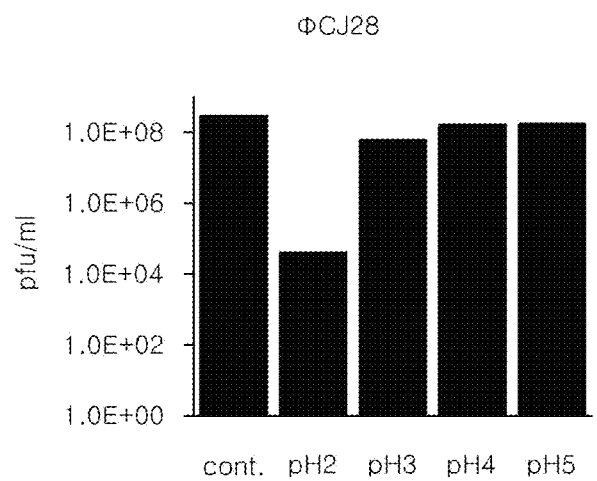
[Fig. 5]
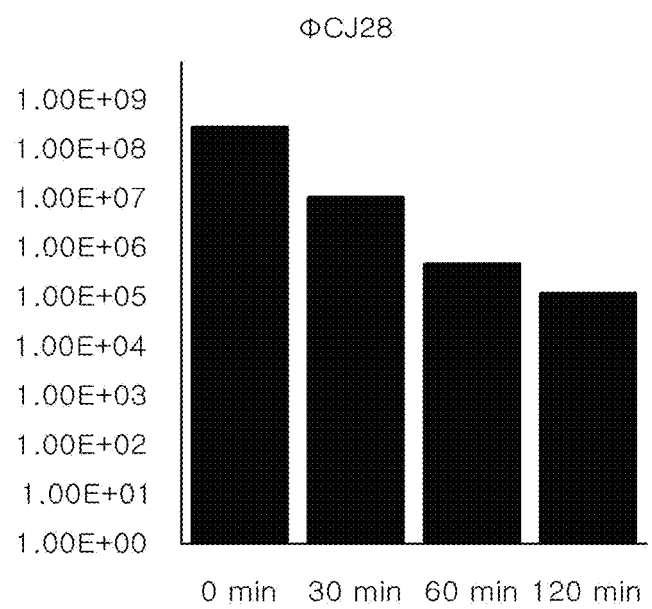

SEQUENCE LISTING

<160> NUMBER OF SEQ ID NOS: 1

<210> SEQ ID NO 1
<211> LENGTH: 171499
<212> TYPE: DNA
<213> ORGANISM: Novel Bacteriophage CJ28

<400> SEQUENCE: 1

-continued

```
aaatacgttg ggtccaaccc attgaatatg caaccattat atcactcatt tcaataagcg    60
ttttggctgc ttcaaaagtc attacattag aggtttccgc tgtttgggtg aatttaccgt   120
ccatggagtg gatataatgg tcataatgaa tctgggtatc ttgctcgttt aaatcaaact   180
tgacaaagca acgtttttcc tcggacaatc cacgaacacg gttagtaata gtatcccaat   240
attcatcgat gtaaatacct tcaagagaaa aagcttcatg ctcgttaaga ttagacttga   300
caatttcaat aatatctgaa ggcttaagac ctgattcaag aagctcttgg attttagcca   360
atttctcagc attgccttga gggtccattt tatcaaattt tttagcttct tcaaaatgtt   420
gctcagggcg agcactcaca cctttaccaa agtagaaagg ttttttgttt tcatctacta   480
aacgatatac ctgataaatt gtttcttgat tgtaagccat tttaaatctc ctttagttga   540
taggtctata gtatcatgcc tacaggagat gtaaactgat tttataaata ttaatttaac   600
aggaggataa catgggcagt attttttacc aaatctggaa attggccgaa agaaagaca    660 agaaaatgat gttaggtttt cttgcactag atgtattcct ttggaatctt ctggtagtcc   720
ctgtagccgc tagtcaaggt gtaattttac cagcggttac aatggagcac gtgttaagca   780
tagttgggtt ctttagcgga attcctgcct aaatcttgga atattttgaa agtctcattt   840
ttgccattaa accttgggct atattagctt tcatatatgc cagtacatca tttatatcgg   900
ctttatcttt cataaccata tcatttatat ctttagaagg ccatgggcc ttgtcccaga    960 atagaaccct ttcgccagca tcaactaatc gttgcatacg cttaattgtg tcaggatggc  1020
ggggttcatt gtccattacc caggcacgag tttctttaca tggaactata gccaagtcca  1080
atgacccacc agtaattgct attgcattcg gtacgaataa tgaatcgata ggaccttcca  1140
ttacccacac caactgacgt tcgtcaactg tatccattcc atatatttt gtagcttggt   1200 catgagcttt tattgtaata tatttttgtg gagcgtcttt acgtaaggct cgaccctgaa  1260
aactttcaat ttgtttattc ttattgaaaa ttggaataac caaacgaggc tcaggcattt  1320
ctttagaata ggtccctgga ttgacagagt tcaccaatgc aggccattct ttagtaaacc  1380
acagccggtt ccatttgttt tcaggaatgc aacgtaacgt cacatatttt ataataggat  1440
ggtccttcgg cattctatct aatcgttcac agaaattaag cttttcgatg acaggcatct  1500
tagctttaat ttttcagat atctccacct taggtgcagc ttgtctcccg aacgattgct   1560
ctttatgttt ctcaagaata tattcacgat ataaatcagg ctcatattcg tatagatact  1620
tcttaattcc tgctgaataa tcacagttaa aacagtgcag cataatagag ccgtcattgg  1680
caggataggc ccaaaaacga gctttgttct catcttttg ggagtcaccg catacacgac   1740
aacggcagtt taatttaaaa tcactaccag ttacttgtct gaatttaggt tggtaattca  1800
aggcacgtac agcaaattct ttatcgacat atgacattat ttttccttgg gccctaaatt  1860
aatagagcca ttatatcatt cgttttcgga ttttttcttta cgcttttag atgggatttg   1920 ttcaggcccc ttgttgacga ccgcgcctga ggtagtccg gaggcaatag cagtaggatt   1980
accacctgca tcgcctgcga ccatatcttc gttcataact tctttaaaag atttcatagg  2040
ctcctggcct tatttatatt acgaaaatag ctttatcacc atttgcatca gtgacttcat  2100
aggtatcttc gtggtaaagt ggaataatcc aagtcgcacc atcaccagca ataatatgga  2160
tagcttcttg gtcttttgat acgatttcat attcttcgaa taattcgaat acagaaatct  2220
tagagcccgt acacattgca ctcatattgt tcccttcttt taatcagttg gcgatgagcc  2280
tttttaagtt tacgaagctg acgtttagtt ggccgtgcaa cataagcttg agtagttact  2340
```

-continued

```
cgtccaaaaa caccgtactt aggtgaagga gaatcgataa agacttccca ctgacaagag    2400
taactataca cggctttaga gaattgagtt aagacaaaca tattaacctc gattcataaa    2460
agcattaaaa atttggtcat caattgaata aaccggggct tccagaattt tcaacagact    2520
gtttttgata tacttgctag ggatatccat attaacgcca tcattcaatt cgttgtccgg    2580
gaggatatct ttaaattcga atccatcaaa ctcaaccttg tcaggaatac cttcagcgaa    2640
aaaataaacc aattggtgca ttgtattgca tgaaaataat ttagacctca ccgcaataag    2700
ttcttgccaa tggtttaatt ctctgttaag aagtttatga gccattgtaa ttcgatcatc    2760
actatcaaca agaaaataac ccaggtattg gtggtcgtcg ctccaaaaca tcctgtatgc    2820
ttgtgcattt ggattttac aacgaagctt tttaataact aaatttctgt taatcttatt     2880
cacctgtcac ctcttaacg atattttgt tatcgaaatt ggcatcacaa tacaaaacat      2940
agttatattg cataacacca cctgaagcta attggtctga cacttcttta gccatatcag    3000
ggcggtcacg tttagtgatg ttcatgatat cagcataaat ctgatgttca accgattctt    3060
ggtctgcagt catagaccat tcacaaaggt cttatccaa tccggccgtt accggagccg     3120
tgccacatga tgctactgta aggattgctg cgattaataa cttttcatt tttaactcct     3180 cgttagttga taggtccata gtatcactac catagaccgt tgtaaacttt attttaacga    3240
atcttctaaa taaattttac ggaatttacg ttttgtctgg cgaatctgac gcttagtagg    3300
cttcacagga aattcgaaga actctacgta ttcttgttca taatcattgt gaccgactga    3360
aagaactagt tcccagttgc ttacagtacg ttggataaac atattatgct taccaaaaga    3420
tttgttccaa aaagaactgg gagttggttt cattagtacg atattcattt attcctcgcc    3480
ttcatgttta tgggcaattt cttcgaattc gttgtcacag tctatacagg ttgcattgtc    3540
ccaagcatca aataccgctt ggtcttcgcg gaccgaacaa ccacatacta cacactcaac    3600
ttcttccatt tagatttcct caatacgggc atcatgttca taaacttcta cgtcgtcgac    3660
atacgcctta accaaaatac tattgacttc agcgaattgg gtagtcaccc acacgatatc    3720
gttttcacgc actgaagctt ctttggtagc ggtatcgccg ttggtgaaat ggccgacaaa    3780 ttttactttta attgattcag acatttagat ttcctcacag aaggcccatt cagcatgata   3840
aaccgtagcg cctttagtat catttaaaca aatcacatct accggagcaa ttacacgata    3900
aagacgaggt tctcctccca ctgaacgagc tgcacgtcca gcataaatct tagccaaacc    3960
gatatcttca gtaaagaaca cacgatttag gttttttctta cgaccggttt cagacaaaac   4020 tcctgttttcc tcaggaggac aaagcatatt accgatatta gcaacactac aacttccatg   4080
ataatacact ttatattctg ctttacagtc gatggttttc attttgttct ccaagttgat    4140
aggtctatag tatcacgcct acaggagatg taaaccctta aaaacaaaaa aggagccgaa    4200
gctccttaaa atttgataga tgctgctaaa tcgtccaaat cacttctatt aacacgcgtc    4260
tgtcgattga cctcggcctg tcgattcatc tcacctgtag cctcacgaac agtgttcact    4320
ggacctggat tggaatcgtc ttcaacttcg taccaacgtt gatttccttt cttaacacca    4380
atcttaaatt tgttgtagta gctcttatcg ccataacgag atttaagctg cttaaccatc    4440 tgcatacccca tctgagcaaa ctcttctgtc tcgaccacac ctaacatgaa gtctgcagta   4500
tgtgcaatac caaaggattc agcaatatca gccatatcga tttcggctgc aacgttcgca    4560
ccacgagtag tctgggctgc tgtccacagc aataatttct tctctactgc aagcccacgt    4620
agttcttcgg cgaccatctt aatcaatccg taactgtttt cagagaaaac tttcgtacgg    4680
gatgatgcac agatagccaa gtagtcaacg ataaccacct gagggacaaa gttttgtttg    4740
```

```
agcttgtatt cgtttaataa tgcacggaat gtatcggcat tcgcaccgcc agtaggatac    4800
tgtttaatct ttaaacgacc taaggtagca gttgaacgcc atttatccat cttagcttta    4860
tattcaggcc aagagacgtg accatcatca atatcgtcta gtgatacatc cagaaggttg    4920
gcgtcgatac gcttagcaca tacttcctct gccatctcca tggagatata agaacatcg    4980 tatccagatt gaagataatc agcagccaat gaacaaagac caagagactt acctacgttt    5040
gttcctgcca acaatacgtt ttcagtacca aactcggcgc cgcccttggt aatcttattc    5100
agaatattaa gacggaatgg aaccttacgt gctttatcgg ataacttttt gaatcgttct    5160
tcatagtcat ccatccagtc atgacctaat tcagaatcga acaaatcga taatgcatca    5220 cgcatgatat ccggaatggc accgatacct ggaagttttc tattttgttg ctcaaccgga    5280
aggtcggcat tagtttggat ttcaatgatt tttgaagttg cattatacat cgctgctttc    5340
tgaacgtatt tctccgtctc tttaaccaac cattcttggt cttcaggtcc ggcattcagt    5400
gaacttaaaa gctctttagc gccttggtgt tcaacttctg aaagcgtact gttatctaac    5460
gcaatactca atgcattctt agaaggcact gcattatatt cattgacgtg ttttttaatt    5520
tctttgaaaa gggtctttgc aggaccctgg tcaaaataag aatcattcat ataaggccag    5580
accttagtga aataatcact attgcctagc agttgagcca aaatagtttc taccacttcc    5640
accacctctt agatttaatt ttatccagtt cttcttgtat ttgcattgta acacattttt    5700
ctacatgaag cgctagctct tcttttcggt cttcggaagg tgttccgaaa tcaaccgaca    5760
cttttccatc tttctcaata acaatattca tcacataaac gatgtgagca gtgccatcgg    5820
gtaaagtaag cataatttcc tgcttaaccg aacccattga cttacggatt atatctaatg    5880
atttctcata ataacgaggg tcactaggac cctcttcggt atctttaaca aaattatcta    5940
aatcagataa atcagtcatg gtcactcaca aaattcatat tttctaaatc gttttcgata    6000
tcagcagcgc tttgggtatt tccacctaat ttaacagcaa cgttcttaga gacacgagag    6060
ttaataaggt cgttcactgc atcgtcaact tctttaatag aattaattgc accgagctta    6120
tacttattct cgattgcttc acggaacggg gcatgtttaa acagcggtcc ccagaactca    6180
acacaatcgg tagctttagc acgccatgct ttttcttctt gaaccatttc gcctgtggtt    6240
tcgtcaagga atgcacgatt ataccaacca gctttaggtt tcacgacaaa gccgatatca    6300
gtagccattt caagcaatcc actgaatggg tcgataccgc cttcaaagtt aacggtgata    6360
gggaacgttg atttctcttt aaccgtacga gatttctcag ccttcagtgt aaagtcataa    6420
cctgtgagct cggtaccatc tttaacctga cgttagaga taaagaacac ggtagaagca    6480
gagtacagaa taccagtacc accacccata atctctttag gatacattcc accaatttcc    6540
atagccgtat ggttgattgc tacacaaggg atatccttga tggtcagata aggcgttacg    6600
atacggaaca gagatttcag tgacttagca cgggtcatat cacctacaac tttctcgttc    6660
aaagcatctt cggtttcttt cttagaagcg gtgttaccaa tggagtcgat aaagataata    6720 acctttttcgc cacgagtaat ttcttctaac tggttggtca tatcaacttt aagctgttcg    6780
actgactgga ttggtgtatg aaccacacgt tccaaatcaa cacccatcga acggaaataa    6840
gattctgaag caccaaactc agagtcatag aacaaacaaa ttgcgtctgg atatttcttc    6900
atatacgccg caaccatggt aagtccgaac aacgttttaa agtgtttaga tggagcagca    6960
aagattgtca aacctgattg taagcctgca ttcaacgcac cacctaatgc aatattcagc    7020
atagggatac gagtaggaac ttcgtcacga ccattaaaca atttagattt ggtcaggtcg    7080
```

-continued

```
gcagtcattt tagaagtaga agctttaatc aaacgggatt ttaaatcgga cattatattt    7140
ttccataggc accattatat tttactcacg ttttaagata gggtaattat atcacttcac    7200
atttacagcg ttaaaggacc acgtcctcat aacttggcat ttcgtgctca gaatggatat    7260
gggcaccgaa ataaatgaat tcagccagac caggatggaa tactaaaccg ggattctcat    7320
gataaatgat atgaggtctt gatttcagaa tctgataata ttcaacctta ctcggtttga    7380
atttaataat ctctacatca ggacgatagt tttcgcgctt aaatgaatca ttcgggtcgg    7440
taatataaag tcgagcacct tcagccgcag cttggtctac aactctttcg aattgataac    7500
atttatctga gatacggaac ggatggaaaa taccatcaat tttaataggc gctagacctt    7560
cagagtaacg ctcaattacc gccggattaa ttaccttttg gtctacaaaa atcttatcag    7620
aggacgcacc tcgtgacacc aggacgtctt tctggcattg attcaggact gtagtataaa    7680
tcgaacgttc aactgaagac acgtcggtat caatgaactc atcgatgtaa taacgaggaa    7740
cttcagggtc cattgtaatg ttaaagttga attgtacagt ctgagtgcca tcataacctg    7800
tgatatcggt tactaatcct gagcagtcat agtattcgat taacgaatca acaacgaact    7860
cattttcaga ccaaaaatgt ttacgggttt cataagcatt ttctttatac caaagtggta    7920
cgaaattcag ttcagggaac aattcaatac attctttgat atcgctcgaa tttctaggat    7980
aagccagata atcacctggg cgagcacggt ttaaatggag ttgaaaatta ccgtccttaa    8040
ggacggcata ttcacctgtt tcgtaactac gcatactgaa ataggaacg ataaacagac     8100
tcatttcagg aatcctcgaa cgtagtcaaa atcacgttca aatacatgtg cactaaccat    8160
agtatgggaa tacgtaccca gaccaacacc acactgttca gcaataaagg ccatcagttt    8220
accctgcaga tagaaatcca gctgcataac gatagcacag ttctgtgaac gcatatgagt    8280
gtgtgcatac agacgtccat cacgaatata atatgttacc gaatcggtac atggatattc    8340
tagggattcg tcagaatcaa ggagggcttg gtcttgttct tggagaattt ggaacacaac    8400
tcgtctcgag ttaggctttt ctttaagctc tttaagtagg gctgggagtt gggccacaat    8460
tcgaggtcca tagaaagtgt tgaagtttgc aggcaatacg tcacttttcg gcttatcaat    8520
gaacttagca acattaggat attccttaaa tgcttcggcg gcgtcagtac caccagaaat    8580
cataaatttc cagaaagatt cggcataatc atagttgata cgattaatac gagggtcggt    8640
gaatttatag gtgcttgcat ccagtacttc taccgaagca gaaccaattt cataacaacg    8700
gccgatacga gaatcaactg caaactgtgg agcttccagg atttcttcgt tcatttgctt    8760
aaacgcgttt tcaaaactaa cagcggtaat gtgtttcatt tattcacctt attttcaata    8820
tattcattca gacgttttaa ttctaccata tcgacgttaa gcaagttatt atggccgtcg    8880
tgatttaaga ttttaaacac gttttcaaaa catgtttcat attgccggat agttagattg    8940
aactcatctt tggttaattt aataaggtcg tcttcgaagt cttcatctaa tgggttacgg    9000
gttaaaataa cctcaataat attgaattca gatttaaacc ctttccaatc ttccagttct    9060
acataagggt ccatttcacc acgaaggaat ccagagtaaa caatattact aggatatcca    9120
cggtctaaga tgtagacaaa attagggtct aaaaacttat ataaggtttc gactaaagcc    9180
ttatcgttat cagtccctaa tgaaatgcat ttgccattaa tcttttttagg aaaatcaata    9240
agacgatatt tcttatcaga taaaagtgat tcaattaaag tagacttccc ggaattatcc    9300
gggccgtcga taacaattat ttttggtttc acgatgata tgccttatag gtttcaagag     9360
ttccttcacg aaccatttct ttaaagtggt caggtcggat tgctcggtca tcgatgataa    9420
aagtataact cggcttatgt gtaagcagat tatgatattt caatccaatc ttttcaaggt    9480
```

```
tcttaaccaa tgcaggaact acttcaacca agattcgacc aggtccacat gaagtcatac    9540
cacgagcagt gaacaacgta atctcataac cttcatcata aagcttatta atcatggaca    9600
ccatttcggt gtctggttta aagttttcat aatcacggtc gtggttccaa accgtgattg    9660
tattatcgat gtcaaaacat aaatgggact tattttctac tcgatgcgac attaaatttt    9720
cttccattgt ttgtggagtt cagtagaacc cgtaggttta tattttacac cagtttctcg    9780
gtcaagcaaa acccacttat caggacaacg agtaataatt tgagccgtaa tagggtcgcg    9840
aacttcatca acgaattcac ctgtgataag cttacgctta cgaggatgcc gcttcagcag    9900
cacactcagt tgatataaac cattgtaata agcacccaga gctttcagag ggttattttt    9960
aaagtaacct gccaatgcca tccagataac agcaatccag agcttgtgct taaatgtaca   10020
cattggaata tcatctaaag gcataacctt ttcaatatca acgaatacac gagttccgtt   10080
acgagttaag ccgccccata gagggtcaga gttaaatttg tcataaccgt cgatagaata   10140
aagcacctta gcttcgtcat aaatcgcagg gcctttagaa ctattaccaa aataaccacg   10200
tgggtcgatg attttaatat caccttcgtc cgacaacata atattactgt agtgcgggtc   10260
accatgaata agttggtacg gttctttatg ttcagacaga atttctagtg catgacgaag   10320 aagttttttct gggtcgccta ccttaaagtc attgacatgg gtaatgccct gtggagcaaa   10380
gccttcaatc aatccggcaa tagaagcatt acgaatcagg accttgtcca atacttcttt   10440
cttaacatca gaataccatt gctcatcgga tggattatcg atagttccac cgaatgaacg   10500
caatgcacta acgaccttat aaaccatgag gactttagtt tctttagaca taaaccggta   10560
ggcatctgcc atggtgcgac caaagatacg ttccatttta atgaattcac ccggagcaaa   10620
gtctacaatg ctcggaacga attcagaatc aatagaattg taccaattga tttctttaga   10680
ttggatttct ttacctaatt cgttggtagg tactttaatg gccagattct cagtgaactc   10740
taatttatta aattcacggt taatttcaga atcttcatgg gccttagcca gtttcaattt   10800
gtcaccgaca tcaactacaa agtccagctt acgttctgtc aaatggacca ttgaatccag   10860
gttgtcggca aggtcttcgc cataatacag actgttaaaa cctgtccaat tggctacttg   10920
atacaaacca actacaccac cgccagtacc aatttcacgc aagtacggtt cttcaaatgt   10980
aaaacgacag tcagtcccgt aggtataaca gtagtcatta tcccactcaa ctttatgacc   11040
ctcaggaatg atgtcacacc agttaaacag gacattgtgc ccgatgatat cttcagcaat   11100
gcaatcgata gcatgagctg aaccattggc cacatctacg ttacgaatag tgaatttagg   11160
cttatcacta ttaatcatgt taatggattt aatatagcct ttaacgaggt cgttaaattt   11220
gctgtgaata accagaataa tttcatctga ttggttacta tacaaatcat acaaatgttt   11280
taatactgta tgctgtttgt agttaaccaa taccttaggg atttcgttag taattggata   11340
caaccgtgag ccaagacccg cgcctaaaat aacaaccttt ttcattatct gttcctcaag   11400
tgaatgtagg tacattatac actatttta ataaattggt attgcttaaa tcttatcttt   11460
accgatttcg atgcactgtt ctattgctgc tggcactttg gtcttgagct tattgatttg   11520
tttcttataa tcacgggctt tatcgaaact ctcggtttcg agcatttcgt aataacgagc   11580
ctcatggata gaaatctgta gattgatatg atttacgcac atcgcataca gtttctgttt   11640
tttgtacaaa tcgtcttgac gcttcatttc tgcctggtgt ttggctagta ccgcttcacg   11700
cttggactct tgttcgcgtt ggaattcgat ttcccttttga gcatattttg cacagttatt   11760
accacattga ttattagctc gggtgtacac aagtccagaa cctgcacgga atttcatttc   11820
```

```
gccatcgaat tgtttctgtt cagctgcgat acgagcttta ccaacttcat cggccgaaac   11880
tgcatcacca tattggactg cgcaacctga taggagcata ctcattgcga taattaactt   11940
tttcataata tcctcaatta aaacagttat acttaatttg tgctataaga ataatccatc   12000
cgatgattag tgtcggaatc attggtgaaa ttgccactgc ccaataaacg gtaaaggcgg   12060
tcattataag aaataaaata attattttca ttgcttaaca ataatgattt gcgcgtttga   12120
tttacgttca gcgacgatag cccatattaa agccactacc caaccaatca tcgtccaacc   12180
caacaggaga ttaaggaaga aaattcctac attactacga gtgcctcgca gaagagctaa   12240
aatccatggt aaaagtaac cgatgaacat aatagccaga gaaccaaatc ctaaaacacc    12300
agcactaacg attaaagctt ccattgtaat ttcctcatgt agttgatagg aaggatacta   12360
ccacgttcca tgtggtatgt aaacacttaa aagtcgaaca tatcaaataa tgttgctttt   12420
ttctcgtagt cgattttagc agattcagta aaaccggtca gaggcttgat aaaggtcttt   12480
tggaaaagta cgttgtagtc catccaacgg aggacttggt cacgaatctg aaccggaagt   12540
tcaatacctg atggccatgc catacaagct tcaccaaacg ggttgccttc tttaagcggc   12600
agtacatata cctttcacc atcaacgata cgaggcatag tcaaatcacc tgcagaagca    12660
cgcatgtaag ctaagcaacc tttgatgtgg tacgggcatt tagaaccagg gaatccacct   12720
tcattatatt tctcgatgtt gttagcactg gatactgcag caatgcttac atagttcagt   12780
tcgttaaatt cctattaaa ctgtttgaaa tattcttgca aagaggcctc gccttcttga    12840
agcatacgac ggatacattc cttcagagct ttctgaactg ctttaggtgt acttgatttc   12900 tgagttttcca gacccatgat tttcaagtgt ggttcggcat aacgagtacc ttccatgtcc   12960
caaacgttca gtgcataacg tttcttgcct gtccagaatc cgccaagacc tttagaacca   13020
agtggaggac cagcgatagc ttctcggtcc atgaacatca agtgctgttt gttgttcata   13080
tactcgcaca tctcacggaa gcctgcatca atagccggtt ccatacgttc acgtgcaaat   13140
ttatctaaga agtcaaccca atggttagta tcacggaatt tatcttcgcc tactttattg   13200
atgattgcat ccgccttaac ataaatggag tcagtatcgc catagagcac gaacttctga   13260
ttttcagttt tacacacact attcagatat tcgttaacct tacgttcaat ccattggagg   13320
gccatttgac caaacaatgt gattgcagtt gcgttcctga ggtcgtagta gcggaaccat   13380
acgttaccaa gtgcaccata aagggagttg ataagcaact tacggttaat ctgagcagtg   13440
ttacctgcaa cttcagtgag ctcggctttc ttcaacattt ctcttaaaga aggcgctgac   13500
agtgctttaa tctgggcttt gatttcgtca gagaagtcaa aacgataatc gatatccagt   13560
gggctatcaa ctgagagatt aggattttcc aatgcttctt taattaactc accattacgt   13620
tgagctgcaa gcatgtaacc tttatgttct ttacgctgca agaataccttt ggtgatttct   13680 gtcggaatca caccttcacg gtctttataa tacatcatgc cgttaggaga gcaactgtag   13740
acatcgctag gacgctgagc agttccggca atatattcat gtatcggtgc gttagcgaat   13800
gtgcctgcga tggtctctgg gcttatattc acttgtcgaa tgatactcgg gtacagagat   13860
gtaaggtcga aactcattac atatttgtaa gcgttaggaa taggttcctt aacgaaagca   13920
ccaggataag gttggaccac gtgtgaacga gcttgtggaa tgaccttgcc ttgttctta    13980 aggctattaa agataatagc atcccaagtc ttaattggac tgaacactga ctgaatctgc   14040
atcttagcat aataacccat gtccaaactc agaagaatga actggcgttt catatcaatc   14100
tgcactacac gatatcgtc gataatgtta taggaaatat atcgttggtg gttcgtctca    14160
cgtaacttgg agattggacc atcatatttc aacttaccta ctttcaattc atattcagaa   14220
```

```
acataatcca aagaataaga aggctggttg gtaaagctga attttttata caggtcgata   14280
taatccagaa cagagatacc gaacaatgta ataatttcac gagcaccgta catgttctcg   14340
ataactttaa cacgggtctt acgatgcggg cttaatcgct tagcagtatt ctcaccaaac   14400 agattttca gacggttata aacgtatggt acgtcaaacg actcaacgtt ccatccagtc   14460
aaaatcacag gagttttctg ttgccagaaa ttcaaatact caagcatcat ttcttcttcg   14520
gaattaaacg gaagataaac gattttgtca atgattctt gtggaacttc gtcaccacct   14580
tcttcttgga gtttctcagc gattttaatc gaccactctt caacagtacc ataaggcgaa   14640
actaaaaggt cgaatacata gaattatcg tcaatcgagt cgtagtgggt aatggcatcg   14700
ataggatgtt tagcctgagc tggttcaggg aatccatcag gagatgttac ctcgatgtcg   14760
aagttagcaa tacgaatctt agaagaatca tatctgattt ctttacgata ggtatcagac   14820
aaataggcca atttatagtc gtccatacct agggcttcga ggcccatatc gtccatacgt   14880
ttcatccatt gggatgcatc acgcatagag tcgaattctt tcttaacaca acctttacca   14940
tagatatcaa tgtattttac ggcttgctct gggttagcat gcataaacat tgtaggcttg   15000
taaggaactt cacgactacg ttcgttacca tttttatcga tgtaacgttc gagaatatta   15060
tcaccgattt gttcgactgt caaatagaat tcttgcattt catttccttt atagacgagt   15120
gattgtcttt tgtttgttga tgaatcatta tactccaaaa agggaccgaa gtcccctttgc   15180 ttaaatttct attgtaaaac gtttaatgga tggattgcca tattcgtctt tagttctaat   15240
catagcctgg aaaactcgtt gacctggatg tagtaactta tggaggtcct tttgaaattc   15300
tatttggagc tcttcggaaa ggtcaaaaac agtttgagtt ggggaaagtc cgtatacctc   15360
tttaaggcgt tcacacgttt caatttcaag aatcatatta attaccaatg gtgtacttgg   15420
acagtagttc ccagtcattt ttctgcttaa aggaaatgac acggaaatta ttagtgattt   15480
cgaacagctc agagtcgtct acgatatcaa tcagtcccca ctccttaaga agctgggcaa   15540
tcgaatcacg acgttggtag tcttcaccat cgatatcaac ttgacggcca tccatacgca   15600
acatctcttt aaagtggacg atataatata gcccttgttt ttgcagaatg tggcaggatt   15660
gatatagttt ctttctttta ttattagcga tacccatacg agttagggtc tctttcactt   15720
tcaagaagtc ttcaggttgt ttcagagtaa tttcaatcat tttaatttac cattccaatg   15780
cttttctttt caagtctttt tgttctttaa catttttagt tacggatttc aggaactcgt   15840
ccgtaaccaa ccctttcatc ttcttaagca ccgccggaag atggcctta attttataag   15900 tctcgagata acgataagcg tcatcattat taattgaatg gtatttcatc aataaacgag   15960
taataaaaac cacactaact tcatcatcat gggccttagc ccatttacca aatctcttac   16020
ccttaggaac cgcatgtaaa agatagttga agtggctttg gtcatcaagt ttcagacagt   16080
taaccattgc agctggcata atgcaatcta catgctggct caaactattg tcgagccaaa   16140
attgattata gttttccgat tgagccaagt tacgttgttt cttaccatat gtgatatcgt   16200
tcataatggc aaacaattcg ttttcagcct tttctttaaa tgaatcggcc aaggcttgaa   16260
tagcagcatc gttacgctgt ttccaagcaa cttcatgttc gttcagttca acgtcatcat   16320
caaaaagact tatagccatt ggagctccag agcaagttgg atgaacagat aagtcatgtg   16380
aatttctggg ttagccgcaa taccgtggta ttggttattt tcaccgacaa tttcatacat   16440
tctaacaatg ctcggcccag gcaatttacc gtagagttcg ttagccagtg acataataaa   16500
gttggaatag tcattgacat ggcgtggagc taatgcacgg agttctttaa agtttttatc   16560
```

```
tttcagtgca gccactactt catcgatagg cgaattggta ttcattacaa tactcagaat    16620
gcctgtatcg attttaccac tggatgagta acggtccagt tggttaactg ttttacggaa    16680
gtcaggaaag ttttgtttaa ctaaagcagc aataacttta aggtcttcga cttcgatatt    16740
ttcgttttta cagattgcta cagcacgatg aatcatttct ttcatcatgg atgtttggtc    16800
tgccggagtg gcttcaccaa atttaataac acgacaacgg gattgaagtg gaccgataat    16860
accatcaata ttgtttgctg taataattac agaacagttt gaggaatagg cttctaagaa    16920
cgaacgaagg tgacgttgag cttcagcaac accagcacgg tcgaattcgt cgataacaat    16980
taccttacgc ttaccttcga tagatttgga agatgcaaaa cgagtaagtt cattacgaac    17040
gaaatcaata cggcagtcag aaccgttaac aaacagcatg tctgaatttg tatcagcaca    17100
caatgcttta gctacggtag ttttacctgt gcctggtgaa gaagagacta ggataatgtt    17160
agggattagg cccttattaa caatggcttg gagggtttct ttatcatgcg caggcagaat    17220
acactcagat aaagtacctg gacgatattt ctgttcgaac atgaattcat tattgtttac    17280
tgtaagcata ttaatttcct caggtttgtt tttacattat actccaaggg aggagattcc    17340
tccctatgct ttagaacgag tggcttgagc ctgcttccat agccaataca taagaagctt    17400
gtgaaccttc aaacttggcg gcgaaacgag catcctgacc ttcaccacga gcccatagca    17460
atacatggta atcagcaggc atcattttca tattagtttt gttgataatg aatttgaatt    17520
cagggccatc atggtctgca accactaagg aatacaatgg acgtgccagg tccttatcat    17580
caacttgctt gtagccattt attacaattt taccattgtc tacagtaata gcaaatgtat    17640
caatactcag accagaggac acacgcatca gctgctggta atcttcagct ttaaggtcaa    17700
aaataacttc agccaccggg aatggaatag ctttgcttgg gaatgcaatt gtacttgggt    17760
cggcaatagg ccacttaata gttgaacgtt ggtctttaat aattaaagtg gtttggtctt    17820
cacttaccga aacttcagca ctatcggata ccaatgatag aatacttaag aagccgttca    17880
aatcgtagat tgcggcttcg atatcaaagg tatcacttac agtagcttca ccataacttg    17940
cacctgttac tgaacgagtt agaatagtgt taccaggttt aagcatgata cctgggttaa    18000
taccggagaa gtttttcaga atgttaagag tttctttaga gaatttcata atgtttcctt    18060
atcaagtcaa aaattaatta agcaataacg atcatttgtt tacgaatgga ttcaggcaga    18120
gattcaatat actctggaat ctgggaagca acaatagcac cggcttcaag caactgttcg    18180
tcaaaatcta cgcaataatc atcttcgaga cgttcagaac catcacggtc gataaccagt    18240
ttagcacctg cggccagtga atcattatag tggcgacgca taatttctac ccacttatcg    18300
gatacgtcgt tatcaatgat accgtagagc atgaacttag tttcttgtgg aagagattgc    18360
aggcgacgtg cagagtcagt atcaatattc agtacccatg atttacggat acggttttgg    18420
ttatgtgggt tggaatcagt acgaatggtt ttaacttgga tatctttaac agtaatagcg    18480
ttagcaaaca taatattttc tctcatttgg ttggtagatg tattataaat caatatttta    18540
aagcacttaa cgtttaatca aagtattcat aaacgaacca ggctgggttt ctgttcgaca    18600
tgattctatc atactctgac ttaaaagcat ttcggagata atcttcagta acaagatgtt    18660
cgtctccaga gaagttgtta actaaaacat atctctttat ttcaggaacg gccaacaaat    18720
gctggcctgt tataaaatca ctcattccat caccgtgaat cgtccaactt tcttcatttg    18780
aagatgttgg ccataagctt gtgggtcatg gtctcggtga gagataatga acacgttcgt    18840
atcctcaagg ctattcaaga tggttgcaat ggtcttaacg ccttcagcgt cagtagcact    18900
gtcaaatacc tcatcaagaa ttaacgtgct gatattaaca cctgatacct tagaagcaat    18960
```

```
atcacgccat gtaaaaagta gtgcgatatc aatacgtgct ttctcaccct gtgaaaatga   19020
agcataacta aagtcttcac gtccacgtga tttaatcgtc tcattgaact cttcgtctag   19080
tgtaaagacg tagtcggctt ccataatctt caaataagaa tttatctgct tattaaagat   19140
aggaatgtat ttcttaataa tggaaccttt aatacctgtg tccttcaaca tttctgtcag   19200
aattccacga tgatatttt ccattaccaa ggacgatttg gtagagacga ttttatcaag   19260
ctctgcttga agcgcggcaa tctcttcagc attacttacg aactcagcag ctgcttggtc   19320
gattaatact ttaactttt tagctttctc tacagcagta atggcttgtt gcttatgagt   19380
agctatctga gatttaatag ccagtgcttt attacgttgt tcggttactt ggtccttaat   19440
gagcttgagt tcttggtact gctcattaat cttatccaaa gattttgaa gctcaaagtt   19500 cttatcctta attttagtaa ggatatttcc atgctcttcc aatccttgca tacacgtagg   19560
gcagtggccg cctgtttcgt ataatttcac aaccttagta aaggttgcca tatcattctt   19620
gattgcaaat cctttattgc tcaggtcact catagagttg ctagggtcat catcgactat   19680
gacattgagt aattcatcag tcagttttc tatattgccc ttcgcagtcc tggcttcttt   19740
aacgagctca tcgtacattg tttgtagacg tgctgcattt tcaccggata atttacgctg   19800
acgttcttcg ttgtcattat aaattttaat ttgctgggta atagaatcct gtttaacgtc   19860
gattacttgg atttggctat tagtctcacg aatcaaagat ttgttcaact tgtccatatc   19920
cgctaataca gaaacctcta acaggtcttc cacaagcttt cggcgcgcag gggtcgacaa   19980
acccatgaaa ggggtatacc ctgctgtacc aagtacgaca atctgtttga aactggcata   20040
tgacattccg ataagctgtt caaattctgc ttggaagtct ttactgctgg cagattcatc   20100
aagacgttca ccgccacaag agatttcaaa aacgttggt ttttgcccgc gtttgatgta   20160
gtattctttg ccatcatatt ccatccacag ttcgaccaaa aggtctttct tattacttga   20220
gttaattaat tgcccttct taacatcacg aaaaggctta ccgaacagag caaatgtaac   20280
ggcttcaagg aacgtagatt taccagcgcc atttttaccg gtgactaagg tcttttggac   20340
cttgtcaagt tggattgtaa taggttgctg gcctaccgac ataatatttt tatacgttac   20400 tttcttttaac ttaaaagtct tcatcgttat aagcatcctt gatgcatgat tcagccatat   20460
gaattaatgt ttctggagta tcatctacca ttacattaaa gctaaattcc acagcccaat   20520
cagtagcaac ataaacttta ataagctcgt tggtatcacg agtgctcacg gcttcaaacc   20580
agaacttaat gatattcgtt tggttatcgt catcaataac gatgcagtcg tgttctagtt   20640
caagtcctga tttttgaatt catctaaagt catcgtgtaa cctcattata aagttgtgca   20700
gccatagtct taagggcttt aacatcgtct tcagtgtggc catcaggaag ggcattgata   20760
taatcataca tcatgtccaa gagggattta acttcatctt cctcttcaga atcatcgata   20820
tcaacactgt tatctaccctt agacacgata cgtaaagaat ggacaacctt ttcaagctct   20880
gattcgaact tagtaagacc gtcatcaatt ttatcgacta taacacgaac tgcgatattt   20940
gtaaaatctt tgtaatcgat agtcgcattt ggataatgaa tcttacggtg ccaacaggtt   21000
tcattaatga cgaaatccat cttatgagtt tctgtatcga aaatccagaa gccgcgaggg   21060
tcgttttcat caccagcagt cagggtccat ggggtaccaa tatacttaac gtttgctgca   21120
tcagaaatag tatggaagtg cccagaccat acctgcttat acttcttaag gaaatcaggt   21180
tctaaaccat gggatttcat tccttttatag aaatagaaac catttaattc ccagtgacct   21240
atacagaaat ctgccgtggt attttgata tggtccatga tatcggtcgt gttttcttca   21300
```

-continued

```
cacatccatg gaatcaaatc aatttcggtg ccatcaaagt taaccgtagt aggtttctca    21360
ataaccttga tatggtcata tttacccaga acttcagaag cagcgttcgg tgtcaaggta    21420
tttttgtagt gggcatcgtg gttgcctacg acagtataca tggtaatgcc gttggtttta    21480
agcaaatctg aaatatgtct agcaaattcc atgcacttat gagtaattgc tttacgaaca    21540
tcaaatatat caccgtactg aatccataca gtaatgccat ttgctttaga ataattgatg    21600
gcatctttga tgccggccaa ttggatgttt tgcacccaag ggtcgtcgtt cttcactcca    21660
aggtgccagt cacctgtgtt taatattttc ataagccaag cgccgttatt gcagtgcaaa    21720
ataaaattat tgaaatgaac ccgtcaggag tagaaaagaa tcctatccaa caggctcgtg    21780
tgaatgtgta gaatgccatg aataacacga catatcctaa aaatagttcc atatgttctc    21840
ctcagttggt tcattttatc atccgaatat aaagcaaaaa aggagcctaa gctccttttac   21900
caactaatac accatacaga ggttcgtgat tagacctgaa cttgataggc ttatatgtaa    21960
tagtaccttc attttctgct ttaatacgag cggcttcaaa tttaagcaac atctcatttt    22020
tgtcagattt aatcttatca aaatccatcg aattcgtcat tcatacaacc tcttaaactt    22080
tttcgtattc gtctttcatt agccacctgt ccatgttatc atcgttgcca ccatttctta    22140
agttggtgtg aatccaccca aaccttggct acaggctcaa tcttaaaaat accatcagaa    22200
tattggccca tcattttata ttcggtttcg gactgcttaa tacagatatt accgtatgag    22260
cgaagtctaa aggcggcccc aataagaagc cgtttaaagg gttatttac tagggccatt     22320
gacgatttcc caaatttgtt tgcgggtaga ttcccacatc aattgaacaa gttcatcagt    22380
aacaggttga cggtaaatac cacgtaattt aattaaagcg tacttatatg cttcaaagtt    22440
gttttcaagt acagcgcctt gggcatggag atttaaacga cggatttcac gagcattctt    22500
cttaagaatc ttagccgctt gagaattagc ttctttaata ttatgctctt ctaaacgttg    22560
ctgggcttct tcaatttgct catcggtcaa ttgagaaatg tcacggcttt gcatattatt    22620
cctttggagt caattcaata gtgaagtaga aattagcgtt tcaacatga taacgataat     22680
ctacgttatt gtcaggagaa gtgaattcaa tattcctgac gttaagtggg tcaatatcaa    22740
taggaaggcc tttaacatcc cgtaatatca atttaataaa ataagggagt gcttcgaagt    22800
cttccattcc atctaaaagt ggagtgatat taatctgatg ttccatataa aaatccagt     22860
tcaccaactt taggttcggc actcttatca gaccctggtg ctttagttaa agaggtttca    22920
tactgtgtca ttttatcgta gatatcttgg ataaaggttt catctgcaat acctaccata    22980
tcgtcatcat tactgtcata gacattatgg acgaagtagc tatatttctt tgccatttct    23040
ttacgttctt ttttgatacg ctgaacgaag gcattaaaac aagccatagt gatatatgca    23100
tgcgggttgt cgtatttgt ttcgtcgaag ttgtgaagac ctttaatcga agcttcgatt     23160
ccatcagcta tcatttcctg ccgccaagat tgggtatatc ctgagaagtt gaaacgcttg    23220
ctgaggcctt ctgctataag cataatagcc aatcctatag tatcattttg tctaatgatt    23280
ttattagggt cggtattagc atataattcc tgcttccaac ttgtaatagc tttaagaagc    23340
tccttgttat ttacataatt atttttgtt aacttcacct gattcataag ccctcttaaa     23400
cctatcaact agtggtctaa aattatttat cgtatacgga taacccagtt cacagcatt     23460
gcgccagaat ttagaataac tagggcgtcc ttccttaatc caaagttcat ggaactcatc    23520
atataataca tatgttggat ttttagcaaa cttggaataa ttctctatag agtaatattc    23580
tttgttcttt ttacttttgg cctctctaac ttcaggattg gcattatatt ctttatggat    23640
tcgccgcatc atttctcgat gctcttcgtt ttcccaagac ttttaatag agttggaaac     23700
```

```
ccgctctttta tattcagggt cctgccagcg ttcggtaact tctttagact gttcttcaag    23760
tctttccggt gtcggaggag cataaccacc tataccacca ggtttcatat tgacacagtt    23820
agttatttcg gacatagcat tttctaccaa aagctcttca aattcaaaag caagctcact    23880
tgtctcaaaa taacataagg cctctatatt aaaagagcat ttccctgagg ccttagcatc    23940
ttctacgaat ttgccactac cgacatacec gtcatctata aatccggtgt gtttaccgaa    24000
atagtaataa gtatcatttt cggattttat agtggtcata taacaatagt gcataacgat    24060
taatctttaa tttaaataat gaatctatta tataccaatt ggcttaaagc atcaacggag    24120
taagcaataa gcctgaaata ctgtttcaag gattttttg aactcttcaa aggaaggggc     24180
tccttcaaac ccttggcttt gaatgtaaag acagaattgt tggtaaagga ccaaatattc    24240
tgattggttg tatttggaaa tatgagactt ccacacttcg gaagtctctc cacaaacaaa    24300
ctcaacattc atatagctat ctattaagaa aatccctagt ccttcgtagg cgagggtggt    24360
ggatacgggt tcattgtag gaatcgagct ccttccaatg cgtcatccag attatcaaac     24420
tcgtccacgt aatcaacacc gccaacttcg tccttcgcat acaaccaata ctggtggaat    24480
tcatattcaa taataaagtg ggcaccttca atctggagag ccccatcacc gttaaattga    24540
actgcataac ctgtaaagcg gacatcattc aagagttctt ctttcatagc aatcatttcc    24600
aagtttttat cgtaattaga gagttttatt ttaatcattt aaataatcct caaattcatt    24660
taatgtcatg ccttcgtccc aagctatttt tgggtcaggc attttcatat aagtggtctt    24720
agagcttata ggaaatatcc tgaaatcacg atgacttcca cttagcatct tagccgcttt    24780
tataatagtt tcaatattat tcatcatggg cgtacgttgg aacccggcta aagctttaag    24840
gactattata accgatacat cttcaggcaa attactcatt tagccgcctt aacaatttta    24900
aggtcaacga attttttctt acgttggttt ttcatacgac ggatagtttt atccgagatt    24960
tcaccagggg cccaagcttt agattcaaca ccaaaggcag cgacatcgaa ttcatcaagg    25020
atatattgaa ccaggatttc acgaataccg ttcttaccaa ttttctggtc tttagagtgc    25080
atgattggta atagttcagc aacccattgg tcaagaacct gaggagttac aaaacctgtt    25140
ttcatcagtt cgtttacttt atcgaaagcg aaagagttca gtacgttttt aatagcttgt    25200
gacataataa tttcctcagt tttaaagtta taatccgtgg gaccattata ctctggtccc    25260
aagagtttgt aaactatttt tgtgctttag cgcctttcca gccttcatac atcattgctg    25320
cggaaattaa caaagcaccc gagcaacttg aatatttgtg attccaaaac cagttcagaa    25380
atacttcgtc atcaatacct tgagctatca tattttcaaa gaactgacga cgagcttcag    25440
caattcgctg tgataattta gattcaggat tcatttaaat tttccaattg ccattttcat    25500
caatgaattt aacccagtca tttaccgacc acttggttgt atcgccttt ggagcaacat     25560 ttaaagtata tagcccctgc ttaaaaagca ttcgtttgat attcatattt tcctcagctg    25620
taacgataac actcgtttga tttacgtttt gcaactcgat gagaagtatt gtaatcaggc    25680
tcatcatcgt tgtaaacatc ttttttcagc tttctcactt ctttacgaag ctggcgattc    25740
atttcattct taacttcgga atcaacgcct ctcatacgtt tccacttgtc agaacggaag    25800
atattttctt caaccagttc ctggcttaca ccgtccggtg ctttgcggcg acccgaataa    25860
taaaaatctt ttacagacaa ttctttacga cggatagttt tacccatagt tacctcagca    25920
gtttgcatca ataagatttt taatgtaatt aacgtctgca atactcagat cgagtttaat    25980
agctttcaga cgttcatcca gagtaaggaa agttactcgc ttccaattct taacagggca    26040
```

-continued

```
gcaataagtc ttaggaccgt tagcgatttc aatattttta tctgtgatgg tgataaaaat   26100
caagcgtaca taatcgagat tcagggtgat gacatttctc tttgcatgta ttttcaggct   26160
catgagttaa tttcctttgc tactgaacaa atacagaac  ggtcgcacac cattaacgga   26220
gcatcagggt gagtcaaagg ttgataccat acatcgagat ttgttacctt tgttacttga   26280
acagggtagc catttactga ataatactgg tcgactttaa tttctttatc ttggatagtc   26340
ataatgttct cctcatgtgt tgataggata gactataaca cgtgaggaga ggaagtaaac   26400
actaatcttc aattaaatct cggtcatagc caagttcaat caaaagtgac ttaaaggcag   26460
gaatattttc tattttctta ttatcgacaa agatgacagg atagcgtatc gctaagctct   26520
tgaagcctgc gcgtttggcc aatgatacta taagaggctt gtcatatacc gcgccagacg   26580
gcgtctggtt aatcacagga tagaaagtat gtgggataga aagggaattt aggagcgata   26640
gaactgcaat gcaccctgga cagcgcatga ctgcctcagg gataccgtag atttcgattt   26700
tagttaactt ttggtccaca ggaaataact ccttggtagt cccaggtttt tagaacttcg   26760
tcctcactag ttccatacgg gacgtaaatc tgaataagaa atccgtatc  gtcgaagctg   26820
aaataaaccg tcggtttgat tccgtgaatc tctgatagag catagatgtc cttgaggtct   26880
tcttccttat cgacaaagaa ttccgggttc aggtcacagt catggaagta ccaatcatca   26940
ccgaatttgt cccatgcggt ccaattcaaa gctacatatt cttcaaaacg tttcattctt   27000
tcaccttcat cattttagaa ataacaccat ggacagactg gattcgtttt tcgaactcgg   27060
accccttcaag accttttttca gtactcaggg caccgataat aacaaacagt aatccaaacg   27120
ggatgaccag gattaaaagg cacacgataa acagggcaaa tgtaatattg gccaggatat   27180
cagaaacagc attacgaaat ttgttcatta aagaacccac atgttagtta caacaaataa   27240
ccattgagca ggatactcaa cacccataat acgcaccgca tcgttcagag attcgattaa   27300
agcataaaat gtgtagccat aaaaattaat catttaagcg atttcctcag ttgttttttg   27360
aatgaatcca ccatttgttt cttagtggca gattcattat aagtcattcc gtgtgaaagc   27420
atttcagcaa tcatttcttc cttacccaac ctgctgaact cttttggtttt atcaggaacg   27480
aaattaggat gaatattgtt ttcagtataa tcagctttca gatagaccag caaattctct   27540
aaccattcga ggtagtcaac gttttgacct ttaagaccag aacggttgaa cttatgcttc   27600
atttgtcctt ctgcagcatt gcacaggtta catagtaaac cacgaaccttt accggctttt   27660
ggcccgttta actcgtggtc gtggtcaagg tggttacttt gaacatcagg gtttaattca   27720
cgttacaaa  tcaaacactt accatgttgt gcatcataaa gttttttgttt ttcttctttg   27780
tataatttgc cggtcaacaa cataataaac ccttaccatt attagataag ggtatttatt   27840
aatatcctaa tagtttagca gtgcaactta gcactaacaa caatccgaat aaaacaactc   27900
ctacccaaaa taccgtaata agagcctcca tatcagaccc catagaatga acgatgcaaa   27960
cgtttgaatt gacgaatcat cttttttagta ggacgggtgt ataatcctac acaggtggcc   28020
ataaactggt cagttggact tcctttgata agaagtttcc agaccttacc gccatttaat   28080
ttttcggtat agactaatac agttttcatg cgacctcaaa ttcattatca tcgttagtcc   28140
aaaaacacca gaatgaagct ttagtatctt caaacatttc tttagtgtat tcgtatacct   28200
taccattgaa ttcgatagca gttacgccga tgatttcagg gtcgccccat ggagaaatct   28260
ccaccttcaa gattttaact tcagcgcctt cacaaagctc acctgactca aaaccacgat   28320
taccatttaa ttcaggccag tcaacataat ggtcgcatc  ttcttcagta atacgaacag   28380
tttttacctcc aaattcaaat aaattcatca gaaggcctca tcggaaaagc gaagttgagc   28440
```

```
ttcaagccaa tgaatataat cggctgcagc tttaatcaaa tcggattcta agtcaggtaa    28500
agaacccaaa tccgacaatt cgtaaagcga atgttcaatc agacggcctt tatgacggcc    28560
aacttcaatt ttggtactca tatccaaact ccatatcgat gaaatcattg tttgaaggtt    28620
cattatactc tatttcggaa tcgttgtaaa ccggttcctc tggctcggta gttttccacc    28680
gagcgacata ccatggctta acggtcacac caccaactac ttacttcaaa atcaggttca    28740
ccgtgttccc agtaccaagg gccgactgga tgccaatcgc catgttcatc ttcttcaaat    28800
tcttcagatt caagcccaac gtattgccat tggacttcat aagcggtgcc acctattaca    28860
acggtgttct cgccatatgg gtgagctaca gcaaagtcta taccttctgc tttagccaac    28920
caaaccatat attcgtatag tttatattcc aggtcatctt cggtgccatc acctagaaaa    28980
atggtttgtt cgtttaattc aatcataatt ccaccataaa ttcaaatagc tggtcacgta    29040
cacaagtatc agtccagccc cattcgttgg cttcttcttt taaccaatcc gggagatttg    29100
ccaatacggt ttctttacta ggcgcaggag tatcaaactc gcttgtaaac tctcttgcgc    29160
aggttccata agctatatca aattcaatca tttgaagttc cagaatgaag caccaaccag    29220
aaataaaggc caacaaatca tagacgtcag ccaccaacaa aagtcacctg caccgaaatc    29280
atctaattta gctagggtct tagcataacc aataccgatg ataagataca aaatacccaa    29340
caataattca atcatttgaa atatgctcgc aattggtcaa agccaccaat agaagttccg    29400
tccggagcaa atacctgagg catagtcaaa cccacctgag attcgcgacc aagcgcagtc    29460
aagagttcag caatcttctc atcatcaaat acgccttttt ccggcatcac gttaatgaat    29520
tcgtaaggtt gtttcttaac atcaagcaga cgtttggcat tatcacagaa aacacaacgg    29580
tgaatatttg aatcgtaacc ataaacttta aacattttaa attcctaata tttgtttgaa    29640
tgcttcagaa cggtcgagtt ctgttccata tttttccatg tgctcatatt ttaaattata    29700
cacatcagat agtatattat tatacgagcg agttaaagca gattttaaaa ctgaataact    29760
gtctgggaat ttaccatgct ctttataata agctagggta agttcgcgga ctgccttatc    29820
ggcagcctct acatattctt tacgctttgc cattttcgtc tcgctcaaat ttgtgtttac    29880 aatgcggca tttgtaacga agattactag tctgccaatg gaccaattgg acctgttctg    29940
taccgcactc aggacagtta ggaacatcct tagaagcttg ttctcgtcgt gcgaccatag    30000
ccattacagc atcccaatta acggcatcac cataatcatc acaaccatga attttaccaa    30060
ccaattcaac ttcaacatcc gcggctttaa taaatttcaa taaaccggta ttagatgctg    30120
aagcaatatc ttcagctaaa cgttgtttca tttcagcagc tccagagctt gttcaagacg    30180
gtctaaacga ttggtagact cttcccaaag tttcttggcg gcggtatatt ggccggtcag    30240 tttttgtta atagcaaggg catctttata cgcttttcct aaggccacga tttccggtaa    30300
cttggattta gtaattggtg tagggcat gatagggctg ttcaagtcgt taatcaaatc    30360
ttctaatgta gcgggctctt tatcagtgtt cacaatttcc tcacattttt cttggtaaat    30420
ttcagcgtca gttttggaa cggtacattt gatttcacgg actgttacta agacttcata    30480
tcctttccat cctaagtggt gtttaacttc ttgggtctca tatttctcta cggtatccat    30540
cagagctaaa gcctgttcga tagtattcaa ggtatcgtaa gcaatatctt gatactttac    30600
aacttccaca tcatctttag gtttcctatt aggtgaccaa ataacagaaa taatagcttt    30660
tcctttataa ctatttgttt taatcatgca attagccatc gggtgaatag tacgacaatc    30720
accggaaact atagttttag aggccgcttt gagaattaat gcagagttag ctttgaattc    30780
```

```
ggtaacccaa cgttgtggaa ataaactact agggtccata cctttaattt tgatataact    30840
ttttatggta tcaccaaacc atttgtagct aacagcatgg ctagaacccg gatgtttctc    30900
tttgccaaac tctgaaagga tgtccttatt gaccagtcgc gaaagcagtc gagaaccttt    30960
aaatgtttta atgatatcat gaatgcacaa acggcctgca atcttttcga tttcagcttt    31020
gaaacagcgc gataatgcat catcaatttg gtcgacccat ttattgatat tagaaactat    31080
taccacatat ggggttaatg gaggggtgtt ggcagtgata tacgtagtaa aggcattgat    31140
gtattcagta cgagtcatga tattctcctc aagttgatag aaagattata ctccatccat    31200
ccttggatgt aaacattatt ttagagctaa tactgcggcg cggagcttgt cacgctggag    31260
ttccatgttc ttgatgcgaa tcaatacgtc ttgaatactc ttttctcat cttcgatctg     31320 accatttaaa cggtggattg attcctggag gtggtcctca tgatacttct cgataggttt    31380
catcgtaggg ttagtaacca ccatagaatt ctcaggcttg attttccact gatactgttt    31440
ggaattgaat ggactaggca cagccgtggt tttgaatttg tcataggctg catactggcc    31500
tacgctgtca catgatactg cagagatacg tcgttccatt tccggttcct tttgttggga    31560
ttgataaggg gcataagaca aaagatattc acgagttagt ttaacattaa aatacactgc    31620
atctgctcgc ccggaacaat cagcatattc atctgttgta accttatatg attctacggc    31680
cttaatacga gtcattgctt ctctgaataa ggtttcaaat gctccacgaa gggccttatt    31740
accttttgag gtaggacgga aacgaacttg aataccgtca gccaaaatat taatgactag    31800
gttacgagcc gtaaaattaa tattcttgat attgatatga accgtagaaa tacgtcctgc    31860
ggtagccaag aggtctttga tattagctcg taatgttgca ccaaacaggt gggccgggca    31920
acggcaataa tcgttcaaag aactaatata agtcccttta cgtcctacac cataagtata    31980
attaccatta caaatatggc cgaagtcggc cagccgatcg atagcgatac gacgtgtggt    32040
atcaaaatca tatcgggaat attctttacg tgttttaatg ttcatatcaa agtccaaata    32100 attttcata gaatttagcc ataggccagg ttataataaa aactatccca aacatagcaa    32160
gaactggcca gataaaggtg gcaaacgctg cttcaccgcc tgagttaatt tccatatgat    32220
tacgaccaat aaggacagta atgaatccta tcacaaggta tccaaaaata aaactgataa    32280
ttatagccat attaatcctt aagaagattt aggatatcga tatattttg acgttcagcc     32340 ttagctttag cattcagacc agagagtcgg aaaatctcat catcttgttg ttggattgta    32400
acattcaagc aagtaagcaa attgctaaaa tactcgattt gagattgatg cttctcattg    32460
ctgcgcactg gcacaggttc cggtttagga gctcgttccg aatgactctt aacttcatta    32520
cccggcttaa caagtttaat acgccggcct gtactggtat taacattatc gaaggtaaga    32580
ataccgctac gttcgagttc ggacaaagcc agtcgaagat ggaatttcca attgtcatat    32640
tgacaaccac taaaagttga agtaagatac tcgttttcgt tacccggttg gttgacaata    32700
ttaaagataa tccaatcgcc tgaaccatta gtcttaaatg gcatttgctt atctttacct    32760
aaagctagac gagcacccag tgctagtaaa cgacgttggt tagtacgaag gtctttaaca    32820
acttcatcaa atgacatcgc cgggattaaa cgaccataga ggtcatagcc tttgttataa    32880
tttctaagaa taattctggc gttagcacga gtcaacatac cggccctgtg aagagatttc    32940
atgactcggt cttctaacgt aaacaaacct ttagtcttgt caaagatttt agtgaattca    33000
tctacagaaa tacaaacttc aaacttttcc cacatcatgg ccaaaacctt ttcaaccact    33060
tctttattca gtggaatacg accaaattta ataacttttt taacttcaga acgaatttga    33120
ttaattgcct gtgacataat aatttcctca gtaagtaatt aagaacctag aaccattata    33180
```

```
ccatccttgg tataaagcgt ttatgcgaga accgtctttta aacgctcttc aaatttctga    33240
agcagagctt ggcgttcagc tcgttgtgat ttgtactgct cgatacgacc tgaagtgagg    33300
gcgtactgtt cgtttactga ttcccgcatg aattcaggaa tctctttaca agctttgatt    33360
tcgtcaaact tatcaataac agcttgttgt tcagcaatca gattatcgaa ataagcgata    33420
tcagatttaa cgtttgccag gtcagattcg gtaggcatta aacgtttgtt acgttcagct    33480
tgataagctt gattgttttc acgactccag tgaagagtac gtttttttgtt agtgttttta    33540 tagagctcta caataccaac tgaatcgatg actgcaatcc aattccaacg cttttgtaa    33600 atctctcctc cagatacggt aatctcatta ccacaagcaa cgtcgttaaa gaacttgctt    33660 tgttttcag atttgaaatt accgttgttg aaattaataa gtgaaaaaat atctttagcg    33720
ttcatgataa cctccagtag ttgataggtc tatagtatca tttctactgg agatgtaaac    33780
aactaataga aacttttttc acctgcttgt ccactaaacc acgctgattg ggtgttctct    33840
ttccgttgat gttcaatacg aatgcgatat tcattcctga tggcgcagag ttcacctcgg    33900
aagtcgcctg tcaactttac ctgcttgtgg tctagattta ttaaggcctg gtcttcgcg    33960 gccaggagca gtctcttgta gtctccttct tcacaatcag ttttataaac tctattagta    34020
tatccatcga taagttcttt atcatagtcc tcgacagact gtttcatggc tttggaaaaa    34080
gtctgacctg cgttataaag attgtaaata aattgttcga acataattc acctttattt    34140 cagaagtgta acttcagcga tttcgctcca gtcattttta tcggtggcaa tgaagtccgc    34200
cagataaaga gctgtacgta atgatacgtt acgaagacga gatacattag ccttcatcca    34260
ggacagtgct tgataagtct cggcatcagt cagaccacgg ttttgcatca tatcagtgga    34320
caggataacg tcttcaacac ggaccataat ctcttcgttc gagtgaactc cgaggtctaa    34380
gtaaactgaa cgcgatacta aagcctggag gtgtggagca agtttagttc cacgctctaa    34440
ttcacggtcg atatcaacgt tggtgatgaa cacgatggtg ccttcgtatt cgaattcttt    34500
atcgatgttt ttatcatcga ggtaagaact tgaagtgctc cagcacacct tacgttttc    34560 acctgtatcc aatgctgctt ttaacaggtt caggatatcc atatcagaga atacatcaac    34620
atcatcaata agaagaacac tattagggcc gcggttattc caaagctgct cgtaaagacc    34680
gattccacta atctttccgt tgattgattt atattcgata gtttcatttt cgtgggcatt    34740
ttgtaatgct ttatccaaag aatacgtttt accaatacct gcggcaccag agatgataag    34800
ggaacgaatt ttaccatcga tgattccgtt ggtcatcatg ttcattactt taaaacgttt    34860
gttaatgcga tgtttcattt cttcagcgga ttcagtaaca actgcaggag cttcagcacc    34920
ttccatttca acgtcacatt tgaacaccca tacaccacgt tcaacaccat caatctgtac    34980
gaataccttg ccgtcaccga ggtgagcttc tgattcatga attttattag gaaccaggt    35040 tttacctgaa ctcatgaacg taccagagat tacattaccg cgatagatac ctttgttgat    35100
tttgatagtt aacattatat tctccatttc actcagtaga tttgataggt ccataataac    35160
atgctctacg agagtgtaaa ctcttttttg cactaaaccc aaaaaaggcc cgaaggcctt    35220
tatcatttat aatacgagtt atggtttttct aggtaaacct gctcaacgaa cttgtcccag    35280
aacttcatgt ctaccttctc aggcataccg ttcttagcgg cccagatagc attagtttcg    35340
acttcatcaa cgatagcttc aagttcggcc tgtacatctt taaaagcatg aagcccttgt    35400
ttgatttcaa ggataaacgg cgctgtacgt aaaggatatt gaaggtcacc agtttgatag    35460
atttccttca actgataacc agcacgataa gcatggctca gagctttcca gtcaataacct    35520
```

```
tcgttagctt cagccttacg agcacgttca ccatattcgg catcaagctt attcagagat   35580
tgcttgagct ctattaatga caaggtggtt tggtacttac gtcccaacac agtatagaac   35640
gtttgcgggc ctgttttctc atggttatga aatacccatt cacagaattc gttttcaggg   35700
agtcgatgtt tgatatcttc taccttagta cgacgttgtt tagtagaacc atcttcttgg   35760
taatcaatcc actgttcagg aatctggtta acgatagcca gtacaccacg caaagcagcc   35820
agacgagaac ccttaacacc atatttagaa gcttgcttac ggacgtaccc caaataggct   35880
ttcatgttag tcgtatagaa gcgtgaacga ttgtcttgaa taaatttcca tacatcaggt   35940
aaatcagatt taaccaccag ttcaggtgga gtgtggagca tatccagagc aacggtttcg   36000
ccatcagcag ccagtttaaa gaaatatttc aggctataaa gctcatggtc aacatcatct   36060
ttagtgtttt tggaagcagt gttattcgtg ttcaggttgg tatggttcat agccgtacct   36120
aacagaatat cacgcggatg tggaacaaag atttctttaa aatcgacatc agattccgga   36180
gtacttgttc cgtaaaggtg gctaccgaag tagcctttca taacagttct cattctttgc   36240
cctcgaagtg gattacagga cacatcttag atttacgagc tttaatgtat tgaataacga   36300
tgttttcttt aatttccttt ccttcgcgtt gggctttaat acgttcccat tccttttctt   36360
ctctacgcat atcataccat gagtgtaaat tcatcgcacc gaacgccaaa ccaatggata   36420
gtgcaataat gagagctatt gcaatcaacc ctaaacaaa ccctagactc aacagaacag   36480
gggtacttaa tacaaagaaa tgctctaata caccagcgcc tgcaacagtt aatccaaaaa   36540
gcgtactacc agcaacaaca gcacaagcaa aacaagccca aaccattttc cagaaataag   36600
cacacaaaga gtgtggtcga gaatgacggt cataaaaacg atcgtgaagt ttagcgtgcc   36660
aagagtttgt attgataatc ataatatttt ccttaagagt tcatagttgg gataacagag   36720
ttcagataag agactaaaac ttttagttcg tctttagtaa ataccacttc actttcacca   36780
tcgtgtcttt gggtcaagga tagcaaatca cgaccctgat attgatacac ggttaattca   36840
gtatcgtaat ccagttcttc ttcgtcgcct tcaaaggttt cactagagcg aattacagca   36900
tcttgaccag ggactttcca ttcaacttcc ggcttgcatt cttcctggaa cagtttaaaa   36960
atacatttaa agaagttatc agaatcactg atgcttagac attccccgtc tgtttccaaa   37020
ttaaacccgt tgtcatggtt ataaatctgg gcccacatat catcgttaat atcaaataca   37080
cctctaaaac taccattaag atattggtgt ttgtccaaaa cctttaaatt ataaagcggc   37140
ttgatatctt ggatagtcag tacgatttta tcgtcttctt gtgaaagcac aattgcatta   37200
tcaactactt cagcagtcag gtcaccaaac agcccggatg tttcaataat cattttccgt   37260
tcctcatttc acattttgtt taataaaatt taacaactct ttaagagctt catcttcttc   37320
tttagaaagc ctgctgcatt cactagctgg gtaatcattg caaaacgcag tttcaaatct   37380
agcaactgta cctgcatagg cctcgataag ctcttcaagc tttaaatgct tttcttcggt   37440
tttcataaat caccggttat gttttaaaat actataaagc tcttcaactt ggcttgcatc   37500
cagataaatg acctcgtcat cttgttccag aacaatccca cctttaatga gattccattc   37560
caccacttca acagtcatat catcaccgga accggctaat gtttctggtt ctaaaacgat   37620
aataccgtct tcagaattac cactcgggtc atataacatt acagtttcct cgctaactgt   37680
gaaaagaata aaccaattaa aacaggccct acagccattg ttaaccaagc ccagggttct   37740
aagtaataaa tcatctcatg ctcctgtgcc aatagccatt atgctttcaa ctcattcaga   37800
taagcgacta attttctttt agaaccattt aaatcacgct tacactgctc tattccagaa   37860
tatgaatagc cttcacaata ttcaacagcc aggtcattgg atgcgttttc aatgtgccgg   37920
```

```
gcgagtttaa ggatttgttc aatctgttca gtagttaaca tattatcacc agtatttgtt   37980
gatggtagaa attaattctt gggcttgggt agttttcagt ttacatccac aacccttaa    38040 tgtgtcttta aggagccacg gttccttgag ctcgtccttt tctaggcgaa ttctgtatcc   38100
tcgataatcg gcaaagatac ttcggtcgtc aatatctta atctcaagga tacggtcatt    38160
gatttcgtat tctaatgaaa ccgtagtact tgtaagtttc atactgttct cctcattagt   38220
tgataggtct atagtatcat gttcctagag gatgtaaaca cctaaacgaa aaaggtccc    38280 accgaagtga gacctttgat tattctagcg tcagcaaata cttagtctgg taaaagacac   38340
cagtgatatc gtccaaagtc gactggaggg ccttaggaag ggtgtcatag attttatcag   38400
atgctttaag aagctcgtca agaaaatcta ccgggtcctt aggcaagtct gaagcagacg   38460
gtaatgatgc tttatattct ttgccactga atccaagata ttgctcacta aattggtcca   38520
gaggtccttg aacttctaca taatagaagt catacgcttt gtgtcttgca tagcttttgg   38580
tttctaaatg ggctgactta aaataggcta aagaaaccag tagccaacca atataagaat   38640
ccacttcaga ccctcgaccg ggtacgaaat cattgaactt catcttccac cttcattagt   38700
tttacataac gctctccgat ggcacgacct tcaattgagc acgcttctat agtccgacaa   38760
cttgaaatct tccaggaagc cgtaacatag gcccaatagt cttcggaggc ctttacgctg   38820
ggtctactca tttgcgcata aacaggcatc gcactactag caaatgcatc catcaattta   38880
tcattggtat catttgctag tgaaactgta gggcttaaac atcccgccat aaggatacaa   38940
gccgctgtac ggaaaatatc catacaaaag tcctttgttg ttttatacta tttgcctttc   39000
ggccttaacc gatagcgatt accaaaagct aaagctctac ggttagtatt attatttata   39060 gcttttaag cttacgacaa taagaataga acacgtcgtt aaaattatat tcaacccaat    39120
tcctctgtat aggcgaggta atggaaagca tataatgcgc tttaattaaa tccatcccat   39180
ttttattagg acattcttta ttattagcat tatacgtcgc tgctacaacc tctatctctc   39240
ttttgtaagc cacatcatcc atgataggcg aaagaacaat ataagaaata gccacagcga   39300
acgctagaat taaatctttt gaatttaggt ccatagtacc ctcaactcgt tatttctatc   39360
cagtgcttcc tgcacaatga cacgtaagaa tcgttgccac ctatagaaac ttgggctccg   39420
tccttaattg cgataccatc ttggatacga gccgtcatag tagctttacg gccgcaatgg   39480
cacacacctt tgtactcaac gagtttatct gctgtagcga gtaattcagc agagccagga   39540
aacagtttac cctgaaaatc agttcttagt ccatagcaca taaccggaac attataattg   39600
tctactatct ttgccagttg ttttatctgt atcggttcta agaactgtgc ttcatccaca   39660
aatacacagt ggatatcttt ttgagattca gcccaacgat agaactcgta taggtccata   39720
tccggagtca ctgcattagc ctcttggcta atccctatac gagacgaaat gctatggctt   39780
gattctctat tgtctatcgc aggctttaaa aggagtacgc ccataccgcg ttctttgtag   39840
ttatgagcgg ctgttagcaa tgaagcagtc ttcccggaat tcattccgc atagtgaaaa    39900 taaagttgag ccatattacc ttcttaaaga ctatttacat aagcaattaa ttcattttct   39960
ttctcatcaa accgactggc gaattcttcc tggtgttcgg catctatagg gccatattca   40020
tcataaaaag aatttgcttc tgcatgctca tctagaagtt catggataag ctcaaacaat   40080
ttatctttct gttctttact cagactcata accattgtac ctttaagcaa tattcttcta   40140
cgtgctgttt acgtttattt ttatctataa aagtatattc aacatattcg ccaatatacc   40200
atttatcagt gttgtgttga cttttatag ggcatttagt tactcgggtt tcggtccagt    40260
```

```
gtcgaataat ttccgctttg tttttagggt caaacggatg cgggtaatgg gctttcataa    40320
tctaccacca ctaaattaat atcaggagta aacaaattaa tcaattggta aaccttgtcc    40380
caatcaccac cagcaatacc acaaccaatg cgaggaatat aaattcttgg tttaaacaaa    40440
agaccttttg cttgttgatt taattctatc atacagtttta ctaaagcacc ataatcaaga   40500
ttagggcctg gttcgtattg ggtatataaa ttatagcaaa tttggccatt attacctgta    40560
gcttgagtaa acgtgccaag ttttgccaaa ttgcctaaat aagtagtttt atcgatagcg    40620
agaataggtg gataagcctt agccaattgt ccggctacac ctgaacccat tgtatggaaa    40680
cagttgcacc cgtgagcaac attattacct tgaagaaaca gggcgacgat atcgcccttaa   40740
atataatcaa taatcattta gagtttaatc ctcggttgta agagtcaacg agtctgtcta    40800
ccatagacgc gcacatttct ttgtactttt tatcagatgg aatacattca gtaacgttta    40860
gacgttgctc gtatcttta gaaagagttt tctctttcat tcggcgatgc tctacgtcat     40920
tctggccatc tttaaaagca gctgtgattt ttgaactgaa ttcgataatg cattcagtat    40980
tactcggatg acaataatct tttgctgtac gggtagcata ctcgacaatt gaattattac    41040
tatcatcaac ttgtgacgct aatactcccg gagcaatcaa cataagcgct atagtcatct    41100
gcttaatcat ttaatacacc gcctcaaaca tcttttaga ttttaggtaa ttggccttttt    41160
ctagaacttc agaagcatat ttactgcctg ctttgacgtt ccagcccgca ttataagaag    41220
caatcgcttt tctcaggtca cctttgtgaa catcaatcca ataagacagt tcaatgtagg    41280
cccaagaggc actgttctgt cgttttttgga ccatacggat tatttcttta tcagacatct   41340
tccaacctac ctgttgaaca cgacttctta acgtaggcaa gtaattttgg aacatgccat    41400
aagcatggtg cttatcttta tttaaaacctt gattaattcc ggcggatgat tcctgccata   41460
gtaatccggc cataatatat cctaatcctt tttgattagg gttttctttg aactttcccg    41520
acttttggta ttgttcaccg aaagcatacg cataatgtaa attatcgagt tgttcattac    41580
tgaaagtagg ctctacgcta tgggcagaca tactaactgt caatagtaaa gtggctaata    41640
cttttttcat gagacctcat tattaaagat agattacttt cgtgctggtt ttaccttcta    41700
aacgtttaga gttaacaaat gccatacgac atttaaggga atatccttta tcaggatgtt    41760
tacggtctac agtcatacct agccataagg ttttatcggt aatttcgaga cgcaatgggc    41820
gatacacttt accagggaca atttcggatt ctacatcagg cagaggttcc tggattaaga    41880
attcatggat ttctttaaca tggttatgga gttgcttgaa taaagcaaaa acgtatttttt   41940
cgtcgatttc acgttggata gcacggtcca acaaatgatt agagtactta ataaagaagg    42000
ctgggactcc gctcttaatg gcggcttttt tgatggacgc attcagttca cggaattcgg    42060
tttcgaactg acgacgtaat ttgttgcggc ggatgaatac ttctgaatta atttctgaca    42120
ttttgtaatc tcctgtagtt gataggttta tagtatcacg tctacaggag atgtaaacag    42180
ctttattctt ggaatggggt aagttttcca acagctgaac aaatttctac cagtacaggg    42240
taaaactctt tcacttgttc aaggcgttgg gctgcatact gtacttcacc ttcttcgaga    42300
caagccattt ggtcgtcaag caagtatttg tggtagccag tacaggcttc accaatgata    42360
cgctggaaat cttgtaaact ttcaattttc atcagtattt ttcctcgggt tggaaaacgg    42420
aacgacacgc ccacatgctt gcttctttca gacggtcaat tgcattacga atctgggtga    42480
tgcgttcatg agcctggtcc agttcttgtt cagaaacctc ttcggtatct aagttcatat    42540
aatgagtaac atgttcttct tccagagctt taaaacattaa cccaagacga acttctgcat   42600
ctttaatcgc gttcacttta ccgatttttat cgtcggtatg cggtttataa ccctttatat   42660
```

```
cttcaatcat ttcacttcct cgccagttgc gatatcatat tctactaaac gaaggccatc  42720
atatccacca cgaacagaga tatatgtgct cggataaaca atttctttac cgttccattg  42780
cccaccatcc caacattcca taaagccttg ttcgccctgt tcgtggaacc agtcaacaaa  42840
catcttcaga gcttcatcag agccttcaat tgtcaattta gacatatttc ttccagtcag  42900
aaatcatatg aatctcttgg tcataagtca agagactacg agttataata cccttacaag  42960
gccctgagat gaactcgaga gtgaagtaag gaacctgttt cattaatcgg atgcttgggg  43020
catgacatct aaaacgagag cccttaaagg gccctgtcat gaatacatat tccaatgggt  43080
agaaataagc atattcgaaa tttgcagtaa ggtcctctct tcgaaccta cgtgagaaat  43140 aacagaactc aaaaagttct tcatcagtca tcattgcatt cctatcacaa agaacagagg  43200
acgcgcagtt tgattggttt cgacacatga tgcatgacag caatgttgca ccacctttat  43260
atgggcatca taaatcttat ccatattagg tgttttaaca ggctcatcaa ttatatacag  43320
aacccgtgaa agtgataatc cacggaattt gcatgcagtg ttaccaataa aactacgaac  43380
agaatcagtg tacaaacggt acttaatact ttctgtatgg ctattaaaat attcctttct  43440
gattgcagca gccgaaacat tagcatatgc cgtgttatta gacaaaataa caatagagcc  43500
gccattagct aaccattctg tggcaaaaat ggatactgct ttagttttac cggattggcg  43560
cccgccatca agttttaagg tgcagcattc tttaaacagg gtttgtgaat caggtacata  43620
aaacccacta ttacaaatgt gttctactct agcatcagaa tggtttgcaa aagcattcat  43680
cagggataga taactaccgg ttaaaaacgt tttcataatt gtctcttttt aagttgtggg  43740
gccattcctt ggcacattaa gtcgtccatg tatccgtatg taaacccttt accgcacttg  43800
ggctcgacct tattacaggt agggaaaggt ccatcactca gaggacgcga cgttcatgag  43860
gagagggccg gcttgccttt attagaaaga accagagcct ttaattgtgt tctggcgacc  43920
tttattttcc aattcagagt ggtcgatttc tatatgcttgt gctacaccaa aggccttttt  43980
aactttagct aaagaacctt tagatgtaac aatattaaaa gtattacctt tggtaaaatc  44040
aaccaaatcc acttgtacac cctgcttgcc gaggcttgct acaatagcat caacatattg  44100
ttggtctaaa ttgccttgaa caccaatttg aaatgcctta ggagctttgg cttctgtgat  44160
aaattcttga taagttttca tattattcct taagttgata gaagtattct atcacggatt  44220
taattaagcg taaatagcct tgccataatg tttgtaccag gtaggacgct gtgcaatttt  44280
ttcgtccaaa cgagcctgag atatagcaat agaagcttcg tgtggagtat agtcaccacg  44340
gaattcctga ggaatatcac taatgtcctg gaccgtagtg tccttgatat taaaaccacg  44400
ttttaaacat tcggctataa gctcgatctg acgtttacgt aaaaattcaa gcttatcgta  44460
aaagaatgta acatgacctg taccaaggat aaaagtagga ctgattttga aatcacggac  44520
acgtttacca ttagcaacat gcttacgaac tgcaccgaaa acacgtggta attcacggta  44580
ctcagccatt aagtgttggt cagccaattc agatactaag gtaaggttga tacgagtcat  44640
tttagtgttc tccatgtttg tatgagaaca ctatatcaca gctatcgtaa aagtaaattg  44700
ttatttacct ttaattgctt tagctgcttc gatagccgct tgctgaaggt catccataga  44760
cataccgaac ttagaagcaa agttatcaat tttcttttcg acagaattca aaggcttggc  44820
ctgtttacct tcattagcgc cagggagagc gagaatacgc tctttgtcaa tataaaggct  44880
tacaagtttc ttacggtctt tatctggcaa atcatgaaat gaatgggcct ttttatttac  44940
ggcggcttct aatttacccg cacttactcg cgcttcggtg ataaattctt gataggtttt  45000
```

-continued

```
catatgtttc ctttaaatgt aaataggtcc gagtattcgc tttattaatt accacgggca   45060
gcattagcaa cggcgtaagc gtactgaata ttagcgtctt aaacgtacc tttagaggtg    45120 tctatttctg ccttaaagcc gcctttagcc ataacatcgg caaattcttt acggaaggcc   45180
attgcatcaa gacccttcca tgttgatttg tgcttggcaa attcaagacc ggcgaagttg   45240
accgccttag ccaatttatt atcaatagtc catttacctg ctttaggtac aaatacagga   45300
cctttctgtt tagagaacag ttttaaattc cagcgacgaa ggtcaccgtc agctttaaca   45360
aaagctgcgt ccaagttact agcaacaaca tcttggatat gggcaaattt aagtccatca   45420
gcttcaatat ttaggtcgtt acgccagcga agtccttccc aggcgaaagc tttaaagtcg   45480
gaagcttttg tagccaagta ccgttcaata ggagctgttt tagcgtcaaa accgtttcct   45540
gggttgtcaa cgccgtttcc tttgtaagtc cactcatctt tattaatgcc ttggaccttt   45600
cctacagaag cttcggcgat aaattcttta tacgttttca tacgggttcc ttaaaggtaa   45660
atattttaat tggtctgttc aagtaactgt agatatacta tcacaattct aggagatgta   45720
aacttattta taggtcttca tccaattctt gaacaaagcc gcgacgtctt tctctttaac   45780
gttcagttta atgtccaaca ttttaccacc cgctgctctg gtttggcgaa tcttagcagt   45840
accggtttcg ccattccact caacataata ctgtccagtg ttcattgcaa taccatcacc   45900
gtagtcttca ttttagaag tggtgaatgc tagcttcata gtcttagata cacgagcctg   45960
catgcctgtc tgcagagcgt tacgaacgcg aataacctga ggagtggcct gggtcaagtt   46020
ctcattcagt tcttcagtga actcttcaga ttcaaacatc gccaaaagtt ctttagatgc   46080
aggaattaca ttctctgcga taattcatt ataagttttc atatgctttc caagtacctg   46140
ttttaaatgt tgaaatcacg cgcttagcac gattagggg ttgtttatac caacgggatt    46200
gagccaggtt aactgccgca tcgttccaac gtttctgttg gagcatacgt aaagagttag   46260
tgaaccctgc tacacctgct tcacccattt ggaagaccat gttaattaaa gcacaacgac   46320
gaacttcgtc caatacattg taaacaggtt tcaatttagg attacgcaga atagctctac   46380
gagcattttc aaccgatcgg ttaaagagtt gttcggcttc agccatagta atacgaccat   46440
tacaaactcg gcccataagc ttatcaagtt cagcacgagc aacatcttta gatgggttct   46500
tggtaactaa ctggccaata ccaatagtcc aataaccttc agtgtcttta taaagattta   46560
aatcaagacc ttcgtcttga cgtaacatat caaaaatatc cataataccct cctgagtata   46620 ggaggtattt atatcaaaag agcgaatcta aaaccttaaa catcgactta cccatgacat   46680
attcccattg cggacgttta atcaaggcga acgcatcgaa ttcaggaata gtacgaccat   46740
cagggaatgt atggtaagcc gtacatttgc aatccttgaa ctgctcgtgt tccacaggca   46800
ccgtatataa gaacagatgt agattcttat tgcttgaata tttgaactcg cctaggtctt   46860
tcaggaatgc aggatcgtat gctgtgaatc caatctcttc ttcggtttcg cgcattgccg   46920
cttgaatagg ctcttcgcct ggttcgacat gaccttaggg aatgtcccat ttatgacgca   46980
tgttctctgg attacgagag cctgttacac gacccataac caattcttta tcggcagtca   47040
tgaacaaaat accggcagat agttctttca ctttcttact catcgtctcg ttcccatgat   47100
tgtttaaaga tatctcgtat aataatttca acacacgttt ctgttgacgg actttcacta   47160
tcagatattt ggaccatata atcagaaata ggtcggaaca tatccaagtc gctttctaaa   47220
tcttctttga ttttctcttc tgacgttccg gtatcatagg aatacagata agaatcacat   47280
gactcagatt taatataaat tgcaatactc atttacggca ttccttaata aaagagttta   47340
atgtattttt cttagtgata tcgtcatata ccttttttaac tttagaaata cgaaaaggta   47400
```

```
cttcgataac cgaggtccat aaaaatgatg cgataagacc taagatagca gcagacatcg    47460
ctgaagcgaa tacacaaata ggcaggtcat tatctgttgt caggaaaaac cctaggagtg    47520
ggaaaaataa tatcccatc caaacataga atctagaact caccaatttg tcgtattcat     47580
cactccaggc acggaagccg tattttttgc tataacaaat caatgggtct ggagtttgtt    47640
ctttatgtgg ttccgcttgc cagccgttta cgatatagcc cattttatat tcctcaatta    47700
aaagctgttt catttcggca gtacaacccg accaatctat cgtactagct ggaattcctt    47760
catcaccatc atcaatattt cgccaggact ttttaataac catattctca ccactcggga    47820
taataattcc ggcattttcc gaccgacgga tgaagtttgc atcaatgccc atacaccctg    47880
gttcataaag ggccattacc agccctccat agggaattcc agatatactt gagcattaac    47940
acggatttca ttagtaatct ttttaacacg gtcggtatta cgagacacac gaccaaacca    48000
gcgccaaccg ttacttactg cacgagaacc cgtatgccat gtctgccaat caaactggag    48060
caacgtgcgg tcaggagcat cccacttggt taattcattg gactcaattt tttccagaac    48120
ttctttatgc cactggcgat agataagttc gccttcagga atctggctaa attgcgcagt    48180
tccggttgca aaatgggtag gacacacatc agcgttaaca agaccaagaa tatgttcaga    48240
atggtaacga ggattatcat aatcaggttg ccctgcggta ataaagtgtt ggccaaccgg    48300
aatatccgga cgtggtacat catcatggtg gaagcctgga attgcagggt accagccggg    48360
cattaacatg tgtacacggg aatcaaatac aatatcaggc ccacattgcc aatcttcagg    48420
caggttttca ataaagctac gagtaatagg accaccgtgt ttatgagcaa ataagcatc     48480 acaattaaag aacataggct catttttaat catatcatta ctgatatctt gagcaaaatt    48540
acctactata gaagctttgg aattaaaagt ttttggacca ttcataatat tttcctcact    48600 tacttttgt tgaaaaagta catttacct ttaggggata aggatacacg aagtgcgtta      48660
ccaataccaa ctgaacattt aaccaggtca gcagatttta attcaccgaa tgcttgacga    48720
aggtcaccgt cacgagtgtt aaccatcagg catttagcac cagctgcacg aacttcgttt    48780
aacatgttga ttgcttggtt agaaagtttc attttattct ccatttcact ctgttgtttt    48840
gataggtcta tagtatcaca cctatagacc ttgtaaacaa ttttatgcaa ttattttcg     48900 aaaggacgaa ttaaatgttg gttacgctta aaccgttcaa tgtagtcgtt ttcacctaaa    48960
gtcttgtaca tattaaccac agcttggtag tttcccagg cgtactcacg gaaccaacct     49020
gaagtgattg aggtgcacac tttctcaaga gccatataga aacttaatga tggtgaaata    49080
ttgaagtcat taggaacctg tgaacgttct agtgccagga cacaagtttc ttcatacaca    49140
ccagctaatt taatagcttc aggcaaagct tcaaacttct cacgagaagt catgacttca    49200
gaaccttcct tcatataaaa ggtatatgca gggcgtcctg ccaatgctac tgcttcgtgg    49260
atggagtcat ggtccagcgt ataaatggta tcattaaaga atgatgattt gttaacgtct    49320
aatttagggt gagaatagct caacgtttct ttttgacgtt gcagcataat ttcctggagt    49380
tcttcgttca gggtcacgcc tttattacga aggtatttga tgtgggacat agttttcaag    49440
aagaacggat tattcttcag gaaacgatga gaggttttga tagccagaca gatatcaggg    49500
gttgcccaat agaaaccagt aagacggtcc tttttaatat gattttcagc atatttcagg    49560
agacgatagc ttgaggtgta gtcttcatct tggagctcac cagtgatttc tcgtacgtta    49620
gtcagggcac ggacgatata agcttcgaaa taggtttctt tgccgttgta catgcattta    49680
aaagcctgga catcagggtt atccacagga acatgagcac cgaacatacg tgctttaaag    49740
```

```
tggttccatg agccttggtc ggcaatgaaa tcccaatcag aatttttgat atacttattt   49800
tcaatcagac cagcgtggtg cagtgcacga gaaccaataa ctaacatcat aatattttcc   49860
tcagtaaact taaatttcag caacgtaagt gttatgcaat tcccacatat catcggaatt   49920
actctcaacg ataggaatta tctcattaga aatttcttct gcataagggt cgttgataca   49980
gtgggcatct tcaaaacgaa caccgtaatc agacttctta taagcaaagc cataaatctt   50040
tttaaacctg gcacgagtaa tgcgtaccgg ttcattagac ttatcggaca tcggagcata   50100
ataccacata tgttctcctc atgtttgtgt agggtaatag taacacgtat ttttagagtt   50160
gtacatcact tctgcaatat tctaaaaata atttatcgtt gtctactgta tcccaacgac   50220
gccaagatgg gttccagacc aaagcgttgt caccacaatc attgagctta aaatggtcgt   50280
agtacatagc tatacgtcta gtttcgtcac cagagaaccc cagtataggc tcgccatggg   50340
tgtgatacat atgatggtgc attgagaggt cgcatttgta aaacatctca cgtttaccac   50400
gaacgaacaa gaaggcttgc ccattcatat agaattcttt atctgttttc aaagatatt    50460 tgaatactga atctttatgc ataagtcctc ctaccacatc catgtggtta aattattttc   50520
ctaacgaaac acgagtaggt ttttaccaa aatagtcttc gtaagaacca tctaaacggc    50580
ccgctttaga ccgacaatat gaatcgtact ttttgtaata agtcatctca gtattataac   50640
gtgggtgtct atcggccata ataatactta gtggccaacc tttggcataa tcgcgaagac   50700
tgtttatttt acgaatgtat cgttttttca attttagcat gagcttgggt accagatttt   50760
accatcggca cgagcaacga aggtacgacc agcttcttcg ccataacaag agctattcag   50820
ccaatcttcg agacgaactt caccgtcata atcgtcgagc tcaacaccaa aatcctgagc   50880
agaagccata tcttttactt tcttatacag tgcagccagt tcaagtgccg cttttttctaa  50940 ttcattaata tcagacattt ttatttcctt agcaagacat agaagaagta aaccagaaac   51000
catcaccatc aggaatgccg taatcatcac ggacccattc gtaatcatca tattccgggt   51060
tctttggaga aatgtattgt ccacgaccag aaacatggaa ctcttcacct gtttcgtcag   51120
ccacggactg gcctttacgt actaattcac ggatttgttt ttcaatttca tcaatagtca   51180
ttttatttcc ttagcattcg taagaggagg acacccaaga ggtaccacta atagtaatac   51240
aaccgttata aagcgtgata tgacgttcca ggtcacgagc gccatcgata tagatatcag   51300
cttcttcgcg ttcttcttta caaatctgga taacgttttc aatagctgcg gctgcagtac   51360
ggattgcaca atctagttca cgagacataa taattcctta acattcagaa gaagaggata   51420
cccatccacc atttttctagg ctggtagtgt aatcatgttg gtttacaata gcgtactgag   51480
cttcaccgta ttcttcccag tgggcaaggt cggctttcag ggcgccagga gaataatagt   51540
caccgcccat accgcgagca gggtatatat taaaatgagt ctcatatttg ttagcaattt   51600
cctcagcacg acgaatagct ttatgaatat catttactgc ttcagccagt tctttatttt   51660
tatggtaatc attcatcata gcgtttcctt agcacattgc cgaagaggag acccaagcac   51720
caactgtaac gacaccgttt tcaacttcac cgccattgtt ttcaatttca tctttaaacc   51780
actgggagca ttcataaccg acaggataat atgtacggcc tgaaccataa tcaccggtgc   51840
cgaattggat accatactta tcggcaatag cttcgcattc atgttcgatg gcatctactt   51900
tattcagaag agcatagata gccttttctg cagacagcgc gctgttgtat tcagggattt   51960
caatttcaat tttattcatg atttacattc cttaataaag gtttcaaggt cattacgttt   52020
agtttgtttt acatactcat tataattagc catctctaaa gcatatctct tacggatggg   52080
agcattcaaa gcgtttgtat ggcaaatatc atacacaaca gggataaaat aagccacgac   52140
```

```
agcaggagcg attatcatat agaaacccat ctcaataggc atgattcctt cgattgccgc   52200
cataaccgtg gtcattacca gaccaaccag accaccgagc ataccggtcg caattcccat   52260
aaataaggaa atagcaatat catattcagc caattgataa acatgtgatg aaagactagg   52320
ccgttccatt ttgaacctct ttagcgtatt cacggcattc agcaataaaa cgattaagct   52380
tccgttgttg tttacgactt tctaatgtgt actcagtagt taagatacca agctcggctt   52440
tatcataatt tttaatatca gagtaagatg ggcgacggtc aaccattcca aatacatcac   52500
cattttctaa agctacatag catactaaat ggtaatcatc gtctgccata ttaagaagca   52560
cacaatcagc gctctcgttt aaagaatata ctgaataacg tagtccagcg aattccactc   52620
gttgaatagc cagatttacg tcaataattt ccaaagcatc ttcaaaagaa aggtcttcag   52680
ctaaagcaaa aataaaaggt aatttggtag tatcgccacg gctagatgtt ctgcttaaga   52740
aatcgtttga atagcctagg tcttggcgaa ttctataaag aactgaattg gtttcatggg   52800
aaagaccact atttttaaac caatcaatat ttgatataag gttatcatat aaactcataa   52860
tattctcctc tcctccaaat agggagaccg aagtctcccg gtaacattac ttaagtgaat   52920
taatgtagtc ttcgatatca gcagaagtcg tatccattcc aacttgcggg cctttaaacg   52980
tttctacacg catcagggtg tcttcaatat caatcttagt cagtgcagcg atttcaacaa   53040
catcatcggc agtagcaata cccagggcag ccatattacg agtttcacga atgtactcaa   53100
gcttaaccgc tagttcctgg cgagagtcat caagttcctt gaccttaagc ttaatttcat   53160
tacgcatttc aacataatca tcggctttct tacgaagttg agtagctgta cgacgataaa   53220
ggagacccag tttagcatgt acctggacat cagcgccttc ggcaatcagt ttacgaattt   53280
cacgttcttt agaagcagcg agctggtctt tttcattagc caatgcacga atacgttttt   53340
cttcattcac agacttaaca tgagcagtct ggagttcagt gatttatca atcagagtag   53400 aagcagcttt ggtgtattgg tcttcgattg acaggttctg agccattgcg gtgcccagtt   53460
tagaacgaat gaattcaacg atttctttta aagtgttcat agtatttcct tcagttggtt   53520
aacgttttgt aatccatgag gacattatac cctgtcctct gaggtttgta acatttttat   53580 ttcattttg cgaggcaaat ttcattggct tcccattgag cttgcttaat aatagctttg   53640
gatacaggag cccttggcc ataagttttt gacgttgaga gaacaatatg tttgtttgct   53700
tcattatgcc agcccatga ttttcgccg tgagtacctt taactacagc tgacacctca   53760
acagagcaac caccatcaga aatcttggtt tcgacaaccc attcatttct ctcagcagct   53820
tcaatttcta atctagtttt ttcttcatac atcgcggccc aatcagtttt tgccaagttg   53880
aaagtaagag ctttctctag ttctttggca tattttgtt gttcaggtgt taatgaatta   53940
tacaactctt gcatttcttt atcttcgata ttcattatgt tctcctcaaa ttatgggctc   54000
ataatatctt aatcatgagc ccgtgtaaac gttttatttc atattattga ataattttc   54060 tgcatcaaaa tcattaccat ggtaaacttt ggtagacgat ttggcgtaac cttcagctga   54120
gaacatatta atcacaactt taattgtata ccactgtcca tcttcattac ccattactgc   54180
ataggtttca tacaccgggt gttcaggacc gataacttta atatcgttaa cagtagcacc   54240
aaattcttca ggaacgcatt tcataaagaa attaaacact tcaccataat tatccatttt   54300
actctccttc acactgttgt tttgataggt ctatagtatc atgttctacg aaagagtaaa   54360
catctttttt aaactttta gaaacaaaaa aaggcccaac ctttcggaag ggcctagaat   54420
cagttcttgt agaaccggaa tgggtttatg tggaaggcta acatagcctt agggatttta   54480
```

```
cgagacaaaa gactcttaag tttccaacca cagtatacac gaaggtaaaa ggtaatccca    54540
cctactttaa gatacggaac tgaagcaaag actccccatg cttcgtcatt ccacatccat    54600
aaccatccat gatgagcttt atcaggagaa ccggatttaa cgtcaggatt accacgataa    54660
tggaattctg agctacaatc gcgtccaagt ttatggtaag caaagttata agctttattt    54720
cgccatagcc aagctaccct ctggagataa acaccgcccg gcattttcct gattttagcc    54780
caacgtttaa tatgaccttt gtcaccgtca attggattat cgtatgtcat catccaatca    54840
aagccataag gcaatttacc ggtctttta ttatggaaag gaactacaaa aggcgcaagg     54900
ataacggcca gaaccataga gatgaaatcc agtggaacca acagaaccca actcaaatat    54960
tttaaaagtt tcatatattt ctctaagtta accaaaaaag ccccagacgg ggctttcgtt    55020
atttgatttg tttagcagac cagatacggt ctttgatgat tttctgaata tcttcaacat    55080
actctaagtc gtgagcatgt ggattatctt tgaagctatg tgctcgtgcc agtttctggc    55140
cttctgtttt gattactaaa agctctttaa gaattgcttc atacttagaa ataattcctt    55200
tggcgatatt ttttcttga gcggcttag gtccgctttt tgacgcaggt gctttacctg      55260
tagctttctg gaacaattca cctgatgcag ctaggctttt aaaaactcgg ctaacagtat    55320
tggcattagt aaaaccttcg gctttaaaat ctttaataaa acggaaacgt tcttcatcag    55380
aggcgtcttt gtaagaatat ttacctgctt gaattgctgc aatcgcagcg gctttacat    55440 ctgaactaga ttgttcagtc aaaaattcat tgtaagtttt cattattatt tcctaagtta    55500
attaacttat ctatttatta tgccaaaaag ccccaacctt tcggaagggg ctatgccttg    55560
cggcaaccct gtcggggttc cacctgctag gcaagtgttt gtacgaaacg ccaggattcg    55620
aacccggtta ttaagtagtt gacgctactc aatatttta aaaggccata tctcgaccat     55680
atccgaacgt tccgtcaaaa acgctactcg gcttacggca aagatatttc ctcgaatcga    55740
taattctgtg cgccgtttct gctgtgatgt aaggggacat caacaaatca taaagattta    55800
ttaatgtcag tccttaaaca gggaacatca gtccgacgac ttaccggtag cgacccggtt    55860
tcttgtttgt tgcgccggtg aatgctggta atcagtcttc atacgacggc ttgactatat    55920
aatagtcttc atttggtatc ccgccctggg atcgaaccag gaccgcaaac ttagaaggat    55980
cgtatgctat ccattacacc agcgggacgt agttggtgac ccagaccaga tttgaactgg    56040
taacctttcc cttatgaggg gactgctgct aaccattgag ctacagggcc ttaaatcaaa    56100
ctacaaatcc agcaggagca ttatcatctt taatcatatg ctgaattgta tgataagtca    56160
tttcttctgg agcaaccaaa taggctgcga cgttaaccag tggaattctt ttgggcttag    56220
tgaatgtgga atccgctatt gacataaagg ctttgccgtc tcgttcaact tcaccaaatt    56280
gacattcata tgaaatagaa caacgttggg tagtggttgt cttggttgcc gggtcataaa    56340
aagctaattt taatactaac ataaacacct caaataaaat taagtaaagt aagtttgatt    56400
aatagacctt gtctattatg aaaggctctt tgagggaaga accttggta ataggggtt      56460 acttaataat gttagagtaa taatatcaca ttactcttaa agcatattac tatttttagg    56520
aatagtctgg tcaaatttga ttcattgtgg ccacatatta atgtaatcaa gtttaataga    56580
agcaatcttc aaaggatttt taaagatgtc gtattcgatc aatccgtttt cagttgcggt    56640
gtagaaagta agttaacag aattataacg gcgaccatta actttagtt taacgtcgct      56700 tgaactacgg ccaatattaa cctgttggac atcaagcaca gcacctttgc caaagttgcg    56760
aatcagtagc tctgctgcaa cctggtctga attatatcca ttctctggat tagtaacctt    56820
aacgtataac atttaaccct cgtctacaat agtatgggta ttggcattaa caatctgcca    56880
```

-continued

```
ccagtcaaaa cgatcggagc cgtaacgagg cttttctca ttttcgttaa taatatcacg   56940
tagttcgtct tcagaaaatg ctttagcgat taaatcggta tagccaccac gtgggtaata   57000
gttgtcacct gcgaacagaa ggaaatttac tttaccagaa ggaacatatg cttccttagg   57060
atacttgttt cctgcttggt ctaccacttc aatataacgg taaggaatat cggtactttc   57120
aacccattgc caagctgcag caggggattc aaaagcatct acacctaaac ggttatcttc   57180
atctttagac ggattatttt cataatccgc atatacataa tattcaatgt tcattattca   57240
cctttagaga ttttatccat aacgaaagaa attgaaccaa ttaagaatgc cactactaaa   57300
gagattatat tctcggaagt tgaaagcata tcgagcatga atcctgcaaa catactaaag   57360
ccaaaagcag taacagcggc cagtgcagta acatttctaa ttaattcaca acgtttcatt   57420
ttattctcca atcactcatt tgttttgata gggctatagt accatcacta aagcccgttg   57480
taaacaatta ttttaaataa attgcatact ttttataacc ggctgtttcg tgacgtagcc   57540
cttttcatt agcaaaacgt tcaatattgt taatttgatt ctggtcaagt tctgaagtat   57600
caaatacaaa aaagtttcgc ttattgccta agttacgtg attagtcaaa tcgatgttat   57660
agagatgatt tatattatca atcatggtct taacagattt gttaatttt acttcttcat   57720
taagaataga ttcagcgata aattcttggt atgatttcat tttattcagc accagcggct   57780
ttcaaaagtt ttttaagatt ggcagtgcct tgagcagaaa atgtgacttt gccgtctttt   57840
tcgccgatgc tcccggtcaa tttagcgagc ttatcactag gactttttt aaaatcagcc   57900
aatgtaccgt caaggttttt tgtaacaacc ggcagttggt cttcttgttt tttagcttcg   57960
gtaataaatt cttgataagt tttcatttt atttccatgt ggttagtttg ttttgatagg   58020
tctatagtat catgcctata gaccttgtaa acaactttt taaattattt tagccatgaa   58080
gaattttcag agacccagct atctatatct gattgtgggc caaagaagta ggcaacccca   58140
ttagataact ctcctgaaag ccaatttata cctttcaggc tttctttaaa ttcttcagga   58200
gtacaagaaa cctctattgc caccgaagag gctggttcca ttgcttccgt taagaattcg   58260
ttgtaggttt tcatttaaa tcctcggccc agtcgagctt caaggttct ttatattctc   58320
tgtctaaaac aacaggaatc tggacatctc cactaaaggt aagaggtcct acattataag   58380
acaatgtgat atgaggggta taatcatcaa atcgtgcgt agcacctaag gtacgagcat   58440
actgatggcg gcatttaaga tactctgaat tgagaaccaa taccaggaca ggagaatcac   58500
cgtgtttcca cacttcaaga tgtcctgacg aagcaacttc aaaacttccg gatgcaacgg   58560
tgtatgaac gttgactctt gaatagcaga ttgtagaatg gaatttttca cgaggaactg   58620
gattaggaac ctttaaagtg cgctgaaggt tttccagcgc atctaaagtt aattcagaga   58680
attttgcagc aacgtataga ccttgagcaa atcttcggt tttcattatt cttcgtcaga   58740
agcttctgga accagggcat taacggcatc gatgatatca tcaattttaa tctgctcgcc   58800
ttcaatacca actgcgtggc agattttacc aagggcttcc tgaaggatac gagattcctg   58860
ctgcgcctga gcaacagcat cctgggtatc aagaatacgg gatttcagaa gaacgatttc   58920
ggactgcagt ttctgttcgg tagtttgttc agacattttt atttcctaat aatttatcaa   58980
tagtagtgta tagttcagaa agagtgccgt tattttcaac aacaacgtca ccaggtaaaa   59040
ttggcagacc cgcttcagtg atgtgcgagt cttgtacttg accggtttca gagcgaacta   59100
catgaataat cgtagcaccc atcgctctga gcgaatcaat ttcatgtgtt tgacgaacat   59160
caggtacgac atagtatttc gcatcagagt atattttatc aaaatagtct aaagcgaaca   59220
```

```
acttaaccca atacatctta tcaaattggt taacaataat atcagtccca agggtctgca    59280
tgagacgacg tactgaccaa ttgttatttt tatttattac ttcaaacagt tggtcttttg    59340
tttcttcaga cagatactgg actggggtaa gaccataatg atatgcggta cgaacatcca    59400
ttcctggaat aggaaggata ttattcagtt tgacaatagc attttcaaag atatcaatca    59460
catcatatgg ttttaaagga aggatttctt cacggtcgta accgatacct tcaaaacagt    59520
tgaaatccag tttaggcata taactacggt cgaatacagg gtcatcagag atgtattcat    59580
aggcttcagc cagatacttt ttaataggac ctgcgagctg aaattttacc gaatccatat    59640
tttcgattac atagttagca acggtatcct taccgctacg tttgattcct acaattgata    59700
ttagtttcat tattttctca tagatggatg catagacata cgagccacac gttgttcggc    59760
atacgaatca atttgtggac gacctgtaac tattgtacca tctatttcta cagcaaacga    59820
tttgaagttg aatgttgctg tggcgattat tgctgggtca gaatcctctt tataagagta    59880
ctggatttcc gagaggtcag atggccaacc gccatagtaa tgaatgctca ttacgatttt    59940
ctgtttgtta ttatcaagga tatggagcgt aattgcttca ggtaagcctt taggatgcca    60000
agcttcggat tcatgggtta cgtagttgtt taatgacaac atccacttat aaacgtcaag    60060
ccatgatttc aattcacggt ctacaagaaa gttcacgatc aatgggtcga attctacagt    60120
agaacctggc agcttagcac gatgtatgcc ctgggtcgat cctgggacgt ctgagatcgg    60180
aatatggata ccgggtagtg ttacatcttg tacgttcaat ttgaatgact gtgtcattcc    60240
tgagtcacta acctctaaga taaagttggt ggtgttagtt tggttaaata aaccgttcat    60300
aaggttccta tattgcttaa gtcccagaca gtgtataatg gtcctaggtc tgttccattc    60360
aataactggc tgggataata gattatgaat tcttccatac tttctgagcc gagtaacgct    60420
tgcctttaga catgaattgc tgaagtggaa gcatgaccac attggcccaa tcagatggtt    60480
ttatctctac taaaggtccc ttaatatttc cagggatata agccttaatc atcacgtctg    60540
caccagcgaa tcctttttacc ttactccaat cgattttttaa tttagtcgag ttagtaatgg    60600
taggcgtact cgcgtattgc ttcagcaatt cttccagaaa ttgttggcgt gctttaggcg    60660
ggatatagtg taagttcagc ccgtacatta aattatgctt acctaaccca agataaatga    60720
ttaaaggata tttgtcccag tacggtaggg tatccttgtg tttagcgtca tagatataag    60780
cataaagctt accaggagat ggtttagata cctggtgtcc acgaattcct ttctttaatg    60840
tttctgtaaa ccatttagct gatttattat ttacagcagc gccttcgtta gcaatcttat    60900
cacgaatact ctttctaaaa ctattcacca aaattaattg acgttcggct ttggttaatt    60960
tattgccagg tttattctga agtttttcaa cctgtacagc agttttaatt cggctcgagt    61020
atcgagacat cgcagatgta aagctagaat acttgatgcc tttatcttca gcgaatttct    61080
tagccgagac acctttagcc ttagcgttgg catattcaac gcctaaagtt atccattgtt    61140
gttctgaacg agtgggcttg gaaccttttg tggtttcagt agcctcattg atgtaggaaa    61200
atatactcat cctttccatc ctaatttttt cagtgaatgt tcggtaatca atctaaaggt    61260
gatacccatt ttatctgctg tagatttagc tgcttttccac ttatcggtat taacggacca    61320
agtataatgt tcgttgatat atctctttt agcagccgta gtcattttaa caggcaccgc    61380
aggagcatgg gtttctttaa aaggtttgac ttcaaaaaag aattgttgac ctgtatcaaa    61440
tttaacccag aagtccataa aatatcgtct tttctttcct tcagcattgc aaaagtaagg    61500
aatgactacc tcttccgaat tccactggac tacattaggg tggttgtcaa gccaacgcat    61560
aaaccatgct tcccaagagg aacgatattg gattttcttc cagtcacctt tatattttg    61620
```

```
taagtttgta ggtttaaatt tccctgagta agccatagtc gcctccttat aaatattaat   61680
attatttata ctcggaggcc ctatgctctt ctcattttc gatcctatcg attacgaatc    61740
aaaaacagtc aagccagatt ccggctcatt aacaaatgcc gatgtactga gcgtgccgat   61800
gactgatata tttagaaatt ataaagaata tttcgataaa gtggctaaaa attatacact   61860
aaagacttat tatatcaatg gggcccctcg tccagaagaa ttggctaatc aactttatgg   61920
caacgtccaa ttatattggg ttttattgat gtgcaataat acatatgacc cctattacgg   61980
gtggattaca ggtcaagaag ttgcatatca agcggcaatc caaagatatt ctactgcagg   62040
cggtaatcaa gttctttatc atgttaatga aaagggtgag aaattctgga atcttgttaa   62100
cactccagaa aacccgtata cttggtatga taaaggcgat acagaaaaac gctatcctca   62160
atatgagggc cctttggctg cagtagatat ttacgaggat gctattcgta aaaatgaata   62220
taagcgcgaa ataaagattg tagaccctaa tgatattgag tcctttattt ctgcccttat   62280
tcgcgaaatg gagaaagccc tctaatgatt aacatgtctg ataatgtaag ttggttcgtc   62340
ggtgtagttg aagaccgaat ggacccgctc aaacaaggcc gagtacgcgt gcgcgtatgg   62400
ggtatgcatc cctatgaaaa ggtacaaggc cctgtaaaag gtcttcgtac agaagattta   62460
ccatggatgt cggtattaat gcctacatct tctgcctctg tttctggtat acaaaccgct   62520
atgactggta tggtccctgg tacacaagtt tatggccact ttcttgataa gtggaaatta   62580
aacggactcg tccttggtac atacggttcc gcttcaaaac aaaaagcaaa ccctaatgaa   62640
ggctttagtg acccgacagg tcaatatcca ctttatttag gtaatgatgc cgctgcacta   62700
aaccgaggtg gtgaagttgg atatgatgcc acttctaacg taatacaaga tgcaaacact   62760
gatgtaggta ttaatcctga tggtttagat ttaagtcaag tcaaacctga tgataatcct   62820
aatttcacaa tagaaaacat gcttcatcgt gatgaagggc ttagactgaa ggtatattgg   62880
gacaccgaag gatatcctac tataggtata ggccaccta ttacgccaca acctattaga    62940
gatatgggtc ggataaacaa aatattatct aatcaggtag gacgagaagt taaaggtaac   63000
cctggtgcaa tatcaatgga tgaggcttct aaattattcc aagaagacct taaaaaagtc   63060
caaaacgata taggtaggca tagtgttgtg ggtcctgttt acaataaaga aaaccgttca   63120
agacaaatgg ctcttgaaaa catggctttc caaatggggt taggcgggct tgctaaattc   63180
cgtggaatgc ttagtgcaat gttaataggc gattataaaa aggcatttga agaagcccgt   63240
aattcagtgt ggtttaacca aactaaagga cgtgcatcaa gggtatcaat gattatcctt   63300
acaggtaata tggaatcata cggtattatg gccccaaaag aaaggtcatt taagggcgt    63360 tcgtatagaa tgattcaaac ctttgctgct cctgcaaatt cagacccttc cgacccatgg   63420
actccagaag acacaaggat tctttttaaa gaacctgatt ctagttataa aggtaatac    63480 ccgtatgtcc aaaccatgca gactgaaggt ggacacgtcc aagaatttga taacacccca   63540
gggcaagaac gttatcgttt aatccatcct acaggtagtt atgaagaagt tgctcctgac   63600
ggacgtaaaa cttctaagac ggtagccgat ggatattata tgacccaagg cgattctaat   63660
acttatgttg gtggtaataa taaagtcaat ataggtggtg atgaaacata ttataatatg   63720
gcaaacgtac gccgtcaaac tgacgggtcc gaaagcatcc atattcgcgg taatgaaact   63780
aaaactgtag aaggtgatgg gacccttatt gttaaaggga acgttacagt tattgtcgag   63840
ggtaatgctg atataactgt taaaggtgat gcaaaaacat tagttgaagg caaccatgac   63900
tatacagtaa atggaaacgt taaatggtct gtaaatggaa acgttgatat gactgttgca   63960
```

```
ggcaattggt ccgagactat ggcttcaatg agttctattg catctggaca atatactatt    64020
gatggtagcc gtgtggatgt ggggttataa tgaatttagt ttataaaatg acctttgaat    64080
ctcgtcttaa aaataaaact cctccctatt attatgtagg gagtaaaact aattgttttt    64140
tcgatggtaa gaatataata gatgaagatg gaaaaattta taaaacttct agtaaagtta    64200
aggaacttaa ggattcgttt ttattagaat ctcctaaaat agaaatactt tatttccaat    64260
tagtaggatt tgaaagtatt accgagatag aagagaaatt tcaaagagct atagatttag    64320
aaagttggca caacgaatat tttaacttgt catatgctaa tggcgaattt acaacatatg    64380
gtaagatttg gactgttaaa gaaaaatccg aaatgtcttc tataatgaaa gatagcgaag    64440
cccataaaaa aggccgtgtc gttataagtt ttaaaaatac aggtcgcaaa ttatccaagg    64500
aagattctat acgaaaatcc gatttgatga aagctctatg gtctgatatt gaatataaag    64560
aacgcctttc aaaagcccac tcaaagcctt tatcaacatc acataaggaa agtatacaat    64620
ttgcatggaa aaacgaatct ttaagggcgg aaaagggtaa agtaacaaag aaaaattcta    64680
ggtctaaagg cgtttggata tatgctaatg aaatttacaa agttttttaaa gaaaacccctt    64740 ctataggaga acccacattt agaaagacct gtgtaagctt gggattacct gatagtagtt    64800
atgtcgccat taggcgagct ttttctaata acgattttga atttcttgat gtggagattt    64860
acaatggcta atatcctacc tatgagcact gatttaggag actccataga aggagctagt    64920
atagatatat ttttttacagc tcaattagaa acaaacgaaa cattagtcga aataaatata    64980
actgaatatg aggccacccc tggcattatt gtcgatggcg cccatttata tggaacctac    65040
gaatcggtat ttggattctc tgaggatgca ttaaaatacc gattaaacga cgaatttaaa    65100
actgccggtt catggaaaga tttgccagag gacgagagca ctcaattgta cctctggaaa    65160 gccccctagca atctccagaa gaccttttct tatactgtca cattaatcta tgactttcag    65220
gaagagacgt caggaggtga tacagggaac tcaggcggta gtaactctag agctggcgca    65280
gaaaccgacc cacctcccgc tcctgtaaga aaaacccctta ctaaggttta taccaaggtt    65340
atagtgggta attggagcaa atgggctaat caattaagag aatatgtata tgcgaggcca    65400
taatgtcagg cttaagttac aaccaatgcg taacggcagg tcatgaagca tggcctccta    65460
cagtaataaa tgccacccaa ggtaaagtat ttacaggtgg tattcctgta ttagttgcag    65520
gagaccctat tacagaacat acagaaatta aaaaaccata tgaaacccac ggtgggtaa    65580 cccaacctag aacatcaaag gtatatgtta caggcaaaaa ggctgtccag atggcagacc    65640
ctatttcatg cggagataca gtcgcacaag cctcatccaa agtattcata aaataggaat    65700
taaaatggct actcctacga attaccaatt aacaagaacc gttaacgcta tcccaaaagt    65760
atttgtggga gctacgtttg aagaaattaa aaagaatatt atagactggc tttctagcca    65820
ggacgaattt aaggattatg atttcgttgg ttctcgaatg aatatcctta ttgatatgct    65880
tgcttataat acccttttata tgcaacagtt tgctaacacc gctttatacg aatctttat    65940 aggaacagca aaccttcgtt cttcggttgt ccaggctgca caggataacg gatatcttcc    66000
tagttctaaa tcagcggcaa aaactaccgt aatgcttacg tgtactcaag cccttaatga    66060 aaaaatatt cgtattccaa gaggtactaa attcctggct tatgcccgtg atacgtccgc    66120
cgacccatat tcttttgtga caactgataa cgttattgca gtgcgagacg ttaataatca    66180
gtattggcct attgtttctc tggctcaagg acgtattatt cgtaccgaac ttaaatacga    66240
ccctaaaact cctattctta ttcgtgaccc ggatattgat agacaagaag ttaaacttta    66300
tgttgatggc gcagaatgga ttaactggac caataaatca atggttcacg ctggtagcac    66360
```

```
ctctaccatt tactatatgc gcgaaaccgt agatggtaat actgaattct tctttggtga    66420
gggtgaagcc gagaaatctg ttgcaggcgg agtattagaa gctaattata tcggcggtct    66480
aaaacctgtt aaagattcta ccattgttat agaataccTt cgtacagatg gcgaagttgc    66540
aaacggtgct gtcgacttca gttatgccga ctccttggct tatattactg tagaaaaaat    66600
tactgaaaac tataacgatg accctgatta tgttggtgcc gatggtgggg gtgaccctga    66660
agatattgaa cgtattcgcg aattggctgt agttaagcgt gaagcccaga tgcgtgctgt    66720
aacaggaacc gactacgata cattcgtgtc cgagcgtttt ggttctattg tacaagcagt    66780
acaaaccttt acagacccaa ataaacccgg ttatgctttt gtcaccatta aacctaaatc    66840
agggttatat ttgacggcag tacaacgtga agacgttcag aactatctaa aagaatttaa    66900
cttagcccct attaccgctt ctgttatttc tcctgattat ttgttcttaa agcataaaat    66960
taaggtatcg tatgccttga ataaattaca ggaatctgaa cagtggctat cggctcaaat    67020
tctttctcag atagaccgtt attatattaa cgaagtagaa attttttaacc atggattcgc    67080 taagtcaaaa atgctgactt atattgataa tgccgaccat agtatttag gctcctctgc    67140 taccataaca atggttcgtg aggtattgaa cttttTcaaa accCctgaat caggtattaa    67200
atactataat caatacacta accgttctgt ggtttctagt gaatttgagt tgtccctac    67260 tatcgtttct gaagacagtc cggcgtataa tgtcagaatt gccgctacag ataaagacga    67320
acgtggtgat ggtaaaatgg ttattggtcc tttccgtcca ggagatgtaa ttgaaaacca    67380
atatattaaa ccatatacag gaaatgactt tgataaaatg cctgctcctg cggaccaatc    67440
cgtttattac gttataggtg aaattgatta ttattcagat ttcatttTct gggacattgc    67500
ggctattggc ttgacctccg atcgttttga agtccaatct attgaacttt atgcaggtcc    67560
tggccaagat aacgtctttg ctaaagacgg tactttaatc gtatttgaag atgacctacg    67620
ccctcaatac actaccattg aattagaacc tattacaata taagcctctt cggaggcttt    67680
gaggagattt aatgtctgta caagcgcctt cagttactag tctgagaatc gataaactct    67740
cggctaacca cgttagcatt ctctgggatg acgtaggcgc caatttctat tatttcgtag    67800
aactggccca aaccaaagat gcaggtgaaa ctatacctga tgataagtta ttttggagaa    67860
acttaggtta taccccggac aataactggt tcgaggaaag atttatatct cctaattcgt    67920
tttataaaat gcgtgtagca gttgcggccc aaggctttga acagtctgaa tgggaataca    67980
ccgaagaatt tgaaacattt tctactaacg catataccTt cgagcatatg cgtgaattta    68040
ctttatccaa taaattcatt gaagaaaaat ttactaaaaa taaccagagt tacgtggatt    68100
ttaatagtga tgccattatg gcttctatga tgaccgaaga ttttacttgg actccggcat    68160
attcacacct ttcttcaatt tccaattatg tattaaaggc cgaccgcttc cacgagattc    68220
aaggaagtat ccaagccgtt tgtaaagacc ctaatcgttc tattttaatg gaacttggtg    68280
gggtgcTTta cctTtTagaa cgattccaga acacggccaa ggtatctaat gacaaggccc    68340
agaactggca ttatatccgt ttgtttaatg atagagtagg taatccggtt tcacgtacgg    68400
ctcattatca aacagacaca acaacttatg ttctaggtta cgaccgtata ttttacggac    68460
gtaaatcaag tgatattcgt tggtctgctg atgatgtacg ttttagctca caagacgtga    68520
catttgccaa aattggtagt gatatcgacc tggacttcga aatcgaaata tttggttctt    68580
atgcccgttt accattagct atttctacta tcgcagaagc tatgtgtgct tcggatgatt    68640
ttatttacgt tgcggctcgt gacagagttt ataaagcaaa aactactgat gccCctattg    68700
```

```
acaccgaccc gggctctcct acttacggtg agaaaatatt tgaaagtggc tattcgacca  68760
taaccggtaa ccctaaagca gtttgttata aattggattc tatccaagga aatacctttg  68820
ccttaattac gggtgaagtt aaagaagaaa gaatggaccc tactaaagaa gaaaacgtgg  68880
ttgattctga atctaaaggt gtttattggt tggatgtcga aactgataca tggacccgag  68940
tatttggtaa tactgaagaa gagagacgtc gtattgagca tgggtatact agcatgtcta  69000
ccgacggcga agaaatattc tttagttcca gtaacttcaa atatgaagta gaagttgata  69060
acgaattacc tttagaatac cctattgtgg cctcagcggt aaaatatgtt aaggatgaac  69120
agtggattca tgataaacac tatctgatga tgagctttag agctaacagt aaatcagatt  69180
ttaaagaatt caaacccggt cgaatggcct attatgctga accgttcttt agttggtcta  69240
gacgcgatgg gacccgttct tggattacca caagtaatca tgcaatggtt gtttataatg  69300
acgcattata tcagaaaatt attgatttaa acagcggttc ttctcctgaa cgtattatcc  69360
gtgaaatttg ggataaaggc ttttgtaccg taacatgccc taatatcgaa ttcaatggat  69420
ttaaaaaata ctcttcaggt ataatgattc acaaatcatc aggtgaattg gttggatatt  69480
tcgagttcga ctaccgagtt cgagatgaag tccgtgttat ttggaagcct aaagaaataa  69540
tgtttacggc tgaacttcaa aaccaagagc atgaaattcc atggacccct aaagaggaaa  69600
ccggtgaaca agaccctgat ttgcgtcctt tattagttaa aatggttcct gatagttatt  69660
tgcttcaaga ttctaacttt gaaaaattct gcgaatatta cctccagttt attagtgatg  69720
gctccggcac ccattataat aatctattaa atcttattcg taaccaatac cctagagaag  69780
aagatgcgtg ggaatactta tggtctgaaa tctataaacg caatatctat ttgtctaaag  69840
aaaaacgcga cgaagtagtt cgtttcttcc aagcaagaca atcggatttc tggtctacaa  69900
aaggtaccga agcttcatat aaattcctgt ttaaattgct ttataacgaa gatgttgaaa  69960
ttgacatcga gtccaagaac tcgattgaat atgatatcat cgtagaatcc gacaatatca  70020
gtgaagatat cgtaggccaa acgatttata cccctacagg aagaagtaat gttacttata  70080
tagaacgaaa ttcaaagat ggtaaattgc aatggcgttt aaccattcac aatctttag  70140 gccggtttat agttggacaa gagattaaat ctgaacgcac ctcatttaaa ggtatgatag  70200
tgcagggtgt acgcggtaaa gaattgttaa gtaacaatat cgattatatt aaccgtaacc  70260
gttcttatta tgttatgact attaaatcca acctccctac ttctcgatat cgtaatgacg  70320
tgttgagatt tgttcatcct gtaggatttg gttttatagg gattacgttg ctttctatgt  70380
ttgttaatgt tggtttgaca ttaaagcaca cggaaaccat tattaatata cttaagaact  70440
ataagtggga ctcaggtctt ccgtccgagt ggtacgatag agttgctgta atcggatttg  70500
atggtaatat agaaagagac cctagaacag gacttccggt ttataacgtt ggacctaaag  70560
caggcgaacc gttccctatt cctgatgatt atgatgcaga aaatgatttc tctgtattcc  70620
aaggtcaatt acctcatgaa cgtattaaaa agcatagtcc tttatttgac caaagtgcag  70680
taacattttc aaaatggcgt gctttagttg atgaccgact taaagctgat attggaaacc  70740
ctagagaccc gcaagaccca actcaggtaa aaattgatga ttaattcaac agtaatatac  70800
cgttctattg ttacttctaa attagaacg gaaaagatgt ataactttta cagaacaatc  70860
ggtgatggtg aagaccagaa cacgatgtat gtatctttcg ggagagccca accatgggct  70920
cctaacgaaa acgacccagg ctttgctcca ccttatcctg tagatgattc tgagggcgta  70980
gaagacgtct ggacaaacat gatgggttgt gttaaggttt ataagagtat gttggattgt  71040
gttgttcctc gcaaagactg gggcgatacc tcttatccta acctttcac tttccaaatt  71100
```

```
ggtgaaattg tagtggcgaa tagccaacct caaaaccgta ctgatgttgg tgcaggttgg  71160
atggtttatc gttgtgtgga cgtgcctgaa tcaggagcat gttctatttt gtcccttgat  71220
aataaaaccg agtgtattaa acttggtggt aaatggaccg ctaacgttcc ttcagttaaa  71280
gccccggcag gacaaggcga tacgaaggt atggtagaca ctggtgatgg ttaccttgg   71340
gaatacctt atgagattcc acctgatgta agtatcaacc gctgcactaa cgaatatatt  71400
gtggttccat ggccagaaga aattgccgaa gaccctgaac gttggggata cgagaataac  71460
cttacttggc agcaagatga ttatggttta atttatcgta ttaaagccaa tactattcgt  71520
tttaaagcat tcttagattc agtttacttc cctgaattta gtctgcctgg taacaaaggg  71580
tttagacagc tttcgataat ttctaacccg ttagaagcta agctcatcc atccgatccg  71640
atcattaaag ctgaaaaaga gtactatgat gttatagacc tctcccgcca ttcaggtgaa  71700
atgatttata tggaaaaccg tcctccggtt attcgttcca tggaccaaac agaagaaatt  71760
aacattatct tcgaattcta ataagggccg caaggccctt tcggggtat aaatacatta   71820
tatcaataat gaggcatacc tatgattaag caaactggta agttactaat tgacgtcggt  71880
gagattggta atgccagcac cggcgacatc ttatatgacg gtggtgttaa actgaacacc  71940
gacttaaaca acatctataa tacttttggc gaccaacgta aaacagccct tacaggcgaa  72000
actactggtc aaaaattaca tgccactgga tactatcaaa aattcggtga taccgaccaa  72060
gcaggttctg ttgatttagg ctctttggtg gatgtcgatg cttctaccgg ttctatagtt  72120
ttaacaactg taaaaggagc tgtgggcgaa ggtattgaaa taattaactc taatggaagt  72180
atttcagcta ccaactatct tgaaatccgt atattggatt cgttttgaa ccatcctaca    72240
tcaagcttaa gaatagtaac tccttataca cgggttcttt tatggtgtgt aagtgatata  72300
aacggtatag ctgtatggga ttattctatt gagagtatgt ttggtgacaa acgagtgcca  72360
ttaaatagaa catacaacat ttccaacgta cctagagatg tccaggtggt ttattcaggt  72420
caatattctt tagttaagct tttagttacg gcagtaaatg ccaatgaaac cgtttataaa  72480
gcttctgaat atcttttgtt tatggataac caagctaaaa aaatatattc tacggaatac  72540
gctgttatcc gtcgtggaca agccaccgat gaagacgaaa tttacaatct cgattttaaa  72600
tttgatacat ccaactatat agtggctacg gcatcatctg aaaccctat gagattagca   72660
attaaagtcg tagataccca aactattgga gtcccagtat aatgaaacaa gaattaaaaa  72720
taggccaggc cgttgacgat ggctccggag attacctgcg cgcaggtggt ctaaaaatca  72780
ataataactt taatgagtta tattatcaat taggtgatgg agataatcca cacgctgctg  72840
gtgcctggaa acaatattct actgcagacg gtcctttact taatgctgtt atgggtcata  72900
gctatacatt gaatacccaa ggtggaagga ttaacgttca acttcctaaa ggcaccccat  72960
cagaatataa ctttgtaatt cgtttacgtg acgtttattc ttcttggcaa gctaaccctg  73020
tgactattat accggcccca ggtgatacaa ttaaaggttc cgctgtacag gttgaaatag  73080
ctcgtaattt tgctgaccct gaacttgttt actgtgcccc cggacgttgg gaatatgttg  73140
agaacaaaca agttaaccgt atcccaaata acgacctcgc tactgtagca actaaacagt  73200
ttattgccac tgaaggtcaa actgatttct ggatattttt cccaggtcta acctataata  73260
tttcaagtct tagcgttatc caacgtggta acaacttgtt ctacggtgtg gatgatatat  73320
ttgatgaagc tacttctgag tttggtagcc caggcgcaaa cccaggcgaa ttggttgaat  73380
tgaacggtaa agatatccgt ttgaaatatc cttgtgaagc tggcgatacg gtaattatta  73440
```

```
aatcgtataa cgatggattg gcccaatggc gtagttctta taatcgtcgc gatattacta   73500
ttttagatac gacccttacc catgaaacca cagttaatgg ttctaaagta gtattagacc   73560
tttctaccgt acagactatt acatcagcag aattaaacgt ttctcctaca agccctatta   73620
accctaatgc ttgtcaggta atgcttaata gtactttatt gcatcaagcc ggtactgcag   73680
gattccctgc ttttattgt gaaggtgttg atacggatga tgcaggcctt tgtgcagatt    73740 caggcgggt atggacccaa tctaaatctg attatatttt gaatatagca gatgatgaca    73800
aaatcgagtc atttgaattt ggacgtaaac tggaacatgg cgatatcctt actgtaattt   73860
ggtataataa cgatatcggt accactatga ctattgacga gattttagat acaacaaacg   73920
atatctatat ttctcaaggt ccttcggtat ctttgactgg ccaggttcgt attactgatg   73980
tagataatcc attttctcct aactttgaac ctgtagcgga atccgaagtt tccattaata   74040
ctgccgcagt gatgtttgat tgttccacc ctattggaac gatttatgag aacaccgtga    74100
accctaataa ccctgcaact tatatgggta tgggtagttg gaaaagactg tctgatagtt   74160
tccttgtagg ttggtctccg gatgctgact cgttgttcaa tgcaaacaat aatgatttag   74220
actctggtgg tgttcctaaa tctactgccg gcgggacggg cggttctcat aatatttcca   74280
ttaaatatga aaacgttcct gaacttaata cagacgacaa ggtattagtt gccgatgata   74340
acggccctat tgttattggc ggatgtttgg tagacccgga tgcccaaggc ccggcttata   74400
caaaatatcg tgaagataaa gctacgataa acaaacagca atctacaacg cctattccta   74460
ttggcacttt gcctccatat acaaccgttt atcgctgggt gaggattgcg taatgacttt   74520
aacagaaatg aaaagcgggt taaaatcccg ccttgccgac tttttagaat tttcttttac   74580
aactaatcaa cctgccgcag tggcaggtca acgccctatt ggtggtccat cggcaaacca   74640
aacccaaaaa ggtgttatt accctacggt ccaaagtgct attgatgata ttgctttccg    74700
tgcagaactt cctgtcaatg cagttgtaac tactactgaa acagggccc ctggctttat    74760 tcagcaatct gataaattaa ctttctccgg ctccatttct tccggtggcg aattaggcga   74820
tacggttatt attaaggtat tcggtttgcc tgttgaagtt attgtgggtg attcttcggt   74880
cctggttgct tctaaagtta acgatgcttt tataagcgct attgctgata gttatatttt   74940
ggcagaaacg tctatcgacc ctctagacca gtctacttta aacattaaat ataacgacta   75000
ccaaaaccat attttgagc catttaaaca agcaggatgc accatttctc agactatagt    75060
tcaagagcct cgtgcgggtt atggatactg ggaatattta ggttctacta cagaatctat   75120
gacaggtgga accgtaaatg gaacaacaac cttatatcac tataagcgag taagttaatg   75180
tctacaaata cactaaaaca cataagtgat aaatcagaat ttaaaacatt cgaccctacc   75240
gggtcgaatt ttgacccctc tattactaat gtccaggatg cattggcgtc tatttccgct   75300
ataggtgtta caggtaatat accttcggct tctgaaacag aacaaggtat tattagatta   75360
gcgacccaac aagaagttat tgatggtact gatactttct ctgcggtaac tccggccact   75420
ttaaagggtc gtttagatat tcctactcaa gcaacagaaa cttatgtagg tatcacccgt   75480
tatgctacta acgctgaagc cattgccgga acagaaaccc aggctgcaat cgtagcatca   75540
tctttgaaag ctactataga ttatacattc accaatcgtt tagccacaga gaacactaca   75600
ggcgtactca agatttcaac cctgccggct gctctagcgg gtacagacga tacgacggca   75660
atgacaccgc ttaaaaccgc tcaggcaatt ggtgccgcta catccgcgtt gccgacttat   75720
gccagtgcta ctcaaactgt tgaaggtatt gttagaatcg caacaaatgc tgaagtggca   75780
aatggtacat tgaccaacgg tgtagcgatt tctccttccg gattaaaatc tttaacttct   75840
```

```
acccaaggac gagctggtat tattagatta gccactccac aagaagcttc ggctggcagc    75900
gattctaata tagctttatc tccttcaact cttctttctc gtactggtac taccggaagg    75960
ttgggtgttg ttaaattatc gaccacggtc ggttctggtg atgggaatac ggcattggca    76020
tataatgcta acgttatttc taccacaggc ggcaccatta atggtacttt aaacgttaac    76080
ggtactttac gtcgcaatgg gcgtgatgtt gttactatcg accaattaaa agattctgtc    76140
cctatcggta ctattgttat gtggggaggc cagattaata atatccctgc aggttgggct    76200
gtttgtgatg gtggtaactc tggtgaacaa gggttccgaa atgtagttgg tagtaaatgg    76260
ggttcaaccg gagcacgtcc tgacttccgt ggattatatc ctagaggtgc aaaccagact    76320
aatgacggcg gattaaaaga atgggacgct aacgtcagaa ttagagatgc taaaggtaat    76380
gatgccaaag gtaaacctaa attaggcgta ggttgtggtt catatggcca tggtactgta    76440
caagcccagc agcttcgttt ccataaacat gcaggtggct ttggtgaaca ggataactcc    76500
ggtgcatttg gtaataccgt tcgttctaac tttgccggca ctcgtaaagg gctggactgg    76560
gataaccgtt cctactttac aaacgaaggg tatgaaattg acggttacgg ttcacgagat    76620
tcaagaacta ctctaaacag tgaagggttg gttggtaacg aaaaccgtcc ttggactatg    76680
tccatcctat tcattattaa agttgcttaa ggaaataaaa tgattgacaa actgagtatt    76740
aaagaacttc cgtttgtcga tggtgtacct gatgcatccc aagagcgtat ccgttggata    76800
cgcaatggcg aatgtattga aggagccacg actaaatacg gtcacgacgg taatttgaat    76860 gccccctgctt taggagtaca aaccaacgta gttagattag aagaaaacag tatagcttct    76920
aaagacaaaa ttaacgagct tgtggataac gttaatttga ttaatgaagc cctagatatt    76980
tctactgata cgggtgttat tcaacaaatt gaaaagaacc gagttgatat actggctgtg    77040
gatgtaaagg cttccgaaac taaacaagaa ttaggtgact taaccgttaa ttttaatttt    77100
ttagaagaag atgtaggtta ttacgacccg tctttagatg gcccatatct caccgtcaga    77160
gaaaatataa atcttcttaa atctgaaatt ggacattatg cgaaccagga tataaacagc    77220
caaccgcttc ctccaggtga aacttctgaa gccaccggca tgaaacgtcg cattatggat    77280
aataccagtg ctattgtcga ccattcacaa cgtatagata cccttgaaaa gaattacgaa    77340
gattctgatg tagggcaact tggtcttaag cttaacgaaa ttcgtgaaga actgggtcct    77400
catattgata ccgtaggtaa acaaccagcg tataccagga tttctgctct tgaaactgct    77460
gctgaaagct ttaacgaatc aatagattct atcaaaacca gtataggttt taataaaggc    77520
cctattgata caagagtaac cacgctggaa actaaaactt ccactttaga aaacactgtt    77580
aataccggtt tggttcctag agttactgca gtggaaaccg ctatcggtac tgctgatgcc    77640
cctacttcta ttaacggtag attaggcggc ttacgcaccg atgttaatga actaaaaact    77700
atagtaggtg ctagttcatc agaagggctt cgtttccagg tttctgatat tgaccgtaaa    77760
atcggtgctg atgtaagtcc ggcggcagga acaattaata agcgtttgaa cgaccttaca    77820
actcaaggta atacctcagc ctctactatt caggacttgc aggccgaaat tggtaataac    77880
caaacgggta ttaaaggttc tattcttaaa attaccaacc aaattgaagg aacaaaccct    77940
aacggtagta ctgtagaaga acgagggtta ataaactctg ttaaaggcct tgaagctcaa    78000
atgcctacta aattgagtga cgcccctgct gatggtaaat tgtacggacg taaagatgcg    78060
gcatgggctg aagttgttga tgcaggtacg gaaatagctg cagtaaaagc ttctttagta    78120
gttactgatg gtgaggttga tgatttagga actcgtttaa ctgcggctga aggtaaaatc    78180
```

```
actgcactag aaactgagtt ggctaaacgc cctcctgttg ctcctgtggc tgacggactt    78240
ccgtatgttc tggttgataa cgcatgggta ctattgtcag attttgtgac tttaaaccca    78300
gcaccataat aaaagggctt cggcccttt ttgctataaa tacggttatt agaggaataa    78360
aacatggcaa gcgaatcatt taaccctaag caactcaagg acgctattct gcgccgcctg    78420
ggtgcgccga ttacaaatat tgaagtaact acagaccaag tatacgattg catccagcga    78480
gccctagagc tctacggtga gtaccattat aacgggtata acaaaggcta tcaggctttt    78540
tatatcggtc atgacgatga agaaaaattc cgtaatgggg tatttgacct taaaggccgt    78600
aatatatttg cagtgacaca aattttgaga accaatgtag gttctttaac atctatggac    78660
gggcaagcaa cttatccgtg gtttactgat tttgtattag gcttagcagg tattaatggc    78720
gggttagggt cttcgtgtaa cagtttcgga cctaatgcct tcggtgctga ccttggttat    78780
tttacacaat taatgcaata tcgttctatg atgcaggacc ttttggttcc actacctgat    78840
tattggtata acgatgccac cgaacagttg aaggtaatgg gtaactttgt taaaggtgat    78900
tttattgtaa ttgaagtttta tactcgctct tttaatggag tggattctat ggtaggaaat    78960
actgtaggat atggttatgc ttcagcttgt ggtgaagatg catggagccc aggtgctatt    79020
tgggataatc cggcgcgtcg tatttctggt atgcgtgtag gtgaggacct tggtcttcaa    79080
gatggtgcat ataataaccg ttgggttaaa gattatgcta ctgcattggt taaagaagtc    79140
aatggtaata ttttagccaa acaccaaggc atgcaacttg caggtggaac cactgtagat    79200
ggtattcgat tgattgaaga ggctcgttta gaaaagaac gtcttcgtga agaattagat    79260
ttactcgacc caccaacacc tattttaatt ggataattat ggctactttc gattcgagtt    79320
tattcgctaa gctagaagat aatactggct atgctaacac gaacgaaact gaaataatga    79380 acccttcgt caacttttat aagcatgaga atacccaaac attggctgat gctttagttg    79440
ctgagtctat tcaaatgcgt ggtattgagc tttattatat accacgtgaa tacgttaaac    79500
cagaccagct atttggcgaa gaccttcaga acaaatttac taaagcctgg aagtttgcag    79560
gatatttgga ttcctttgaa ggttattccg gtgacaatac ttatttcagt aagttcggta    79620
tgatggttaa tgatgaagta acaatcacaa ttaaccctaa ccttttaaa catcaatgca    79680 atggcactga acctgtttca ggcgacctga tttattttcc aatggacaat agcctattcg    79740
aaattaactg ggtacaacct tacgacccgt tctatcaagt gggtgctaac gtccaacgtc    79800
gaatcactgc taccaagttc atttacaacg gtgaagaact tcgtcctgaa ttacagagaa    79860
atgaaggtat taatattcct gaattcagtg agcttgattt aatgcctgtt aagaatatcg    79920
acgggttggc tgatatctct gacattcaat acgaagaggt caatgagatt aatgctgaag    79980
cggctgaatt cgtacatcct tatgttgtaa ttaatggacg aggagaggat gttcctccta    80040
cagcatttga tgatgctttt ttagatgatt aaataataca tggcgcatgg tgcgccattt    80100
taggaggttt gatgtttgga cattggtata atagttcgct acgtcgctat attgttttga    80160
tgggtgattt atttttcccat gttcaagtgg cgcgtcaaag agaagataca gggcttaaat    80220
ttattaaagt tcctattacg tatgcttcta agaaagatt tatggcaaat ttgggtaaat    80280
ggactgctgt tcaaaatatt ccaaacccta atatgtctcc taaagaacga gctgaacaaa    80340
aggctaaagt ggaaacagtt ctcccacgta tgaaccttca aatggttgat atgctttata    80400
actcacaata taaacggct cttcagaata gaacacaaat tcaatttgag aatggagacc    80460
ctcgtaaacg ggttagccaa tattctccta ctccggttaa aatgatttc gaactgggta    80520 tttacactag aacccaagat gatatgttcc aaattgtgga acagattatg ccttatttcc    80580
```

```
aacctcactt taatacaaca atcactgaac tctatacaaa cgagattaaa tttgaccgtg    80640
atattcgtat tgtgttccag tctattgcta tggatgaaca acttgaaggt gataccgctt    80700
cacgtcgtcg tttagaatgg tctatgatgt ttgaggttaa cgggtggtta tatcctccgg    80760
ttaaagaaat ggaaggcgaa attaaaacca tttatcttga tttctttgct aactcaaagg    80820
aactcgctcc tgaaggtaat ttcgaatcag ttgatagtga agtggttccg agaggtgtag    80880
aacaaacaga atgggatgga agttccgttc aaacatattc acaagatatt ccagtgcctg    80940
tcgagccagc gcctccagca ccaaggagaa acccatgagc gatttagata tcaataaatt    81000
aatggatatt accgacctcc ctggcctgac cggggaggaa gttacagcct atgaaccaat    81060
agtattaaaa gaagtggaaa gtaatccaca gaaccgtact cctgatttag aagacgacta    81120
ttctgtggtt cgtagaaacc tccatttcca acagcaaatg ttaatggatg ccggtaaaat    81180 attttagaa gttgctaaga acgctgaatc accacgtcat atggaagtat ttgccacatt     81240
aatgggccag atgactacca ctaacaaaga gctttaaaa cttcataaag aaatgaaaga    81300
tattaccgct gaacaaatcg gtactaaagg tggagagcct aatcaaacta atatccaaaa    81360
tgccactatt tttatgggtt caccaaccga tttaatggat gaagtgggag acgcttatga    81420
ggcccaggaa gaacgtgaga aggtaattaa tggaacaacc agttaacgta ttaagcgatg    81480
accatccact aaacgaaggc aagactacag tcattaagcc gccgggttcg cttgaacgta    81540
aaacagaaga aggtatcaat tggattaaat cccaatggga tgacaaatgg taccctgaaa    81600
agtttagtga ttatttacgt atccataaaa tagttaaaat tcctaataac ggggaccgtc    81660
caaacgaatt ccaacgtttt aaagataaaa tgaataaacg tacccgttat atggggcttc    81720
ctaaccttaa acgagctaat ataaaaactc aatggtctcg tgaaatggtt agtgaatgga    81780
agaaatgtcg tgatgacatt gtctattttg ctgaaactta ttgtgcaatt acacacattg    81840
actatggtac aattaaggtc caacttcgtg attaccagcg tgatatgctt aaaatcatga    81900
gcaagaaccg tatgacgact tgtaacctgt ctcgccagtt aggtaaaaca accgtcgttg    81960
ctatattcct tgcccacttt gtttgcttta acaaagataa ggccgttggt attctggcgc    82020
ataaaggctc gatgtctgcc gaagtacttg accgtaccaa acaagctatt gaattgcttc    82080
cggatttctt acagcctggt atcgtagaat ggaacaaagg ctcaattgag ttggataatg    82140
gtagttctat tggtgcttat gcttcatctc ctgacgccgt gcgtggtaac tccttcgcaa    82200
tgatttatat tgacgaatgt gcgtttatcc ctaactttct agattcatgg ctggctattc    82260
aaccggttat ttcatctggt cgtcgttcca agattattat tacaaccact ccaaatgggt    82320
taaaccactt ctatgatatt tggactgctg cagtagaagg taaatcaggc tttgcaccat    82380
atacggccat ctggaactca gttaaggaac gtctttataa cgatgcagat atatttgacg    82440
atggttggga atggtcctct cagacaatct ctgcgtcctc tttagcgcaa tttagacagg    82500
agcactgtgc agagttccaa ggcacaagtg gtacattgat tagtggtatg aaattggcta    82560
ttatggattg ggtggaagtt actcctgaaa acggatactt ttatcgtttc catgaaccgg    82620
accctacaca caaatatatt gcttcattag actgctcaga gggtcgtgga caggactatc    82680
acgctttaca tattattgac gttacaacgg atgaatggga gcaggttgct gttttgcatt    82740
ctaatgaaat atcccatatg attctccctg acatagtgta taaatatcta atggagtata    82800
atgaggctcc tgtatacatt gaacttaaca gcacaggtgt ctcggttgcc aaatctcttt    82860
atatggacct tgaatacgaa aacgttattt gtgattcgat gcaagattta ggtatgaaac    82920
```

```
aaaccagacg aactaaacct gttggctgtt ctacattaaa agaccttatt gaaaaggaca   82980
aattaaaact taatcataag caaacaataa tggaattccg tacctttagt cagaacaagt   83040
tatcttgggc tgcagaagat ggtttccatg atgaccttgt gatgagttta gtgattttg    83100 cctggttaac gacccagcaa aaatttgccg acttcattga ccgagacgaa atgcgattag   83160
catctgaagt ctttagtcgt gagttggaag atatgaacga agaatataat ccagtcgttt   83220
tcgtggatgc tggcgataat tcatatgaat attcaccgtt gaatcatggt atttcgttta   83280 tataataac aataaagcat aaccaagagg attcaaaatg tctttattat caccgggcat    83340
tgagctcaaa gaaacgtccg tacagagtac tgtcgttcgt aacgcaacgg gtcgtgcagc   83400
gctggttggt aaattccagt ggggccctgc tttccaggta actcaaatta ctaacgaagt   83460
tgaactggtg gatttgtttg gaggtcctaa caacgaagtg gcagattatt ttatgtctgg   83520
tatgaacttc ctccagtatg gtaatgacct tcgtacagtt cgtgttgtta accgtgaatt   83580
cgctaaaaac gcatctccta ttgcaggcaa tatagaaacc actattacta cggctggttc   83640
taactatgcg gtaggcgata aaattaatat caagcacaac caaaccgttg ttgaatctga   83700
aggtcgtgtg acttctgtag atacggatgg taaaattctt tccgtgttta tcccatcagc   83760
aaaaattatt gcttatgcac gttctcttaa ccaatatcca gaccttgggc ctgcatggac   83820
ggctgaagtt acttccgctt cttctggtgt ttctggtact attaccgtag gtaaaattgt   83880
aaccgattcc ggtattctgt tgactgaagc agagaacagt gaagaagcta ttacttccct   83940
ggaattccaa gcatctctta agaaatttgc tatgccaggc gtagtggccc tttatccagg   84000
cgaaattggt agtactctgg aagttgaaat tgtttctaaa gcggcttatg atgccggttc   84060
tactaaaatg ctggatattt atccaggtgg tggctcccgt gcttctattg ctaaggcggt   84120
atttaattac ggtcctcaaa cagatgacca atatgctatt attgttcgtc gtgatggggc   84180
tatcgtagaa tctgtcgtac tttctaccaa agaaggcgaa aaagacgttt acggtaataa   84240
catttatctt gatgactatt tcgctaaagg tacttccaat tacatctatg caacttctct   84300
gaactggcca aaaggcttca gtggtatcat taatctgatg ggtggtgttt ctgccaacga   84360
taaagttacc gcaggcgatt tgatgcaggg ttgggatttg tttgccgacc gtgaagcact   84420
ccatattaac cttttgattg ctggtgctgt tgctggtgaa ggtgatgaag ttgcttctac   84480
cgtccagaaa cacgttgtta gtattgctga tgaacgtcag gattgcttag cctttatttc   84540
tcctcctaag ggtcttttgg ttaacgttcc attgactcgc gcagtagata accttattga   84600
ctggcgtacc ggtgcaggta cttt cgatgc caacaatatg aacattagca ccacttatgc   84660
tgctattgac ggtaactata ataccagta tgacaaatat aatgacgtaa accgttgggt   84720
gcctctggca gctgatatgg ccggtttgtg tgcacgtact gatgatgttt ctcagccttg   84780
gatgtctcca gctggttata accgtggcca gattcttaac gttctgaaat ggcaattga    84840 acctcgtcaa gctcaacgtg accgcatgta ccaagaagct attaacccag ttgttggttt   84900
tgctggtggt gatggtttcg tattgtttgg tgataagact gcaactaaag ttccatctcc   84960
gatggaccat attaacgttc gccgtctgtt caacatgctt aagaaaaata tcggtgatgc   85020 ctctaaaatat aaactgtttg aattgaacga caacttcact cgttcaagct tccgtatgga   85080
agtttctcag tacttagatg gtattaaggc acttggtggg atttatgaag gacgtgtggt   85140
ttgtgatact acagtgaaca cccctgcggt tatcgaccgt aatgagttta ttgctaatat   85200
ctacgttaaa ccttctcgtt ctattaacta catcacgttg aacttcgttg caacgagcac   85260
tggtgctgat tttgatgaat tgattggacc tttagtataa tctattatcc caggctgtaa   85320
```

```
tataaagaac ctaaaaccat tataccatga gtttggttac agcgtacatc acgtagaaat   85380
gcgcctggga ttgattattc tctcagaata tgatttatca actgtataac taaaaacgtc   85440
gcaggcgcaa tcctgcgact ttctggtata taaatataag tatgattact aatactctat   85500
ttgaaatacc tataacaaat cgtaacgttt ctgcttttaa aaatcttggc tatcaagtta   85560
aaagtgggag ctcctattta ataaaattag aagactgtcc tggaaaaatt gctgttacgt   85620
gtaaatgtga taaatgtgga atttattata ctgtaacaaa agggcgactt aatgaaacca   85680
attctaagtt ctgtaaagag catcgttggg aagtctattc agaaacaaga aaagaatatt   85740
ggaattctga tgaaggcata aaaatccgta aaactaaagg gcctaaaatt tctaagtcta   85800
aaaaaggtat aaagattgaa gcttgttcag gacctaaaaa cggaagatgg aatcctaaca   85860
aatctgaacg taataaatat tattattcag tgaggtcttt tactaataag acttttaaag   85920
aagaagttga taaactacca aataggcacc taagcgggat atgcggtgtt gaagggcttt   85980
atcaattaga ccatagggta tctatcaaat atggatttga aaatggtgtc tctcccgaaa   86040
taataggaca catttgcaat ctagaaatga ttccttggga aaagaatcgt agtaaagatt   86100
ctaaaaatag tatagattta gatatgctat tccatttaat tgaagaatat gataggaaac   86160
actaacttat ggaacttacg gatatcacta gggccttcga gtcaggtgac tttgcacgtc   86220 ctaaccttt cgaagtggaa attccatttc tcggtaaaaa ctttagcttt aaatgtaaag   86280
cagcacctat gccggcaggc attgtagaaa aagtaccggt tggctacatg aaccgtaaaa   86340
ttaacgtagc tggtgaccgt acgtttgatg attggaccat taccatttat aacgatgatg   86400
cacatgacac tcgtcaagca attgttgatt ggcagaatct ctgtcatggt atgaccaatg   86460
aaattacggg tgcagcacct gcagaatata agaaacaagc agtagttcgc cagttccatc   86520
gtgacggcaa gactgtgacc aaagaagtta caatttacgg cttatggcct actaacgttg   86580
gtgaagtcca gatggattgg gacagtaata acgaggtaga gacatttgaa agcacatttg   86640
ctattgattg gtgggaataa tttttacttt tatagcaaat tatgatagta taaatacatt   86700
caaacaatga agtcaaggag tttagaatgt attgtactta tttaactata tacacggggt   86760
ctaaaatgcc ccgtcgttat atcggctcaa catacgttga aaggattctt gaagaagggt   86820
ataacggttc agtattatcc caagcatata aaaagatttg gaaatcagaa cgtaaagaaa   86880
atccacacct ttttaaaacc cgaattttgt ctttatttga aaccgataaa gaagctcgta   86940
tagctgagaa ggaacttcaa ataaagtata acgtagtcaa atccaaaaac tatataaata   87000
tgtcattagc tcagcctgat gggttctttg gaatgtctcg taaaggatat aaatggtcta   87060
aagaatcttt agataaaagg tctgctacca atacaggtaa aaagaggccg gagcattcca   87120
aagctctaaa aggacgaaaa cgacctggac aagccaaagc tatgtcaggt gaaggtaatc   87180
cgatgtttgg taaagaacat ccggctaaag gcaaaaagat taatcagcca aggatgattt   87240
gccctatctg tggtgttgaa tcaactcgtt cggctataac ccgttatcac aaacacgaaa   87300
atgaatgagt ataatagaa ttatcaagga gcttcggctc cttatcccat tcatcggaga   87360
ctctaatggc aaactttaat acaatattaa gttttcttaa gccatgggct aatgaagacg   87420
aaaaagaata taaacaacaa attaataaca atttagagtc tgtcaccgca cctaagcttg   87480
atgatggcgc tcgagaaatt gagacacaag agcaaaatat tccttataat gctcttatgc   87540
aacagatgtt tggtagtaat gagcctgaag ttaaaaatac cagggaactt attgatacct   87600
accgtaattt aatgaacaac tatgaagtcg acaacgccgt acaggaaatt gtgtctgacg   87660
```

```
ctattgtcta tgaggatgat aaagaagtag ttgcattgaa tttagacggg acagaattta   87720
gtcaagcaat taaagataaa atcttggccg aattcagtga agttttaaac cttttaaatt   87780
tccaacgtaa aggcaccgac catttccaac gctggtatgt agactcaaga attttctttc   87840
ataaaattat aaaccctaaa aaaatgaaag atggcgtaca agagcttcgt cgcttagacc   87900
cacgccaagt ccaatatatt cgtgaaatcg ttacacgtat ggaagacggt gttaaaattg   87960
tagacgggta tcgtgagttt ttcgtttacg acacaggtca tgaaagctat tgcgcagatg   88020
gacgcattta ttcagccggg actaaagtta aaattcctcg tgctgctgtg gtttatgccc   88080
attcaggatt attagattgt tgtggtaaaa acatcattgg ctatttgcaa cgtgctatta   88140
agcctgcaaa ccagcttaaa ttgatggaag atgcaatggt catctaccgt attacccgtg   88200
ctcctgaccg tcgtgtgttt tatatcgata caggtaatat gccttcacgt aaggctgcag   88260
cacaaatgca acatatcatg aacacgatga aaaaccgtgt ggtgtatgat gcttcgacag   88320
gtaaaattaa aaaccaacaa cacaatatgt ccatgactga agactattgg ttgcaacgtc   88380
gtgacggtaa agcggtaaca gaagttgata caatgccagg tgctactggt atgagtgata   88440
tggatgacgt tctttatttc cgcacagcac tttatcgtgc gctgcgtgtt cctgaatcac   88500
gtatccctag cgagtctaat tctggtgtta tgtttgatgc cggtacagca atcactcgtg   88560
acgaattaaa attctctaaa tggattcgtc aactacaaaa caaatttgaa gaattttcc   88620 tagacccgtt aaaacaaac ctcattctta aaaagattat tacagaagat gagtgggaaa   88680
aggaaataaa taatattaaa gttacgttta accgtgatag ctatttcagt gaatgaaag    88740 atgctgaaat catggaacgc agaatcaata tgctaacgat ggctgaacca tttattggta   88800
agtacatttc acatcaaacg gctatgaaag atttcctcca aatgactgac gaagaaatta   88860
atcaagaagc taagcaaatt gaagaagagt ctaaagaggc tcgtttccaa aacccagatg   88920
aagaagaaga ggatttctaa tggaagattt aatcgaagct attaaatcaa acgacctcgt   88980
agcagttcgt aaagcagcag ccccgcttat cgaatctcga gtagccgctt tgattgaagc   89040
ccgtaaagca gaaattgctc gctccgttat gattgaaggc gaagaagctg acgaagatga   89100
cgaagacgaa gataaagacg ataaagcaga taagaaagac aaaaaagaat ctgacgacgc   89160
ggatgatgac gacgaggacg acgaataatg ttccttatcc ctgatgatta cgaattaact   89220
ctagaaagcg tagaggccaa aattccagaa gcacagggac gttttgctgc tctttctgaa   89280
gcgctagaga aaagcgatat aaataatctt gtagagaaca tgattgctga aggcgatatc   89340
gaatatgcta tcgctcttgg ttctttaaat gaatcaatgg ctcttaacga atttatcgtt   89400
aaacacgttt cctctaaagg tgtgcttact cgtactaaag atattaaaac ccgtcaacgt   89460
aacgcattcc aaacgaccgg gttatctaaa gcaaagcgcc gtcagattgc tcgcaaagca   89520
tctaaaacca aacgtgctaa tccatctact caagtgcgtg ctgaacgtaa gcgtaagaaa   89580
gcccgttcta aacgtaaagc ttttggactt aactaatgaa acctgaattg ctcatcgaac   89640
attggggaca accaggtgaa attatcgatg gggttcctat gttggaatct catgatgaa    89700 aaaattctgg gcttgctccc ggcctttata tagaaggcat tttcatgcaa gcagaggtag   89760
ttaaccgtaa taaacgcctt tacccaaaac ctatttggga aaaagccgtt gccgattata   89820
tggcagaaca ggttgctact aaacaagctt taggagaatt aaaccaccca cctcgtgcta   89880
acgttgaccc tatgcaagct gctatcatta ttgaagatat gtggtggaaa ggtaatgatg   89940
tttatggacg tgcacgtatc atcgaaggtg accatggccc aggtgataaa ctagctgcaa   90000
atatccgtgc cggttgggtt cctggtgtta gttctcgtgg tcttggttct ttaaccgaaa   90060
```

```
ccaacaaagg atataagcgt gtaaacgaag gttataaatt aaccgtcggt gttgatgcag    90120 tatgggacc atctgctcct gatgcttatg taactccaaa gcaaattaca gaatcacaaa    90180
cggtagaaac cgataccagt gccgatgacg cctttatggc tctcgcagag gccatgaaaa    90240
aagcgttata aatattatta tctaaacaac aggactacaa aatgcttaaa gaacaactga    90300
tcgccgaagc acagaatatt gatgcttccg ttgctcttga cagtattttc gaatcagtta    90360
atatttctcc ggaagcaaaa gaaactttcg gcactgtatt cgaagctacc gtcaagcaac    90420
acgccgtgaa actggctgaa tctcacatcg ctaaaatcgc tgaaaagcg gaagaagaag    90480 ttgagaagaa taaagaagaa gctgaagaaa aagccgataa gaaaatccaa gaagctgccg    90540
gtcgtttcct tgaccacgtt gctaaagaat ggatggctga aaaccagctg gctgttgata    90600
aaggtattaa agccgaactg ttcgaatcca tgttgatggg tatgaaagaa ctgtttgttg    90660
aacacaatgt ggttgttcca gaagaagcag tagatgttgt tgctgaaatg gaagaagaac    90720
tccaagagca gaaagatgaa accgctcgtc tgttcgaaga agttggtaag cgcgacgcgt    90780
atattaatta cgtacagcgt gaagttgctg ttacggaagc aactaaagac ctgactgaat    90840
ctcaaaaaga aaaagttagt tctctggtag aaggcatgga ttattccgat gcattcggta    90900
aaaaaattgg cgctattgtt gaaatggtta aaggtcagtc tgacgttgaa acccaatca    90960 ccgaagccgc tataaataaa aatgtagacg atgctgcggc actgaattac atttcagaag    91020
cagttgaaga aaaaggcgct aagcctaccc tgtccttcgc ggacctgtct gcaatcgcag    91080
catcacgaat ttcttaatta ataaggttat acaacacatg aaaaagaatg cattagttca    91140
aaaatggtcc gctctgctgg aaaacgaagc ccttcctgaa atcgtgggtg cttctaaaca    91200
agctatcatc gctaaaattt tcgaaaatca ggaacaagat atcctgactg ccccggaata    91260
ccgtgatgaa aaaatctccg aagcatttgg ttctttcctg accgaagctg aaattggtgg    91320
tgaccacggt tatgatgcta ccaatatcgc agctggccag acttctggtg ctgtaactca    91380
gattgggccg gcagtaatgg gtatggttcg tcgtgctatt cctcatctga ttgcttttga    91440
tatttgtggt gttcagcctc tgaataaccc taccggccag gtatttgccc ttcgtgcagt    91500
ttatggtaaa gaccctatcg ctgctggcgc taaagaagct ttccatccga tgtattctcc    91560
agatgctatg ttctctggtc agggtgctgc tgaatctttc gaagcactgg ctgcaagcaa    91620
agttctggaa gttggtaaaa tttattctca cttcttcgaa gctaccggtg ctgcacactt    91680
ccaggctgtt gaagccgtaa ccgttgatgc tgctgctact gatgccgcta aactggatgc    91740
tgctgttacc gctttgattg aagctggtaa gttggctgaa ttggctgaag gtatggctac    91800
ttctatcgct gaacttcagg aaggctttaa cggttctacc gataaccgt ggaacgaaat    91860 gggcttccgc atcgacaaac aagttatcga agctaaatcc cgtcagctga agcaagcta    91920 ttctatcgaa ctggcacagg accttcgtgc agtacacggt atggatgcgg atgctgaact    91980
gtccggtatc cttgctaccg aaattatgct cgaaatcaac cgtgaagtta tcgattggat    92040
taactactct gcacaggttg gtaaatctgg tatgaccaac accgttggcg ctaaagctgg    92100
tgtgtttgac ttccaggacc cgattgatat ccgtggtgct cgttgggccg gtgagagctt    92160
taaagccctt ctgttccaga ttgataaaga agcagccgaa atcgctcgtc agaccggtcg    92220
tggtgctggt aacttcatca tcgcttcccg taacgtagtt aacgtactgg ctgcagttga    92280
tacttctgta agttatgcag ctcaaggtct gggtcaaggt ttcaacgttg acacaaccaa    92340
agcagtattt gccggtgttc ttggtggtaa atatcgcgtt tacatcgacc agtatgcacg    92400
```

```
ttccgattac ttcaccatcg gttataaagg cgctaacgaa atggacgcag gtatctacta    92460
cgctccgtac gttgcactga ccccgctgcg tggttccgat ccgaagaact tccaaccggt    92520
aatgggcttc aaaactcgtt acggtatcgg tatcaacccg ttcgctgacc cgtctgcaca    92580
ggctcctacc aaacgtattc agagtggtat gcctgacatc gttaacagcc ttggtctgaa    92640
tggttacttt agacgcgtct acgttaaagg aatttaatgc tttaacgtta aaatacataa    92700
ccttatggga gactccggtc tcccattctt gtttctatac tatgcaatct taactcgacg    92760
attgatgata tcacggaagt caatacgatt ttcttggatt ttcagccagt taccagattt    92820
gtctttggta tgggtagagt attcaccgtt ccaccagaag tcagtttcat aggccagggc    92880
ttcgtatttc ttaaccaatg cattaactgc attaccgtta ggattggtac caaattttc    92940 taccagagct ttgatgtctt tgtcaaggtt agaaagtgta gtacggataa agtttaattt    93000
gttcattttt aatctcctca tgttttgata ggtctatagt aacacgacgc ttttgtgtg    93060 taaaccactt ttataaataa aattatattc tcaataagga aaatagcaat ggctaaaatt    93120
aacgaccttt taaaagagtc gaccactact tcgagttctt cgattggtcg tccaaattta    93180
gtagctttaa ccagagctac gaccaaactg atttataccg accttgtagc tcagcagcgt    93240
actaaccaac ctttggctgc tctatatggt atcaaatatc ttacagaaaa aaacgaatta    93300
tctttccaga caggtgctac ttattctggt gcagtatccg ctaaagaccg tgccactatt    93360
ccagttttca ctgcaggcgc tgtttacgct aaagatgatt tgttccaatt tgaaaacgta    93420
gtttataaag ctttggtagc atcaccattt gcgggtgcta ctggtgatga atacgaacaa    93480
cttcaagaag ctattgttaa attgaccatt cgtattatgt ctgaagccgc actgactgag    93540
cgttttgaag gtcctcaaga agtagatatc tctgaagcca gattcatcgt taataaatgg    93600
aacgctccag ttaaatcccg taagttgaag agtactgtta ctgtagaact ggctcaagac    93660
ctcgaagcaa atggtttcga tgcccctaat ttcttggaag acctcctggc tactgaaatg    93720
gctgatgaaa tcaacaaaga tattcttcag tccctagtta cggtttccaa gcgttataaa    93780
gttgaaggtt tgtgtgatga cggcttaatt gacctgagtt atgctaactc accggaagct    93840
tctcgcaagc tttatgaaat agtttgtgaa atggtttctc atatccagcg cgcaacctct    93900
tatacggcaa cttatgtagt agcgagtact cgtgtagctg ctgttctggc tggttccgga    93960
tggttaagac acaccccaca gaacgacaaa tatctttctg caaatgcata cggattcctg    94020
gaaaatggtt tgcctgtgta ttgtgatacc aacacgccga ttgattatgt tactgtaggt    94080
gttaaagagg aattcggtgg gaaagaagcg gtaggttctt tgttctatgc gccgtataca    94140
gaaggccttg atttggctga ccctgaacat gtaggtacat ttaaagtggt cgttgaccct    94200
gaaagcctgc aaccatctat tgcattaatg gttcgttatg cactggctgc taacccttat    94260
acggttactt ctgatgataa acaagcccgt attattgatg cgactaatat ggatttgatg    94320
gcgggacgtt ctgatatgtc cgtattgctt ggtgtgaaac ttcctaaagt tttgactgaa    94380
ttaaactaac aaaaagggga ccgtgaggtc cctttgtcgt cttacgacac taattcaatc    94440
catactgctc gtagggtatc ttttacgcac tcaacaagtt gcttttaac ttcaacagga    94500 ttttctgcat cagttaattc taattcttca cgggcagctt cttctaagat atcttggact    94560
gtcaagccca ttaccttcc aaaatccttt ttagatactt cgccaatctt actgatgacg    94620
ttgttaatgc ggttaacagt cacataatcg gtgaattgcc acatcaaatc catatcgtct    94680
tgggataaaa ctacagccgc cttaataggc ttatcagact ttttcttctc gctgaattta    94740
gagttcttgc atttaatcgc tacgcgattt ccgtttggaa gccaggtagg aacatcaggt    94800
```

```
ttcaatacaa agccttcagc cgtgaatacc ttaccttcta ccttaggaat aaagtctgtc   94860
gagtttgcaa tagttaggcc agcgttatcc actgcaaaat tataatcagg aataactgaa   94920
tcaaagtcat taggtaattt aataaggtct tcaaagctac cagtagccag acatggagct   94980
accttaaact tatggataat acagaaggct tccatcaatg tatcggttag aacagattct   95040
gaaccatctt ccttagtaac tcggatatcg aacacataaa agtctttatc accgtagtcc   95100
acattcttct ggatacctgt cccagcgaat tcgccataaa tctggtacga ctgataatta   95160
atcgattcaa ttagatgttg aactgattta atagaatcag catagttctt aagtacaatt   95220
tcatagccgt agaaatcttc agcagggagg atagcgccag tgcgcttggc gcatgtgact   95280
gcgtcacgtt ctatgattag actaaagtta gttccatgaa tcttctcacg tgctacccat   95340
tcaccaccag tcaaaccgtt agtacggagt ttttcgataa acttattgtt gtagtggttt   95400
tcgagactgc tatatttctt gaacataaat caccataata aatataatta aatagaagag   95460
ctagtagtct tctgtcacca agccaaatgg tttaacggaa ggacctagac ccattataac   95520
acatctaaat ttaaagcata ttactttgaa ccagaacgcg ctttgcgccg aaccttgttg   95580
ttcaatcttt tacgataaac aacctttcct ttcgctttaa atttgacctt ggcttgttct   95640
acatcaaccc atgctttggc catgtcctta gcagtcccgc ccattttttt agcaatttct   95700
ataaaattca acccagattc gtgtaaaaaa tgtactttaa ccttatccat aacaattctc   95760
tcgttgagtt ggtaaaaccc atcttaacat agaatttta acttgtaaac aggaattttg   95820
tactttaatg caaaatgggc cttgcggccc ttaattaata aacgtaatcg tatataatac   95880
cagcttctaa agcggtgcga tgaataattc gaccattacg agattcttgt acatcaacct   95940
ctggatagtc ggtaatcatt ttttgaagcg tatatcggtg caaataatac gggctatccg   96000
ggttatcagt tttccagtct tgcccagcaa gagtcatttt ctgaatttca tccataaccc   96060
accaaccaca ccagatataa gctgaattgc gtactggcaa tggatgcaca taaggtaatt   96120
cgccatccgg aactggtgcg actttagccg tgactgttac attaccggtt tttgtgacag   96180
tcgccgggtc ataatcagtc gccgaaacca aacagaaac ttcaataacc tgtgaacctt   96240
cagcacttgt atcgattgct agagtatccg tggtgccaac tacaggagaa ccatctttct   96300
tccaagaata ggcaaaagta gcaccagcag gcgcgccgac tacatccgct ttaaaagaag   96360
ctggagtgcc ttccggaaca ttaattgatt ctggggttaa tgtaacagaa acatctgaca   96420
tagttttgtt ctggatagtt aaagtcgtct cagcttcagc agtttccggt tcgccgtccg   96480
ctggtgtggt tgttgcaaca actttaatag tcttgctgcc tgctggacca acagcaacat   96540
aatccattgc agcggtcaca gaagattgag gaacgccatc aacggtccag acaaatgatt   96600
cggtaccttc agctgcagcg ccagcgccgg ttgcagtgaa attggttgtt gctccaataa   96660
cggccgtagc cgccaaagga gcaatagtta cggtataagc cataataaac ccttatttta   96720
aagtgacaaa agatgagtta cgagtttctc gtattagaac agacccatta cgattgatgt   96780
aataaatcaa actgaatagt gtttggtgtg cagtaggatg ttggaaagca gttggacgtt   96840
ctttccaatc cggggtctca gaaatccatt ggtaaatcca ccaaggaacg gtgcaataac   96900
ccgggttctt accgataagc aaaagattag gactgaagtc ttcaggtaaa gagaatacag   96960 gttttttccga ttcaacaacc ttggctacag cctctttgaa tttctcttca acaaatggaa   97020
catcttcttc aataatctct actttaggaa gttcggctac ctcaacgact tcaacaactg   97080
cctcaggagc atcgaacaac agggttgctt cttctttagc aggttcagca ccatcaataa   97140
```

```
attcattaga acctgtaagt tcgtcggcgg catcaatcaa atcagaaatg acaaccctt    97200
cggtttccgg aagtggttcg tcggccaagg ctttaagacc ttcagtgata tcgataatca   97260
aattatcaaa cgaacgggtt ttcttaagtt ttaaaccgaa ctgttcgccg tattcgatta   97320
acttagcttt agcttctttt ttatcttcga gtgcacgaag ctcttcaata tattgagtat   97380
ccataattag tctcttgttg gtgtataaat ataactatat ttataactga gaattactta   97440
tgcaaattca agtacatttt gataatttta gtcatgtccg tattgaatgc gatgaatcta   97500
cattctacga actcagagac tatttttagct ttgaagctga tggatataaa ttcaaccctta  97560
aatttcgtta tgggcaatgg gatggacgta ttcgtcttct ggattataac cgtaaacttc   97620
cttatggatt ggttcctcaa attaaaaagt tcgccgaaca atttgaatac tctctgtgga   97680
ttgacccacg tattcttgat caggaagata tttctcgtga agattttgat tcatgggtgg   97740
cttctcaaga aatttattca gggtctacca agattgagcc tcattggtat cagaatgaag   97800
ccgtatacaa cggcctgaca aaacgtcgcg caattctgaa tttacctaca tccgcaggta   97860
aatcattaat ccaggcactc ctgagtcgat attacgttga gaactatgaa ggtaaaatcc   97920
ttattttagt tcctactact gcacttgttg accagatgat taacgacttc atcgattatc   97980
gtttgttccc taaagccgca atgcttggaa ttcgttcagg tactgctcgt gattctgatg   98040
caatgattta tgtttcaact tatcagactg ctattaaaca acctaaagaa tggtttgctc   98100
agtttggtat gtttatgaac gatgaatgcc atttggctac aggtaaatct atttctacta   98160
tcatcgaagg cctaaccaac tgtatgttta aattcggttt gtctggttct ttaaaagatg   98220
gtaaagctaa tttaatgcaa tatatgggtt tgtttggtga tgtgtttaag ccagtatcca   98280
cctcccagtt aatggaagaa ggacaggtta ctgaccttaa aatcaacagt atcttccttc   98340
gatatccaga cgaattcact gttaagatga aggtaaaga ttaccaatca gaaattaagg    98400
tcattactaa ggctactcgt cgtaataaat gggttgctaa tttagctgtt aaactcgcta   98460
agaaagaaga gaacgtattc ctgatgttta aaaacatcga acacggtaaa actcttttttg  98520
aaatggttaa agagcaacat aaagaagttt attacgtatc aggtgaagtt aataccgaaa   98580
cgcgtaatgc tctgaaagta atggcggaaa atggtaaggg tattattgta gtggcaagtt   98640
atggtgtgtt ctctactggt atttccgtta agaaccttca ccacgttgta tttgctcacg   98700
gcgtaaaatc taaaatcatt gttctgcaaa caattgggcg tgttctacgt aagcatgaca   98760
gcaaacaagt ggcccaagtc tgggacctcg tggatgatat gggagtccgc cctaaatcta   98820
aagattctaa aaagaaatat gttcatttaa attattgtct gaaacacgga ttggaacgta   98880
tacaacgata cgccgacgag aaatttaatt atgttatgaa agaggtacag ctttgaatta   98940
tcagaaaatt tacgatgatt taatagagaa tgctaggtcc agaggatgga ccaaagccac   99000
tgcgccctgt aaaatcgaaa ttcatcatat tattcctaag tcgataggtg gttccgatga   99060
ccctaacaat ttagttgcat tgactattag ggaacatatt ttaggccata taatcttggc   99120
taaagctcaa ggtggaaaat tatggcgggc cgcatttggt atgacatgcg gtaaaagatt   99180
aaatgagata agctctaggt ctatttccat tttaaaagaa aatgcttcta gattaataag   99240
cgaagccatg attggtaata caacggttc ttatgaatgg actgatgaac gaagagaaat    99300
acaccgaaaa gctatggcta agttggatt aacagaagcc aaattaaaag ctttagaaaa    99360
ggcttggacc aaaaataaag gctccaagca atccaaagag actatagcca aaggtctaa    99420
agcaatgaaa ggatttacac ctattaaagc cggagattat gaaacgtgtt caaagccgga   99480
caaagccaat aaaggtgtaa agaaatcatt taggtctgag gaccattcta aaaattggca   99540
```

```
agctactttg gctaagaaat atccacactg gttaatgtat gatgagctta aagagctttg   99600
gataaataca ggaaagctta agttggtaa atttacaaaa gaagccatta aagctggtta   99660
tcctaatgtg cattacggta aaatggttac caaattttc gaggaaacaa aatgaaaacc   99720
tttaaagaag ttattcaaga agcatctatt gaaagcttca tggctaaaat tggttcttgt   99780
cagactatgg acggtctgaa ggaattagag aagtattaca aaactcgtag taaggaagct   99840
gaacttcgtg attcggacga tattagcgtg cgtgatgcat tggctggtaa gagagctgaa   99900
ttagagtcga tggacgacga ggaagaggaa gatttctaaa caaaaaaggc ccaacctttc   99960
ggaagggcca ataaccataa atggctatac acactagact aaagtagtaa ttgggtttcg  100020
ttcagctgct cttcagtgtt ttccgtaacc ggcaagcttt gaacgtaatt ataacatgaa  100080
cccggatgaa ccggaccttt ttctgtttca acaaccaatg cagcatcgat tggagtttta  100140
cagacaacgc aaatcttatc tgacatgatt gtctccttag tttaacttac atatctattt  100200
attacttgct aaagcggcat taatgaattc ttggagaagt ttcattttat cagcatctac  100260
tttaataggt ttaatatttt tggtgcgcct cattttcac ctgcttcaaa tttcctgagc  100320
tccaacatat tctttaatga gaaacctctg gctttgactg cgtctaaagc tgaactacaa  100380
aagtcctgta ataaagccca atactggatt gacgtatcga ttttaattac actagaatct  100440
gcagccatta cagtctttaa ttcagacttc tcatactggt ccatacaaac ctcatcacca  100500
ggctctccac gtcccgtgta gaaatctaat cgcttcttaa gtgaggtctt tttctggatt  100560
tctaatctca tttttctt cttacaattc gtatacagtc ttagccatt gctgtgcagc  100620 aaaacgttgt tctgtacttc atactgtaaa cgagttccat caatctttaa atcttcatcc  100680
aaagcatctt gaaacgactc taacttgtac tcaatctctt tactcatcgc atgtttcctg  100740
tgtaataacc ataagaccat tatacactat tcaattgaac agcaattaac cactctgtga  100800
gagctgaatt ctaatttgct ctaatgtatc agggtcatca acgatactaa actgaacggt  100860
cacgataatc gagttatcat cgtacacagg ggtcacacct acggccaggg cagaaattct  100920
aggttcgaag ttccgcacag cggaaactat attacgctta atagtatccg tgattaatgg  100980
ggttatattc tcaaacaatt ggttactgat gtcgcaacca aattccggca taaagggcg  101040 tgaacctttg cgagtagtaa taatgcctaa caaactattt tttactgcac gagcacctgt  101100
agctttagcg acgtctctat tccaagacgt cctcatttca gggtctaaat ccgaatacat  101160
tttattgata ttcattacat caccttaaag aactctttaa gtccctcaat aacgtggacg  101220
gtatgttcac cacattcaca agaaataggt atggccaaaa taggcttagg ggtaactagt  101280
gcatcataaa cttcttttat atcttttct gttatcacag aataaaggtc atcaagttcc  101340
gcatcgctta aatcggaaag aaaaagcttt tcgcctgcag aagttaaaat ataatcgata  101400
caccctgcga ccatcatagc cctatttta tcttcaaaga gtttagggta cctgaaaaca  101460
attttaaagt tgccaaagtc tttaataaca tcgggctctt tacctaatgt tgcgcgagtt  101520
agtgtcatag ggacaacctg tgagcgacca caactacaaa cccactcacg ttctatattc  101580
acttcagcta atgaatgggc ccacaggttt atcaccagga gctcagattc ttgcttgttt  101640
aaatcacgag catctgtgca attcgaaatg agttcattga taaggactc tattctgcct  101700 tctaatttag cttggagcaa gtccttatac tctctgaggg taaatgctct gcattttatg  101760
gttttgtttt taattttac gtcaaaagta taattcattg tcttctcctt taagcttatt  101820
tataaataca tcaataagag gacaccctat ggctaatata gtacgttgtg aaatgcctga  101880
```

```
tggagtccac cgatttaaac cttttacagt agctgattat cgtgatttta ttttgattcg  101940
aaatgacatg aataataaat cacctgaaga gcaaaaacaa attttagatg agttactgga  102000
agaatacttc ggtgaatatc ctatgtcatg gcgcccgtat atgttcattg aactttacac  102060
gtcatcgctc ggcaagacca aaattcctat ccgatacact tgcagtaagt gtgaaaagga  102120
tagacaagtt ttattcaatt tgaaacaggc caagttagat aatcccacaa ttgaagtggc  102180
aggcttgaag ctaacattca aatttccgga aatagaatat cccgacaaat ctgaattgat  102240
tttgaacacc ctccaaacag tagaagatga aaacggaaaa tataattgga ctgacctttc  102300
tgaagaagac caattagccg taatagatgc tatagactta tccactttag aggatatagt  102360
caaacaaacc agccctatta atttcgaact caaatatgga tgctgtaatc gtagaacaat  102420
tgcgtatacc gatattttag aggtgtttaa acttatagtc aatccggatg agatattttt  102480
attttaccaa ataaaccatt tattggtaaa gaacaattat tcattagaaa gcattatgca  102540
gatgattcca atcgaacgcg gtattgcttt gtctttggtt gaaaaggacc ttaagaaatg  102600
agttcaaaaa ctatgcaacg tgaaggcttt cctaatatta gtatacgcct ttacgaagat  102660
tatgacgcct ggttagagca tcgttttgtt gaactaggcg cgacatttac tactctaaca  102720
atgcgagatg gactttacgg tagtaatgaa ggattgcttc agttttatga tgcaaagaac  102780
cttcatacta aaatggatgg cgagcagatt atccaaattt ctgttaagaa tgctaactcc  102840
gagcgtaccc agtcaagaat ttatggaagc aaacactttg ccgtaggagt ggattcgaag  102900
ggtgacaata tcataacaat acaactcgcc ccaatccact ttttagagaa ccttaaattt  102960
agtcgtatgt tctttccaag cgtacaagaa acattgacag aaatgattgg cgtaatttat  103020
caagaccgtc ctttacttgc tccaccattg aacgggataa acgtttatgt tcctaatgta  103080
ccatggtgcg attcaatgga ccgttatatg gaatttgttc gtgaagtagg tatggctatc  103140
gaatcagata aattcgtatt tgtatgggaa gatatcgatg ggctttctat tatggactac  103200
gaatttatgg ttaatcaaga gccaattaat tttgtggtag gtgagcctcg tttaataggc  103260
caatacgtcc aagatatgga cactcctatc gcatttgatt ttgaatggtt aactaaagcc  103320
aaccagcatt ccagaaaacc atatgaaaac gctactgtat acgcccactc tttcttagac  103380
aaaaacgcca cacgaattac ttttggtgat gggcaaaaca gtatattggt ttctcgctct  103440
ggtggatatt ctgattatac ctaccgaaac ggatttgaag aagccgatag attagttact  103500
atggcccagt atgatggtta cgctcattgc aaagtatatg ggaactttga attaaccccg  103560
ggtgataaga ttaatttcta tgaccctaaa aaccagttcc aatacgattt ttatgtgagc  103620
gaagttattc atgaagtgag taacaataca tcaattacaa acctttatat gtttactaat  103680
ggtaagccta ttaagattga agaaccaccg aaggttaaaa atgaacttaa aactgatact  103740
cccgatcaag aaaataacgc tgggtgataa agagatttct attcctaaat tgggccttaa  103800
acaccgaaaa ctggttaaag atgaaaaaga cccttataag gctcttcaca tattaatgaa  103860
ttccatttat aaaggtttat ccgcggcaga gaccgatttt gccgctcttc accttttaga  103920
attcaatgga agattaaaaa gtaaagtaac caaagacggg tttacttata acctaaatga  103980
cctttatatc tgccagcgac ttgaattcca attccaaggt aaaacgttta aatttaaatc  104040
acacgagcca tttcaaacat ttggtcctgt tgatagtgta ttacaatctc tttaccttgg  104100
tgatgacgta ccagattttc tggatatgcc tgcctttgtt gctacatggg ccgacgatat  104160
aacttctact atagctatcc ctggtcctaa tggtcctatc aaaggattgc ttaaaatcat  104220
ggatatctta aatgaagaac gaatctaatc agaatagttt tcgtcgcaat aaactgattg  104280
```

```
aagaaatggc tcctcagcgt cgtgctgagg cgctagccca aactcagaac gacgaattag   104340
gaaatatatc agatgtttta tccgattccc aggcggcgtc tgaattgctc tctgaagtgg   104400
ttgagacaaa gtccaatcag attattagtt ctgtagaccg agtagataaa agcgtccaag   104460
atgttgtcgc tggaacagaa ttaacagccg aagccatatc agaacaaacc caacagtcta   104520
aagctctttc ggatgcatta aacgaaaaga ttagtaagct ttctaatatg ttggaggcta   104580
aattttctgg tatttctatt ccaccggaag ggagctcatt aaaggttatt gaagactcta   104640
ttcctgaaga acctaaggct gaaactccta agttcctgc tgttgttgaa gatattcttc    104700
cgcccgaaga caataaacct gacgccgaat ttatgcctga gcctcctaaa aattcagatg   104760
aaggtaaaga aggtgataag acttctcttt ctgataaaat tgaagcccct actaaaataa   104820
ctgaaaaggg atttaaagct tctataggcg tcgctgatag aatttcaggc atgctttta    104880 agtataccat tactgccgcc gctgaagctg ctaaactcgc tgcaggttta gttctttaa    104940 tatttggtat agatgccatt cgtgtatact tccaatattt catggaccaa tttgaatcag   105000
ggtggaaaga atttaacgat aagtttaaag agtggggacc tgtacttgaa ggattaatga   105060
catgggccaa gaacgccgaa gccatgttta gtgaaggaaa ctggttaggt ctggccgaag   105120
ctattattcg cggtatggtt aatcttacta aaaatatggc ccagcttta atgctcggta    105180 tttctaagtt gatttctgct attttaagca aaataccatgg tatgggtgag ttggctgaaa   105240
acgtagaggc ttccgcttta atgtcgtacc aacaaaatac cggagccact ttagatgacg   105300
aagaccaaac taaagtggcc aagtaccatg atagacgttc tgctgaggct ttagaaacag   105360
ccgagaaaat gaataagaag tataaggata aacctgagct tataaaccaa gcagagaaat   105420
acggtaatct tactaaagaa caagctgacc aattacgtgc aggtggaatt gacacaagct   105480
tccgtgacct ccctgaagaa gaacgattag agtatttcaa gaagcgtgat aaagcccaag   105540
ccgatattat tcgtttgact caaactgctg ataatataat gaagcctgat tctaaagata   105600
tcgaaaatgc taaatcattt aaagctgata tcgagaaaca attggccgac cctattatgg   105660
ctaaaggtgg agcaccgaag gaccttaata tccagcaatt acttgataag atgaataaat   105720 cttagagaa atttaatgaa gctgaaaagc ctaaacctgc ttctgtagcg gaatctcctg    105780
aaaatactca ggttaaaaag gtggatgagc aaatgagagc aaaggaaaat gctaaatata   105840
gtcagcaagc tccaactcaa ataaatcagc aaacgaatat caagaaaacg agtaagacta   105900
gttataattt acctccacag tcttctactc ctgctcctgg tatgcgtcaa gctactaaag   105960
ttaattagga ttaataatga aagcaaaaga acttgacttt gatgtagcct ccttgtttaa   106020
aggaggctca aagacctccg ccggccagtc taaagctaaa ccggcccaaa ctacagtaat   106080
ggcccaatac ccggcagaaa gggcctccgg caatgacacc tctacagata tggtgttaag   106140
cgatttatat aaaaatggct acttttttac ggcgtataat tttagctctc gtgtatcacc   106200
tgatttgcgt aatgaccgat caagtcaaat gactaaaaag ttttcaaaag cctctagtaa   106260
acttaccggt aataccggag gattcagtgc ggttaaaaac ttgttcagta ataactctaa   106320
aggagttaaa tttgacaacc aagctttggc aaatatttta ctcccacgtt ctaaatctga   106380
cgtagattcg gtgtcgcata aatttaatga tgtcggtgaa tcattaatta ctaaaggtgg   106440
cggtactgct acaggtattt taagtaacgt tgcaagtact gctgtatttg gtgcattgga   106500
atctgtaact aacggcgtaa tggctgattc aggtgaacag atatacacca ctgcccgtag   106560
tatgtacgct ggcccggata accgtactaa ggtattcact tgggaaatga ctccacgaaa   106620
```

```
cgcccaagac cttatccaga ttattaaaat atacgaaatc tttaattact attcttatgg    106680
tgaaaccggc aactcagcct tcgctggtga attaaaagag aagattgata cctggtatcg    106740
ttctacgttt aaaaaagaag ctattgacaa gtttgacggt aagctattag gggaaagtat    106800
tacaagcttc ctttctaatg ttattgtggt aagtaacccg accatttggt atatccgaaa    106860
ctttggtgat agcagttcat atgatggtcg tgaagatatt tttggcccat gccaaatcca    106920
gagtatccga tttgataaaa ctccggacgg ccattttaac ggattggcta ttgctcctaa    106980
cttaccatct acgtttagtt tagaagttac tttccgtgaa atcattaccc ttaaccgtgg    107040
ctcactttat acggaaggat tctaatgtat actttacaag aatttcagaa ccaggcaatt    107100
aatattgacc tgcagaggaa taacctgttt agtgtggtat ttgctacagt tccttcttct    107160
aaatctcaag cgctcctcga ccagttcggt ggagctttat ttaacaatat cccattgaat    107220
acggatttgt ttggtattac acaaggagag ttgacccaag gtgttacgac attagtgaca    107280
gcgggcactc agaagttgat tcgtaagtca ggcataagta aatatctgat tggagctatg    107340
tcatccaggg ttgtgcagag cttactagga gagtttgaag taggtacata tctgatggat    107400
tttttcaata tggcttatcc tacggcaggt ctttttagtcc acgccgttaa atcccggat    107460 aatactttga actacgaaat ggatttgaac cataactcac ctaacatcaa aattaccgga    107520
agggaatatt ctccattggt attaagcttc cgtatggatt ctgaagctgc taactaccgt    107580
gcttttaatg attgggtcaa tagtgtccaa gaccctatta cacaattaag agcattgcct    107640
gaggatgttg aagccgacat tcaagtcaac cttcattctc gtaatggatt acctcataca    107700
gtagtaatgc ttaatgggtg tgttcctgtt ggtgtttcgt caccggaatt atcctacgac    107760
ggtgataacc aaattgcttc gtttgatgtt acatttgctt atagaagtgt acagacgggt    107820
gcagttggca acaagctgc ttatgaatgg ttggaagata aagtccttaa aggcgtggcg    107880
ggtataagtg agagcaattc actgagttct tcagtagcta aattaagccg actttcagga    107940
gcttctagtg gattaacagg attggttaat acatttggtg ggcgtgctat taataatgga    108000
atatcgaggt tgttataaca aaaaaggaga gcatacgctc tcctttaggg gtttatttac    108060
ggaacgaaat gaaacctgtt gcagtcatta atggctgctt tttaacaaat accgtaactg    108120
aaataggagc ttcggattcg agttgtcctg tcactacact gttaaaaatg ttttcggttt    108180
gttccggata agaaaaattc tcaacaggtc ggatatcaaa ttgcttatct tcaccgaaaa    108240
ctcggcgtaa ttcattacca atggcactgt caaactcttc agaagcaggg ataacgtttt    108300
caactaccag ttcttgacca ttaaaacgga atgcagattt catattgttc tcctcatgtt    108360
tgtgtaaggt aatagtacca catccatgtg gtgttgtaaa ctacattttg aatttatttg    108420
gtagagcaga gatatccaaa gatgcggcaa ggatttccat agcttcgttg ctttcagaaa    108480
cggattcatt aaccaagaat tgactgaacc catccatcag gcgaacttca ccagtttcca    108540
tcaaatggcc gccatcgtaa acagattcgc tgagctctga aggaggtgtt actgtagctt    108600
ccataaggta tttgtgagat actctatcat tcatggcaaa agccgctact ttatcaacct    108660
tcaacaataa cccgcgcgga aggataattt ctgcttcttc ggcatattct gtaaggtcac    108720
caggagcgat aactttaact gcttcagcac ctcgaataac cataccaatt tcagcaattc    108780
tatctgcagg accttcaggg gcaattggat taccaaactc atcttcttcc cattctacct    108840
cttcgtcatc gacttcaccc acatcagatg aactaccact agccaattta aacaactcat    108900
cagcggagga taagaacct tcaccaccaa caaaaacggc ttggttgtcg agggccatat    108960 aattttacc aaattcacca agatgttag gctttaatga ggctgacaca aagttcttaa    109020
```

```
agtaaaatgt tttgttatcg atattatgac gcagaatttt gtatggtaaa tcctgaccac 109080
gatacaaaat agtacccctta ggaagtttaa taccccttagt aaatgctgag tctaaatcct 109140
taatcaattt aatagccgtt gtattgtttt cggattcagg tttacctaaa aggaataagt 109200
tcataggagc atattcagct gcgcaatatt caataatggc attgctttcg tctttggtta 109260
ggtccttagg tttaatgagc tcacctgaat aagcatatgc atcactaata gaatcgttaa 109320
ttagtttata aacggcttcc atagcgaaag caattcgaga ggccttttct gaaggggagc 109380
ctttaaaacg ggtactcagg ttattaacaa ttttcttaat aatatccaga ctattggttg 109440
tattgatttg cgaaaggccg cttaaaagtc tatcgacttc tgtattaaaa aatgccatat 109500
ttttagagta aatttcaaac ccttgtttat ctctattagc ataatttagt ttaaatttac 109560
tatcagtcat taaagcgtga gtgagagcaa tggtgtatct aaagttggca aggtcctcgc 109620
tcttagattt aaactgagaa gcctggcgca ttttggtaat agcacctttt ttaaagttct 109680
gactaatctg ttcaataccct tcgttctcag ggccttcggc agtgtgaacc ggtacagaag 109740
cttcaaactc attataaacc tgcaattctt taggggacaa agtttcaggc tcagcagtag 109800
aatactgtgc ggctgctgcc atacgacggg aaatcttagt acgagtaata acagcctat 109860
cagtacgttt ctcttcaacc ttagcaatac ttgccgagac ggcttcaacc ttacttacag 109920
actgacctgt tttcttagaa acataaactt caccgacttt agaatcgact ttggtataaa 109980
ggtcagcatc aatttcaggc ataccttga tatcttcaat attagcacca cgacgtacta 110040
aaagaacgta ggtatgttta ccactgaatt ggaacatgtc atcaacaact ttaaacttgc 110100
cgccggtacg agccatcgcc aaacgagcta atacgcgctg aacagtagga cccttacctt 110160
tcattttctt ggtagggaaa cggaataaaa ccgcatccat tttaagtttg tttacttgtt 110220
catatacggt atcgaaaatg gtattcagtg taccaagcgg gtcagaacca aggccgccct 110280
taagttcagc cggagcaccc ttgcttgaca aactcattag aataacgtgg acatatttgt 110340
cgcccggctt aaccatttta atagcgtctc cttgagacgc ataagatacc atacgagcaa 110400
ccaggttatc gttacctggc gcttggatag agaaaatctg tggaataccg gaacccggtt 110460
taagatttgt tactggatag tttttttagcg gaatcactat caaaaacttc gtttaaattt 110520
tccattattt acccttgggt gaattttttct gggacattgt aaaggtccat acaagatgct 110580
aaaagaggca acacatcaaa cttagttgat tttacaaatg agtcaaaaga tacaggattt 110640
tcaatagtat caaaatcatc ttgatatgca accaattcgc cggtttccat tagtatgttt 110700
ccatcatata ccactgactc ttgaagctca tctgatgtca taacttcggc ctgaactaat 110760
ttattattag ttttagcagt accgtcatta taagaagcat ctgttatttt attaattttg 110820
agcattaacc cacgtggaag aataatttcc atttcgttgg aaggagcaag acctgcacca 110880
gggaatacca cgtttatttt gtgagcacct gaaatagccc aaccaatacc aacttgatcg 110940
tcattagact taacaagtcc ttcatctgat ttgtctatgg aaacatctaa acggacatca 111000
tcaggcaggg taccgattgc cgcatcagtc atccaagtac cgaaaatatt tggatataaa 111060
gatgtagata caaagtttct gaaatagaat accttgtttt taaccattgc ttcgtaaata 111120
ggtggaatca ttttctgaga acgatacagc gtaattcctt ctggtaatct atcaccattt 111180
ttaaaagcat catctaggtt atcaatagct ttttcgattt ccgggcggt tagaatacta 111240
gaacgaactt ctggattgta tatcccaaa agagcattat tcatatcttc atagcccgag 111300
ccgacatatt cacggatacc acgttttttgt gccggagtat actgagtttc atctcggtta 111360
```

```
tcaacaatag agaacattgt ccaacctgcg gctaatgcaa aaccacgaat ttctttttta  111420
atgaccttag tcttagcggc attccaagag ctttcagaaa gttccattgc catagtataa  111480
tctaaattag aatgtttcgc aaagaattt cctaaccaag cacctttgta ttcttcaaga  111540
acttcgttta atactgaagc aaagctgctt aacgcatcca tagatgttat aggcttacca  111600 tgaattttt ggaatgcccg aactttaaca tcatggtcaa cttctttat tttacctta  111660 gttactattc cactatcagc aaaagcgtcg ccaacaccgt ttatatttgt gactgtatta  111720
agaacacttt ctaaggaaaa tgatgcagta gaaatagtag atagttcatt agattctgga  111780
ataagtggtg cggtagccgg tttacttaat tcagaggcag aagcttcaaa tttagtaaac  111840
ataggagttt caaaacgtgc agattctaag gattgcgaca tagcaatagc acgacgtgaa  111900
atcttagtct tagtaataac agttttatca gtacgacgtt cttcaacctt agcaatacta  111960
ccagcaatag cggtttcttt agtaacctgt acgccttctt ttttacttac ataaacttca  112020
ccgacatcag aatcaaccct agtataaagc tctgagttaa tttctgggat gcccttaatg  112080
tcctcgatat tggcttgttt acgaactaca agaatataag tgtgtttgcc agtgaattca  112140
tacatcgctg gaatgacttt aaaacgtccg ccggttttct gtgctaccaa acgttggata  112200
atacgttgaa cgataggacc ttgtcctttc attttcttag tagggaaacg gaacatcaca  112260
gcgtccatac gaagggcttt aacctgatcg tagacaacac taaagattgt attaattgca  112320
tcaataggag tgggcccaag gccgccttta agttcagccg gagaaccttt agccgataaa  112380
ctcattaaaa tagcatgggc atatttgtca cccattctaa cctgtttaat agcatcgcct  112440
tcagaggcat aggataccat acgcgctact aattgggact ccacgccgcc aatcttccaa  112500
atctggggta ctttaagttt agggttcaag tttactgtag gcagggtgcc ttcggactca  112560
aacacttcat ttaattgttc ggtcataata attcctcttt aataaccta tttatgccat  112620 aaaaggcccg aaggcctta ttaaagtact aacaacgtac ggtacacttc aaatttagga  112680
cccttttcat agcggtcgaa attatcttta aaatcagcga acgcgatttc attttcaaat  112740
tcaaggacaa tttgggacac tgcggtggag acatcgccac cttctttata tccaataacc  112800
acggtttcta aataagcttt catattatag tccagtttga gaccaatcac cgaatacatc  112860
ctcaaatgta tcagcttctg ttttatcgaa acgccaacct ttaataattg gaaggaaaat  112920
acctacagta tcggtacgtc ctttagaatg aacccaacca ttacattcac agtcagcaat  112980
acggccaatc aacttgcctt cacgagcttg tttcataaga agttcacggt ctaaatcagg  113040
acggtcttcc aatggaatca ataccttttt acctgattta tctttcttat gggtggtatc  113100
tttaaagcct gagccacagt cacttgtaat tcgacggcaa cgtgatacta attcaacacc  113160
gccaagtttg ttagggtcct tagagtgttc ataataacct accacttcta aagcgatatc  113220
gattacttct ttgaacttga taagattctt agaacggcgg ttttcccagt aggagtccat  113280
gttcttaagg ataatacctt ccagaccttg gtcgacatat ttcttataaa cgactttagc  113340
ttcttcaaga ttattaaccc actggttttc gatagcttca acacgcgttg tgccatgcaa  113400
tacgacatta tgagccacca taagttctaa ggccgcaaag cgtacatcat acttatcgcc  113460
tttaatttta ccttcggaat atacgacatc cagtggaaca taatcccacg cctgtaatac  113520
catacctgct gcttcggttg gagtaatagt tccttgaaga gccttgttag ccaagccgtt  113580
tgacgtggaa cgatcggcga cagttttgaa ttccttagcc ttacttaatt caggaagttc  113640
ctcatcaaac atactaaaca aatcattgga tgctttaggt tctaccttag gagtatggta  113700
aactaattcg ccgtcaatca taacaccatt aggatgacgt tgtcgggctt cttcggtcat  113760
```

```
gaccatcaat tcagcagcca aaagattaag cccttgatat tcgttaccac cacgagtaag   113820
gaatgtcaca ccatcgttac gaacttcggc aaaacaacga gccccatcag cttttaattg   113880
agcaaacgct ggccatttaa tattttctt aatcaaatct tcatcataag aactagccaa    113940
catctgtggt tgttcaggga ttaaaccttt ccaaaccttg ttagcaatag aaattgatgc   114000
accacattca aggtcacgca tcattacacg acgtaatacc tcggcatccg gggccttagc   114060
atcagcaatg atttgagcca gttcttcaat agccgcatta cccgtaatct tacgtgtggc   114120
taatgtgaat tcagcgaaat caagaaggtc ttcaagagta atcataccaa aggattgaga   114180
tataaatcca ggttctggcc actttttaat accgtagttc agacgacggg tataagccat   114240
acgataaaca cgtttcagaa gctcattgtc cttttcacga gcaataatgg cttctttagc   114300
tttagtagaa tcgatagcag caatttcgtt caagatatct aaaatcataa tcacctcatt   114360
agtcatggat tctattataa gccacatcag ccaaaagcaa gtctaatcgc ttatgataag   114420
agaacacaaa tctcattcgc ccatcggatt tgaacttgga cataaagtgg acataaatga   114480
atccctgttc gacgcattcg cgccaaacag gatggtcttt agccggattt acatcaaatg   114540
agtaatcatg attcacatga cgaataaact ggtttacatg accataatcc attgtagtgg   114600
taggaccata gtctgaaatt gtatgaacta caaacatatt aacctcgcgc aatccattca   114660
actgcggcat tattacgaag ggattcgatt gctgctatat cgtcccatga attaaccttt   114720
acggccaaat taggtttaaa gtcacgttca ccacgagcta accaataaac ttggatatcc   114780
atgagaacat tagatgcggc atcacagtga tgagccaaat catcaacata aaacttaata   114840
cgtttgccgt acgtattttt agctctaatg aacaagtctt cttttgattc tgaatgtcca   114900
cacatcagaa tctccttgaa tgcgccaggg aacaatgcat tcaaattgaa ttgtctattc   114960
agcagggcat caattgagtc gcctagcgca gtcacggcta caaaatcgaa gtctttttg    115020 agcctgttga tgtgttttaa tgcgtccatg taaggagaca gataacgaat aaaatctgac   115080
tgattatatt tctcgattaa acgagcgcct aattcgttgt cacaattaaa cagctcacca   115140
ggagataaga aacgttcgtc ctgaatcata ttcaaaatat gttctaaagg caaattatat   115200
ttctgtgcga ataaggcaa gccagactgc caacttaaac atactccatc gatatctgtt    115260
aagataactg gtttcataat aaatctctca atttgtttag gatgtcgata aactcttttt   115320
cagttagtat tgtatcacat tctgtaaggt ggcttgccat agaatgcttt aaaacccctac  115380 cttttgtgga ttgtaacgca tcgcgaaatc ctttgttttg gagcgctgct tcaaaatacg   115440
cactttcgta aagctctttc catgcttcgg aatatcttga aaacggagtt ccaacccaga   115500
acaacgtgcc acggtcctga gctctagcat aagctcgtcc agcttttgc gcgtccaacc    115560 cggacatccc aaatatacgt ctttgttgtt catgattttt caccttacac ccttggagga   115620
acccttcgag accaccaaat tggataccat ccataacgaa aggccattta gcaaagttac   115680
ttaatgcgca tgatggccat gggaaattgc ttctgatttc taattcagac atctttgaca   115740
cttataattt caacatcagc ccaatgacca taaccaggta gacggtcttt aatagacaat   115800
ccaccgtcag atttcagcat tttaattgtt ttagtatatg gttcaatatt tcgggcccat   115860
ggactcacgt ctgttacacg ataagtaact tcaaccattt ctgttcccaa aattttctga   115920
atcagtttct taaacatatt atcctcgctt taaacatttg attacagaca gttcaccgcc   115980
catacgaaca tcttcagttc catcgaccca taggacggtg taggcttctt taatagtaac   116040
attacctaat ttaaaagcag gtagaacctt tgaaatcatg ccaggaatac ctataccttt   116100
```

```
taactggact gtttgtgata agaatagttg cattagaacc tcatctgaaa gccatgtgat   116160
ttaacattac caccatagat gtcggacgta ttgacttcac gtgcagagct tgggtcgata   116220
ttgatatcat ggttgagctt agtgattgct agggtatcac gaccattaac agtacggaat   116280
tctaccgggc atacaacatc ggcgtaagcc ttaatagatt cacgagtggg ttgtttgtcg   116340
gcaggaacgt ctttacctgc tttagagaaa acaacttcac agaaatttttt acgagtatca   116400 aaataagtgg tcataaacat aatatttttcc tcaaaggagg ccgaagcctc cattttttaag   116460 attagatatc gaattcgttc agaactacat caaagattgc ttccaggtgt tcaggtttag   116520
ctcggttgct caggatgtga cgaatccagg ttttaaccag aagcttacga ttaacgccgt   116580
tccagcaagg atgggtacct aaatcacgtt gacggaaatc atcatctaaa gcgattttaa   116640
aagtagaacc ttccattgtg attgaaaccg taatgccgtt ttcaaagcgc atataaacgt   116700
agttaggagt catgcactgc tcgatttcgc acactgtacc gttgttgtgt ttccacaggc   116760
aaataacttc agaagaacca gcgataccgt tagaaacata tttacgttcg aagttgatgt   116820
agttcatttt attctccagt ttgttttcgt attatttggt acaggtctat aataacacaa   116880
cctgtaccaa agtaaaacat ttatttcaca acattccaat tttttcatatc aagtttacca   116940 actttttttca tctgagcaat cagacgttca gcacgtgtac gggcattaac gtaatagaat   117000
tcaccaattt tgttttcttc aatacgaccg gtaattacag ttttcagttc ataaatccaa   117060
cctgtaaaga agttgtgaag ctcgatggtg aatgtgaaat cagtacccat accttcagtg   117120
gtttcgactt cgatgatatc accttcaact gcagtcagga cccacatggt ttcttgatat   117180
tcaccgttga aacatttagc tttaacagat gcattaagat ttacagtttt catttttattc   117240 tccagtttgt tttcgtatta tttggtacat gtctatagta tcatgcctac tggagatgta   117300 catactttttt tgcaaataaa acgaaaaaag gaacccgaag gttccttact taatgatgat   117360
acgaggatta agctctgccg tgtagtaatt tacagcctta gtaactatag cttcacctttt   117420 aggatttgcc agaacccatt cacgggctcg tttgtgagct tctaattcag tcaataatcc   117480 ggaccttttga caccctctgt cttgggtacc tgcttctgtt aaaaaagcaa ctaggtaaat   117540
cgcgttttca taaggcttgg cgggcggtac gtatactggc gggttatatg ccgcgggatg   117600
atgtgccgga attccatcat acggccctat acctggcacc gcgtaagagg caccgcgcgg   117660
agaagtaaat gtatgattat atctatcgtt cataatattt cctacaaaaa tgggactccg   117720
aagagtccca taacttatgc ctgaggctta ccaaagcaag cagcatctgc acgtagtaca   117780
gcacgagcac gagcttgaag ttttttcaacc aactgattga tacgtgcgtt agactcacgc   117840
ttgtagccag cgcgtttaga ggtaccatca attactttaa cttctttctt agccattttt   117900
aaattctctt aaattagaat gaaggactta ttgacattgc cttcgcaagc cctctatggg   117960
gtacttaggt ttcggatatt taacgacagg ataaccataa acctcgtcaa cattcaagag   118020
gtacaccgta aaattgtcgg ggcggtactt ctaaaacata ccgattcgta aatcgataat   118080
cagacaattc gacggctcct cgatttttact tcagggtaat aataaaatga cgtactgctt   118140
tacgagctgc tgaagccaaa ggcttagcaa atttcagttc atctttagct tccagttcag   118200
cagccagagt agcctgagcc ggattcagat gtttgaaata acgcaggatt tccagtgctt   118260
cggcttcaac atcaatagag gcgccgtagt tttcgtgacc gttgttccaa gcgttgcgtt   118320
gcagttcaag agcgtgattc agttgtttgt tcatttttagt ttctcaattc gagataaaga   118380
ttggtggaca cgttcgtctc agtattccag ctgagttgta tctcgccgta tggaagaggc   118440 taacccccata caccaaccga agttctgtat gacatcaacc tcttcgtaat tttatttata   118500
```

```
caagcaagga attgctttat agtggcaggt aacgaatttt tgtttaattt ctttaggctg  118560
tttaataccc aatgcaacta aaggatgagg cacgttagca atcttaccaa caggaagtgg  118620
agtcaaatcg cctacttcac aaaaaccttc agggacatca ggtcctacag aataaatttc  118680
acaaagttca gggatttcac cttgatgaag tttgccaata acgataccag atgcagtagt  118740
ttcttcatca ccagcttgtt ttggttcgga aacgagaata acatattctc cgaccgcttt  118800
aataggaagt tccatattta atccatattg ttttgttgat agattaataa taacacgcta  118860
ttcttaaagc atattatagg acaagcagag tttcggtctg aaggccatta acagaaatca  118920
gcttatcgaa acgaatgaa cgccaatcat taaccttggt atcaaatact ctgatataat  118980
taacaggttc tttattggct tcaggtccag gggcctggac ttctttatat ggaagcaggt  119040
ctaagtcacg tgtacaagtc atacgacggg cactaccatc agcttttca aacaggactt  119100 cgtgagtacc tacagacaaa atagtcttga cttttttcacg gagacgaatt gtttcttgtt  119160
cagttaaaat cataattatt ccagaatagt tttgatagtg gttgcattac gctcttttag  119220
agctcttaat aggctatggc aattttcaag aataggtact gttttgtagt tcatgttggc  119280
ataaacccac tcagatttat agtacgattt ccatcgagag aaaaagtact ttttatattc  119340
tactgaatag gccaccaggt tttcacccttt tgagttcaga cctgaaaact taactagacg  119400
aaatttcatt attcaccaca atagttttga attgattccc agttcaaaga acggagacct  119460
gtacgattat actggataac ttcgatgcct gattcacgga ggatatcgtc ccacccttca  119520
ggatttcggt catagagctc agcataaacc aatgttttaa ttccagactg cgcaatagac  119580
ttagcacaat cagcgcacgg agataatgtc acgtacatcg tagcgccatc aatagaactt  119640
ccggtacgag cagcaaacaa aatggcattc agttcagcat ggatttcatt tttagatgac  119700
catgcagcgt gagccatacg gtgttcttta agaagaacag atttatgcga cattcgagcc  119760
gggtcataca caacacgagt ccagttctgt tccacagcat ggtcacaaca gttaacacca  119820
ccagaaggcg aaccgttata ccctgtagaa ataatgcggc cattcttttc aataaccgcg  119880
cccactttcc atgaacaaca ttttgattct tgagaaatca gatatgcaat ctgaagatat  119940
gtgcttgctt tcattctacg tacactcgct gtgcttcgac caaaccatct gaaccgagtt  120000
tcaactgggt aatttggtcg ccattttag gattaacgat aaccaatacc gcgcgtggag  120060
attcctgaat tactcgcaga gttgcatcag gaaaacgtac agaaaccttta ttaatcaggg  120120 cctgagcaaa ttctttaact ttaacgtgaa actgctctac agtaataggt tgttcgctca  120180
gcattagatt gtctccaact taagttgttt ggtagtggta gctgggtaa cgtcgccttt  120240 aacaatataa cacacttgtt ggaacgaact ggtcaaaagc tcttcagcct gacgatcggc  120300
ttgttccttt gtgttatggc gagaatgaac ttcaatctta ccatttttaa caataagcac  120360
tttccaatcg gccggagttt taataggttt gatttcaggg ttctggaaaa ctaactgcag  120420
ttctttaggg tctaccactt cgataaagta ttcgaattca tggctaaaaa agcccgctga  120480
attaaaaaga acactatttg catcgtcagg attacccgtg attttgctca ggtcgacaaa  120540
catcatctcg tcatatacac gaattcggct tacacgttca tgaccattat gataatcaat  120600
ttcaacttca aacggattca tacccacata cttagcaaaa gctgtattga ggccataagc  120660
accgttatta gtgaatttgt ttttggtgta ttcaccaacg aacttgtaaa acttacgctc  120720
ttcaaagaac ttacccatt cgatttcctc atttgtttcg gtaaggtcat catatcaccg  120780
tccttggtga aagtaaacac ctttttttaa atagcttcga caactaccgt tgtttctgg  120840
```

```
aagtccattt tgcatgaaat agccaaaatg tggttatcaa ttttaaatgg aacgattgca 120900
aatgctgcac cgggcgtgag ttgaacagtg attgcatcaa ctgcatccgg aacatgatt  120960 tccagaatag cagacaaacg accatgtacc tttagttcag tcgacgtgtc gacgctttcg 121020
tatagataat cagatacaat ctgactaaaa actactttaa caatttcaga ataagtaggg 121080
aacataatta cctcagtgta cagtatggac tttaacgtta acaataaacc ggtcaacgac 121140
ttcagtcaga ggaacaaact caacatagta ctcgcctttg taacgttcat tgaggtcatt  121200
acgaagggcc gcaagtgagt taatgagggc aggagacata ttcagaccta ccagtttctg 121260
aagctcttta taagcttctt cttcaacttc atggtgtttg ttatacataa tgttcttcca  121320
agaaggcaag gagttcagga gcggatttaa aaataccacc atcgaccttg tcttcatctt  121380
tatagtccat aacatccagg ccaatacgtc catcagttaa aggccatacg ccgaagaaaa 121440
agcatttacg ttttcaatt tcttcgattg tacgaaaaat cttttcgata ttattcatta   121500
aaagtcaccc gctgcgactt gccaacattc aacaccaatg cgccgccaca tttccactac 121560
ttgggtacgg tcatcaatag ctaatttaac atcaaagtgt ggagcaattt tttcccagaa  121620
gatttcttct ttaacgatgt catctttacg gtcgtcacct tgttcgcgtt gacattgcat  121680
gaccaatggt acaccagcaa agtcctcaac ccatttgcga gtcatacgat aatatttcat 121740
tgggtcttct tcagtgccac attcgcgacc gcttactacg ataatctgat aacccatatg 121800
ggcatacatc ttagacagtt caactaccat tgggttgatg acgtcagtat cacacttctc 121860
aaggtcgtat ggactacggt ccgccatttt ggctagtgta ccatcaacgt caaaaataac  121920
ggctttaggt ttgccaggag tccctgtata accggaagt  ccaagataag cccgcatatg 121980
actatacatg gaacgcagaa cgtcaatagg tactgctttt gaaccacggc gactgttacg  122040
tttaaccagt tcagtccaag gaacatcgaa tactttatat tcaacttccc agccatattc 122100
tttagcaaag gttttccaca tcaaacgacg ttcaggattc aagttggtgt ctgaaataat 122160
tacgccctta acagaatcac caccatacaa aatactctta gcagcatcga actgcatgca 122220
agtcacgatg ccttctttct tcttggagta tttgtattca tcacgggctt catgacccat 122280
gattgattgg cgatagtcat cacggttgat gttaaaataa ccagggttct tagcaatgaa 122340
ttcacgagtc catgtgctct taccagaacc agggcaacct acagtcagaa taattttctt  122400
catcatttaa ttcccaacag agttttgagg agctgaatgc gtaattcaac acgcccttta  122460
tttaattcag ctactgcctt gttgcttgac ttgcgacggg tattggcaga gatgaacata 122520
attaaatggt tctttagctc acccatatcc acaccttggg ccttagcagc cttccgcaga 122580
gccttgcctg catcatctaa ggcttttgca gggtcttcgt cattcaagac caatccgcgg 122640
tctaaatcca tatatacagc gccatggcat gaatcaatat aattgtcgga gcacttgata 122700
taattctcta ataactcttt catacaccga gttccttata aagttcttca cggcaagttt  122760
taagagtttt acctgattcg taagcaacac tttcaggaac atcgccaagg gttactgcgg 122820
attgcatttg accatggcgt ttagccgcat attcaaaact tttcactagc tcacgaatac  122880 gttcttttc attgtattct tcaatgaatt cagggtattc ccaaaccgga cgcatcatac  122940
gataccattg ttggatggtg atataattac ttccatccag attaataatt tgcgaaggct 123000
taatagaccc tggagcataa aaagttacct gtcttactac atcaataccg tccaccatag 123060
cccaagcaaa atcgaaagtt gccttctttt caagtggtgt acttgcacag gaccctagct 123120
taaggagttt ttgtaatgca ggagatttaa cgcctgaaat gtactcagga ttagccacaa  123180
aactgttatc gcgtaaagtc ataataattt cctcaaattt tataatccgt aggagcatta  123240
```

```
tactctgctc ccaagagttt gtaaactact ttccaaaaag accatcaata cacatactga 123300
acgcaatccc gaagcaaaag aatgcgatag ctaatctaac ggcatcccaa ccaagactac 123360
actcaatcat ttgcacttct cctcttttag tccggaacgg taataacata acatagattt 123420
ctggtcttgt acatatcttt ttacgtcatt caaccaaata cgatgttctt gggaatcttc 123480
aaatggcatt ccaacccaag ctttaccatc gattacctta acctgccatt taacattatg 123540
ttcggcaata ggttgtggcc atgaaggatg cagttgttgc ttaggcacta caggaagctc 123600
ctgagcacat ccggctaata agccaataga taatactact acagataatt taatcattct 123660
gtaatgctcc tgaagtcttc tgtaaaggaa tcgaaggact tgttgatttg tttttcgacc 123720
agtcctggct tacttgccac cacgtgcgcc ttcttcgaat ctttacggag cttttcattt 123780
tctaccttaa ttttatccat tcgggcattc atttcagtag tacggaattc aatatcgag 123840 tattgaccac gaaggtcatc tacggcttcg gcattctgtt tagccgtttg ctgggtagtt 123900
ttcagttctt cagtaagggt atcaatacgg cttgattgat acgaaataaa accgtaagca 123960
cctactgcaa tggctccagc taaaaggtaa atacttaatt tagacatttg gtaataatct 124020
cgatgatgtc atcacgtgac agggaattaa taagaaccgt tttaggattt tcgcactgaa 124080
ttttgtacgt ttcgaacata aaacacaatt cttcagcggt atggtaagga cttgaaatgc 124140
caaggcgatt aaacttgtcg cttaatgggt cgcaaatcaa atagaaagtg atgcctgaga 124200
ttttgacatt aggttggcta atattaatga ataccctcggc atcgtacttg gaaaggttgt 124260
tttggagaaa ctcaaccata gagttgacag cttcaggcat ggcttcacgc ttttcttctg 124320
cataacgggt agagtattct ttttgcttga ttttcttttt agcattttta gctaaagtac 124380
cacgaagatc ggtcaggtaa cctacggcac gagaaccttt aaaaacttgg ataccgtcag 124440
tagagtcacc aaaagcctta acaaccattt cgttagtaat catttgcata ttcattttgt 124500
tttctcctca ttagttggta agtctatact aacacaacat gaggagatgt aaactactct 124560
accacaattt cttttcaaata ttttttcaggg atttgggctt tatggttttt caagaacaca 124620
gagttaatct ggtctacaac cgtatcataa ttaataccgc ctacgtacgc ctgcataaga 124680
atagagaaca accctgggaa gtccttaagg attagctgtc cagtaacggc gtagtcttta 124740
cggtcgcgtc ccttgagttg ggaatacgct gcttccaaca aagccagtga ttgttctaga 124800
taatctaaat gaatacgttc aaaggcatcg attttctcta tagcaaacga atccgtactg 124860
aacaggccac gaaggtcgtc agttccacca gccactacaa cttcaaacaa acgttcgtta 124920
ttgttaatgg aatctttggt atgatgcagc gcactgtacc aagcggtttt gagtttaaag 124980
aacgtaccat ctttcagtac aaagatgaaa ccttcaatac cctcttgttt acggatgttt 125040
tctacgaaat caccttcaga gagttcatag cttttaacca aatgcttacg cagtgcgccg 125100
tccttaaaca gttcggcgta tggaatatat tcacctgttt cattattacg aacgttcaac 125160
aggatgaggt ttgtttcttg gtaagccaga acgatacggt tagtaggagc gacgtactca 125220
aggttgcatg tatatcctgc tttagtaatt tcttctaaac gggcagcgaa ggcctcgttt 125280
tcagggagac gaaggaaacg taaagaatca tgtaccattg atgaatggat agagccttta 125340
gatttaacag aaagatattg tctgtccatg aaggtagaaa tcaaggaacc atcttcctta 125400
gccattacga ggtcaatatt ttccggcgac aaatccagac cgatagtcat agggttttcg 125460
tcaaggttaa agaacttttg cataggacga gcagcaatac gtactggacc gttctcgtcc 125520
atttcaaaca taatgcctcg acactctagt gcgccgtcct ccaaccaatc actgtatgat 125580
```

```
gcatagttat aactaaagat gcgatagttg actcctagcg cactctgaaa gtctttaaag    125640
aagaacttag atttagtcga gttttaacc agggccatca agttatcata taattcaatc    125700
attgcttatc cttttaatcg gtgttgggta ttccaaggtg gattaaattt ctttatgaac    125760
attggctctt caagagacat ggtctcaact gacatagttc caagttcgtt agtcattgac    125820
agattaaagc actgccgtgc atagaactct acctttttac ctgccattaa tgcttcatga    125880
atcagaatgg acttagtcga atctgacgtt tggtccttac gattaatagc ggttcggtag    125940
tagttgatgc gcttacgaag attttagtc ttcccgacgt agactagtat atcatcaacc    126000
gctatagcat atatgacatt ttgtttattt ggtactgtga gtggagctat ggtggcgtca    126060
tcttggagtt ctagggtgac gtacttgata aagctaaatt cgtctgcgat ttctttcata    126120
gcaataaggg gccgaagccc cattccttaa aaatatctct tgtacgatgc cattactttt    126180
tcatcgacat cgttatcaat ttgtgctaca aggtaagaac tgatttccac ttcctgagga    126240
gcagcctgta cagcatcaga attcaggtat tcgcgaatcc aaggatacgg atggcgagta    126300
ggagcatcag taataggaca tggtaagccg cattgtttca tacgagaaac cgtcaggtaa    126360
tcgacaaaag cacccatgtt ctgagtattt aatccagggc aagtaccatc tttgaacagg    126420
tgagcggccc attcttttc ttgacggtta acttccatga aatatcaac tgcttcttgt    126480 tcgcactctt gggcaatttt aacccattca tcgccatcag taccaagttg aagttgacga    126540
ataatgtact gagtacctt aaggtggagc tgctcatcgc gtgcaatgaa cttcataatc    126600
ttggcattac cttccatgat ttccatgttc ttatggaagt taaaggtgca tgcgaaagat    126660
acgtaaaaac gaatagcttc caaggcgttg attacgtgca ggcagaggta aagagaacgc    126720
attagttcat atttggcagt tttaacacct tcactgaact catggtattc ttctaaagca    126780
ttttggtatt tacgtgtttt ctcaataaca tcgtcgtaat aacgaccaat ggattcggcc    126840
cgtttcatga tagcgtcatc taacagaatt tcatcaaata ccttcgatgg gtctgtatag    126900
aggttgcgca tgatatgagt atatgaacga gagtgaatgg tttcactaaa tgtccatgta    126960
gccacccatg tatcaaggct agggtccgaa atcaatgctt ggagtgcagc agaagggggcc    127020 cgtccttgga tactgtccag aagtgattga tacttcaggt tattggtaaa atatttttgt    127080
tggaattgtg gaagcttatt aaactgcgcg gcatccatca tcaagttaac ttcttctggg    127140
cgccagaaga aactcaactg cttttcacaa agctcttcga atactttatg gcgttggata    127200
tcgtaacgag caatacccaa tcctgaacca agaacatag gttctgttaa aacatcaact    127260
ggggtggtat taaaaactgt agacatatta ttctcatttg ttagtgactc atccatgagt    127320
caattataat cagagtttct taaagcttac aagctgcaca atcatcggct ttaggggttt    127380
cgatttcata gtcatcggta ccggagccat cacgggtatt atgataatag agatttttc    127440 cgccataata ccagaaatat agcaggtcgt caagcattac agacatcgga acttttcctt    127500
ttggaaaaat ctgtgggtca taatacgtgt tagctgatgc agattggcat acccatttca    127560
acataatcgc cacttgggta agataaggtt tattaccttt cttagcgagg gtccaagcat    127620
aatcatacag cccttggtta tgttctacat taggaactac ctgacggaag ttaccttctt    127680
tagattcttt aatacttacc gggccacgcg gaggttcgat accgtttgta gagttggaaa    127740
cctggctgct tgattcgcat ggcataagtg ctgataatgt gctattacgg atgccatgtt    127800
tagccaagtc ttcccgcaac gacgtccagt cacaaacgta ttttggagct gcgatttggt    127860
caattttttt attgtaccag tcgataggta attcgcctcg agaccattta gtgtctgaat    127920
aatactcgca aggtcctttt tcttcggcca gcttgattga tgctcggata agtccatatt    127980
```

```
gtaatctctc aaacagttca tgagttaaat cgttagcgtc ttcataagaa gcaaagtttg 128040
aagccaacca agcggcgtag ttcgtaacac ctacacccag gttacgacgt ttcttagcct 128100
tcagagcttc aggaacagga taatcttggt agtccaacag gttatcaagt gcacgtacct 128160
ggacttcagc aagttcgttg attttgtctt ggtcttgcca atcgaagtta tccagcacaa 128220
atgcagacaa cgtacacaat ccgatttcag cgtccgggct attcacatca gtagtcggga 128280
tagcaatttc acaacacaag ttgctctggc gaataggagc tttctcacga ataaatggtg 128340
tgaagttgtt agtgttatca acgaattgag gataaattcg tgcagtgcct gaacgttcag 128400
tcatgaacaa ttcaaaaagg tcacgtgcct taatacgttt cttacgaata ctagggtctt 128460
tttctgcagc ttcatacaat tcacggaaac ggtcttggtc ttcgaaataa gaatggtaaa 128520
gctcaccact catttcatga ggactaaaca gagtaatgta atcattttg ccgaaacgtt 128580 ccatcatcag gtcgttcaac tggattccgt agtccatatg acggatacgg ttctcatcga 128640 caccctgtt gttttcaga acgagcagat tttcaacttc caaatgccaa ataggataat 128700
aagcagtagc agcgccgcca cggattccac cttgtgaaca tgatttaaca gcagtctgga 128760
aatgtttcca gaacggaata acaccagtat gtttgacttc acccatgcca atacgagaac 128820
cttcagcacg aatcatacca acgttgatgc caatacctgc acgtttagaa atgtattcaa 128880
ttattgagtt agcagttttg ttaatagatt tcagtgagtc gcctgcttca ataaccacac 128940
aagaactaaa ttgacgggtt ggtgtacgag cccctgccat aataggcgta ggcaacgaaa 129000
cctgacgagt acttacagca tcataaaaac ggatgatatg agctaaacga ttaccaggtt 129060
cttcttggtg caacgccata ccaatacaca taatagcgaa ctgaggagtt tcgtagattt 129120
taccggttgt tttatcttta accagatatt tctctttaag ctgcatcgca cctgcatatg 129180
tcaattcaaa gtcacgttca tgcttgatat gagattctaa gaaagtaatt tcttctgcag 129240
aatatcgaga cagcaattca gggtcatatt taccttcgtt aacacaatag gaaatatggt 129300
cgataaaact acgcggttca aactggccgt aaacttcttt acgaagagca aacatcaatt 129360
gctttgcagc aacgtattgg taatcaggct cttcaaccga aataaggttg gctgcgacct 129420
taacagtcag attctggata tctttggtag tcataccatc acgaagatga gatttgattt 129480
cttcgtataa ttcataggg tcgatttggg ttccttcaca gccccaagtc agaactttaa 129540 taatttttg tgcgtcaaaa tcttgggata caccactact tttttgtact tgcataattt 129600
cctcaatatg ttaggttcta caattattct atcatagaac ctgttaagca tggactgata 129660
tttatagaat gaaattcagt ccgaccataa taaccaaaaa cagagtacag attatttgaa 129720
ttttcatata gccatcttag ccttaatagt agggtgtgat tcgtaacctt taaggacgaa 129780
atctttaggt ctaagtttaa gaacatattc caattgttct ttagtagaaa gatggcgaa 129840 tttataaggc aatccaccta ttaccagttc acaaagctct ttaggttcac ggcgcaatac 129900
ttcctggcat tgttcaacat ggttggaata gatgtgcgta ttgccgcctg agaacactaa 129960
atcacctgga ataagattac acatcttagc tacgatatgc acaagagcgg cgtaagaggc 130020
gatattaaat ggtaatccta agaacacgtc aacagaacgt tggtaccact ggaggtcaag 130080
gtgaccatta cgaacgttga actgataaaa acagtggcat ggtggaagag ccatcttatt 130140
aatttctgct gggttccatg ctgatacgat ttgacgacgg tcattaggca ttttcttaat 130200
gcgttcgaca atctctacaa cctggtcgat accaccaaaa tctcgccatt gtttcccgta 130260
cacaggaccc agttcgccat cagaatatcc caaatcaatt gcttgatttt catagttttc 130320
```

-continued

```
gtcccaaata gttttacctt cagtacgcga gccatgagta cgttctctga ggtcattaac   130380
attagtcgaa cctgacaaga accaaaggag ctcagcaata caggctttcc atgctaattt   130440
tttagttgtt accgctggga agcctttagt taaatcaaaa cgtaatttag taccgaacag   130500
ggcaattgta ccagtgccag tacggtcgtc agtttcgtag ccattttcca ggatatcttt   130560
aattaaaaat tggtattgtt tcatttgtat actgtttccg tcagtgtagt aagttcgtct   130620
attttatacc aatgggtttc aagcatttca cgttgacgaa tttcatgaag gaagttttct   130680
tccaattgaa ccgtagagtt aacccgatgg catttctcaa tacgagaaac aactacttca   130740
tcagcataag gcaatgctgc atataacaga gcagggccgc cgattatgct tactttagag   130800
cttggtccaa gcataggttc aaagaacgta ttaggacttg atacttggat ttcaccacct   130860
gtaataaagg ttacgtactg cgcccatgtg atatagaaat gagcgaaatc accatcttta   130920
gtttcaggat aatcacggtc aaggtcacaa actacaatat gactacgtcc agggagtaat   130980
ccaggcaatg attggaatgt cttagcaccc ataatcatga ttgtgtcttc agtacgtgct   131040
ttaaaattct gaaggtcctt tttaacccgt ccccatggaa gtccatcacc tagtccaaat   131100
gcattttggt cgataccatc aactgttttg gttggagaat aagcgaacac taatttaatc   131160
ataatttcct cacgctttct tagcgatttt ccagtctgct ttaaattggt caacatcaga   131220
gtggtgaatc cagaaaccag atgagctacc atcttcataa agaggacaac catcacactc   131280
atctttccaa cccatcgcac acaaagcctg ttcagctttt tctagagctt ccggattatt   131340
accttggatt gtgaagtacc atttgccttt aacttcagaa tcgttgattg attcacgttg   131400
taatttcatt ttattctcct caagttgaca aggctatagt atcactacca tagcctgagg   131460
taaacttatt tttgaatcaa gcccatataa aattcagcat cttcggcatg cataccgtca   131520
caatactcgt cagccataaa gcgggtaagg tcttcaagag gaccttggac ttcaatttgc   131580
atactacaga attgcgtatc tttaatatag gtcataacta agaaggata acgattacgg   131640
ataacttcat aagtgtattc aaaatcaacg atatcgatat taaccttagc cattttattt   131700
tcctcactcg ttagttgata ggtctatagt atcatgttta aaggcattgt aaaccattaa   131760
atgccaaaaa agggaagacc gaagtcttcc cattataaat caataactta tagaccagct   131820
aacaggtcgt ccagaccatc gtcatcagaa ggacttactg acggctcagg agtagtggaa   131880
cgagttggtg tagacggttt ggaatcatat gcatcaaggt ctgcactgaa tgcgtccagg   131940
tcatcaccaa tcttgtcagc ggctgcagaa gctttagcgg cagcaccacc aagagcagct   132000
gtaccaacaa cttttcttaaa cttggcttcg ttagtttcga atgatttgaa atcaagcagt   132060
ttagaaaggt cgtgcatttc ttccatcaat ttagcttggt aagcttcatc attgatgtta   132120
ggaatttcag actgacccat gaatttggaa tcgtcgtagt tcttgaagtc gccaactttc   132180
ttagatttca gtacgaagtt cgcaccatca acggacatg ttacgtcaac cggcacttca   132240
ccaatatcag tatcaacttc aaccatctgg ttgattttat ccataatttt ctgaccgaaa   132300
cggaatttaa acactttacc ttcgttagca ggcactgcac tatccttaat aacaaggatg   132360
ttagcccaga aggaagtttt acgtttcatc agtttgtatt cggcattatt agtattaaag   132420
gtatcattct ggtcatgta tttacataca ggacatgaat cgaaatcgcc gtgagtagac   132480
gtacatgatt caatatacca ttgaccattt ttcttaaagc cgtggttaac aagtttaata   132540
aatggcgatg ggttagcttc gttttttcgaa ggaaggaatc taataaccgc tgtcccgaca   132600
ccattgtcat ctttcaattt ccactctgat ttatcatcgg aagagaaaga actaccacct   132660
ttaagggcat taagttgggc ggcaagctga gaagggtcac gacgtttgaa catagacata   132720
```

```
ttatttacct tatttgatat atttaattaa tttattaaca gttggtgtta tcacatgtac    132780
cttgataact aggttttgtt gatgaagtaa ttatatacta cttcatgtta agcattttaa    132840
tttaataaac tcagggtctt cgttaggaat ccatccttta ttaaattgtt taatcatact    132900
tttagctgtt gtttcactaa cagaaatacc agaacctata agacgacgcc aaccgcacgt    132960
tcttccttgt gaatttatta taatatattt attataagca atatcactaa gtttccaatc    133020
attaggattt gctctggaag ttttccaagg gcgataatca ggttgattca tgtaattaga    133080
agctttcata ttagctctaa cttcagggcg tttagccgga tgggtatgtc caaagactcc    133140
aaatcctccg ccggtgtaaa ctaaattaaa ataatcatcg ttatctctag cttgaacttt    133200
caattgttca gaacgttcaa tattgataac aatatcaaat ggcgttatag ccaaaatttc    133260
gactataggc ttttcttctt caatggctct tttaaatctg ggttgttcgc aagaagtcca    133320
atactcttta cctttacaat caaacattac accattttca aaagtacaat agttttttaga   133380 acctatatac aaaaatggtt taatgttatc actttgcctc ttaggccata tcattttata    133440
tactatattc aaaatttaca acccttaatt gtttcaatga acaatttacg agcttctaaa    133500
ttatcgatta taaggatttt cttataagca tttaatttag tcgaatactt agaccacact    133560
aaatcgttgg tctgttcatc atgtttattt attatatcca taaatgaatc aagcaaaata    133620
aacgtttcga atgaaataac attcgactga aggagcttaa aaatatagct cgagttaact    133680
tttttattat aatcaaaaat ttcagaaagc gcttgaactt ccactttctt actaaaataa    133740
taaatgtttt ttatatcatc ctcaaaaact tgttttattc ttttaagtct accgatatat    133800
tctcggtaaa agactaaggc gtcagcatca ctgatgtcgc caatccatgc gtcttggtta    133860
gccaccaagt tactcatgaa gataagagca agctctttca aagtgtattt atcactcaat    133920
ttctcaaaga aatatttgtc acgacgtttt tgataagccg tatcggagat tcgcatgacc    133980
cagttatatt ttataacgtc gtatttggcg ttgaagtgat gtttgagcat taagtatagt    134040
gaatatacgc tcttaccatt caccatacgg ttattgtttg gtggcatgcg aatcttaatc    134100
ataacaagaa atccagggta ttagtctttt gcgttcgggc cattgaaggt cgaagcaagt    134160
tatcatcaat ggcttcgttc ataatttat caataattcc tgcaggcaaa taacgagcaa    134220
agttaccttc agggatgctg ttctcttcca accatgcggt agccgcttcg aggtaactac    134280
aaccttcagc ttcaacaaag gcctcaatat caaggccgtt ctgttgtttg tttaccaata    134340
catggacagg ttcggaagcg gtattaaccg ctccatcaaa atcattcaaa gattgtgtca    134400
tacagttcta ccacttcagt ttttttcgtct tcgaaacgtt cacgagtgcc tttatggtac    134460
agggagaaca gttggttaaa catttttaccg tctacaccaa gttcagtctt agcacggtct    134520
ttgatatctt taatttcgtc accgtaagct tccattttta atttagtatc ggaagccgac    134580
ttaatcaact gagcaagggt attgccatgt tcttcttgat tgaattcaac tttcactttt    134640
tctttagcca ttatattcac cttaatagaa atcagctact gtagcggtta gtttagacaa    134700
accagattta acgaaataag gataaacttt agatttcgaa ggtttgttat acgtattata    134760
tctttcagta attaaagcaa caatatcatc tggaataaag tccatatcga ttaagatttg    134820
gttttcacag aaacgttcat attgttcttc agtaagaagt gttttaatta tatcatggtc    134880
ataataatta agagcaattg cttcaagttc cttggcacga gtgctaggag tacgttcgcc    134940
ttcaaccatt gtcaaccagt aatcaccacg aactttaata ctcgcgacgt tatctttacg    135000
gtcaccttta accactttag ttacacaatc cagtaatgag tcaccggttt ttgttttaac    135060
```

```
gaattttttc tgcattggag accattgctt aacgccaggg aatttatgga gttgagtaaa   135120
gtcaccgtcc gaagaaccaa tcattaccgg atggcctaaa gccgtaagga tacgagtcaa   135180
tacagcaata tggtcatctg cctcgacagt atcgatgttc ataacaatat aaggcatgtt   135240
atgttcgagc tcatcaataa tcaaatgcat tgctgtgaat aaaccttccc aatcaaataa   135300
tgattcttca cgagccttgg cacggttttt cttataataa gaagaataac gacgacgcca   135360
ataacctgat ttagagttat cgacacaaat gattaattgg ttgtaacctt gtttttaaa   135420 gtctttaata ttttttcttaa ttgaattcaa cacgaggtgt cgaagcattg ctgtagttac   135480
tttaggaaat ccggcatttt caccaaattc ttggaatgcc gcagccataa tgatttggct   135540
aaagtctaac aacaagaatc catctttttg acgttcttct tcaggaagta aaaaatctaa   135600
atcgttcata tgaacctctg tccaattagt gtagaggttc attatatcat gaccctagaa   135660
gaagtaaaca ctttgctata aatagttcta taccctgaaa acgaaaagga aataaaatgg   135720
ctgatatttt aaaacctgca ttccgtgcta catccggact cgatgctgcg ggcgagaaag   135780
ttatcaatgt tgccaaagcc gattacaatg tattagatga tggcgtcaac gttgaattct   135840
ttatagatga gaacaccatc caggcgtacg acgagacgcg cggatataag aaagggtttg   135900
cagtaatcca tgaccaacgt atctgggttg ctcaacgtga tatcgatgcc cctgcaggaa   135960
cttttactcc gggctattgg actgctaccc gtaccgaccc taaatggatt accgtagcgt   136020
ctcctacacg ccagctggct tccggtgaat atattgcagt agattctgct gctagcttta   136080
ctacatttac cctgcctcct aaccctacag atggcgatac cgttgtaatt aaagatattg   136140
gtggacgtgt tggttataac gaaatcaagg tccaatctag ttctgctcct ggtggtggta   136200
accagaaaat tgttcgtttt ggtaatcagt ttactgagac cttaattaca aagccttttt   136260
cttataacat gattatcttt gctaaccgtc tttggcattt ctgggaagca ggtaatgaag   136320
aacgcggtat tcgggtagaa ccgaacatgg cccagttcca atcacaagca ggtgataacg   136380
ttctccgtcg ttatacttca ggtgcagtaa ttaagtttac tcttcctaag tatgcgaacc   136440
aaggcgatat gattaaaacc gttgatattg atggtttagg aagtaagttc cacttaatcg   136500
ttgaaacgtt tgatgcttca tcttcattag gtaagcttgg tcagcatagc atggaattcc   136560
gtacctccgg tgatggattc tttgttata actctaccga aaaattatgg tatgtttggg   136620
acggtgaccg tcaaactcgt ttacgcgtaa ttcgtgacga tgttgagctc ttggctaatg   136680
aaagtgttat tgttttggt cctaataata cgacgccgca gacgattaat atcacattac   136740
ctacaggtgt agcccagggt gatgtcgtta agattgctct gaactatctc cgtaaagctc   136800
agacggtaaa tattaaggct gctgtaggag ataaaatagc ttcttcggtt caattgctcc   136860
agttccctaa acgttcagaa tatccgccgg atactgaatg ggtattgaat gatgtattga   136920
ccttcaatgg taacttaagt tatactccgg ttattgaact gagttatatt gaagacacca   136980
ctacaggtgg caaatattgg gttgttgctc agaacgttcc tactgtagaa cgtgtggatt   137040
ctaaggatga tttaactcgc gctcgcttgg gtgttattgc tctggcgtca cagacccaag   137100
caaacgtaga ccatgaaaat aatcctgaaa agaactggc tattactcca cagactttag   137160
ctaatcgtgt agctactgaa tcacgtcgtg gtattgctcg tattgctaca accgctcagg   137220
taaaccagaa tactggattt gcattccagg acgatttgat tatttctcct aagaaattaa   137280
acgaacgtac cgctaccgaa actcgtcgtg gtgtcgctga aattgctacg caacaggaaa   137340
ctgatgcagg tgttgatgat acaaccatta tcactcctaa gaagctacag acgcgccagg   137400
gaactgaaaa cctgtctggt atagtaaaat acgtatccac cacgggaacc actcctgcga   137460
```

```
cttctagagc aactgtaggt actaacgttt ataataagaa cacaactact ttagttattt   137520
ctcctaaagc tttggaccaa tataaagcta actatgagaa ccaaggcgct gtatatcttg   137580
ctacgcaagc cgaagttaat gcgggtgcta ctaacccagg ttttagtaac tcagttgtta   137640
cacctgaaac attaggtgct cgtcgtgcta ctgatactaa tcacggttta attgaaattg   137700
ctacgcaaca ggaaactgat gctggaactg attatactcg tgcggtaacg cctaagacgt   137760
taaatgatag gaatgctact caaacactta ctggtattgc tcgtattggt actcaagtag   137820
aatttgatgc aggtgtatta gataatgtta tttcaactcc gttgaaagtt aaaacaagat   137880
ttaatgatac tgctagaact tctgtctcag cagccagtgg tttgattgaa tcaggaacct   137940
tatggaacca ttatacacta gatatccgtg aagcaagtaa tactcaacgt ggtacggctc   138000
gtttggctac ccaaactgaa gttaatactg gtattgatga caaaacaatc atcactccac   138060
ttaagcttca agctaaaaag gctaccgaaa acgctgaagg tattatccaa ctcgctactc   138120
aggctgaagt tattgctggt acggtaagta ataaagcgtt tagtcctaag cattacaaat   138180
atatcgtcca acaggaaaaa tcctgggaag ctacttctgc tcgtagagga tatgttaaat   138240
taaccacagg tacagccact tgggaaggtg acgatactaa tggttctgtt gccaacctgg   138300
ctaaatttga agattccggc tttgctattt ctcctcttca aatgaatacg gcattaactc   138360
actatcttcc gattaatggt aaggcttttg attccgataa attagatgga tttgatagca   138420
cgcagtttat tcgtcgtgat atagcacaag atattaatgc taatatgaca tttaaacagc   138480
ctgtaagaat tgaaaacact ttagcggtta ccggtgcggt taatttgagt ggttctgtta   138540
cttcaaataa tactacgtta accggtgcta ctgcaatcaa tagcaattct actgtaggcg   138600 cttttgaatta cattgagttc acttcacttt cgcaaggctc gggtacttgg atctctcaac   138660
atgatagcaa tgttaaagct cctgtatttt taaatataac tactccagcc ggcgcatcta   138720
gatacgttcc tttaattaag caacgttata aagatggaac atttaccttt ggtacattga   138780
taaatgaacc tacctcaaat gatgaaggtg ctttttattct tcattatata gatgcagtaa   138840
aaacccagag caaatggacc tttagacgga atggtgattt agaaataact gcaggtaatt   138900
tcgttcttgg taatgggact gctgtaatta atggtggtct taatgttact aaagcatctg   138960
gtattactac tacaggattg gttgcttccg ctgcatcaag atttgatggt agtgttgcaa   139020
ttaataatac attaactgtt cgagaccctt tgacagctaa tggtggttta acagttaact   139080
cgagaattcg ttcacagggt actaaacctg ccgacctttta ttcgagaaaa cctaatgcag   139140
ataataccgg tttctggtcc gttgacgtta atgattcagc cacatataac cagttcccag   139200
gttattttaa aatggttgaa aaaactaacg aagtaacagg actgccgtat ttggttcgtg   139260
gtgaagaagt taaatcgcct ggtacgttaa ctcagttcgg taacactctg aattcacttt   139320
accaagattg gattacctat ccaaatactg cagacggaag cactactcgt tggactcgta   139380
cttggcagca aaataaaaat gcttggtctg gatttgttca ggtatttgat ggcggtaacc   139440
caccacaacc atctgatata ggtgctttgc cttctgacaa cgcttcaatg agtaacttga   139500
ccattcgtga ttggttaaga attggtaacg tacgtattgt tccggacccg gtaactcgtt   139560
ctgttaaatt cgaatggatt gatacaccat aagaggtaat atgaaagat ttatggctga   139620 atttggacaa gattacgttc aaattcctgt actatctgaa aataatgccg ttagttataa   139680
acttagtata gcaggaagct gtactaagtc cactaaaaag gcttatatca aatttcaaga   139740
tgaggacttc ggtcctcaga atttccaatc tggcctaaat ttggttgaaa tagacccgac   139800
```

```
aaataacaca atagtgacta caaaatcata cgcatttacc aaagaccatg atgttatttc   139860
ccaagcgttt ataacttata tttcgtctat acctgctggt agaattgttt gctttatttc   139920
ttccggtaaa ttaaacgcct cacaggtatt aattgattgg tttagggctt ctggctctac   139980
agcatttcca gataaatggc tcattgataa agtggatact tcttattcag cttttttatgt  140040 ttcaggaaga aatgctattg taatggaaca tgtgctttat aacgacggcg ttttggtaga   140100
agacgtttcc accccattag aagtcgttta tgacaacttt aatgatgtag gaggaaccgg   140160
gttccctgtt agagtcattg aagatgaaac cacttattat agtggagcta ctcaagaaat   140220
taaaaggttt cctgccgaat ccaccataac tccttgtgct ggttataata tggttcctgg   140280
agatttcttt tatctcaaat tccaaatgac ctacgaccag gctttaaaag atttagggac   140340
aacccagatg tccatacgat tttttaatgg ccaggaaatg attcaatcca ctgatatcaa   140400
tattcctgta ggagcgggct ctccaccagc aggcgcatgg atgtcttttg agcgcgtaat   140460
agaagttccg ccgaatgcta atggttttac attatattgt agaaaaactg tctcaggcgg   140520
agtaggaggt gttaggaatg ttatgtttgg tgaaatagct agacctgaag atactcctaa   140580
atccgctgaa attggtgtta atggtattcg tatgagctat ggcaccgaaa cccgttcaat   140640
gggtaatgtt attgcacaat tgaatgacaa atcatccggt aacgcaggta aggtgtttgt   140700
tcaagagttt aaagaaaaat attaagggac cgtaaggtcc ctttttgcta taaatacgtt   140760
atctaataaa gaggaataac tatggctgat ttaaaattag gctcaaccgc tggaggttcc   140820
gttatatggc accaaggtaa ctttccgctg acgccagtat caaatgatat tttatataag   140880
acctacaaaa tctatactga atttaataag cctcaagctg cagataatga ctttgtttct   140940
aaagctaatg gtgggaatta tttaggtaca gtaaactttg ataaagacct acaatttaaa   141000
gattctgatg gatactgggt taaattaggt agaaaaacca atacaacccc aatgtcatcc   141060
acatattctt tctcattcag aatgagtaaa ggcatgggtc ttgaaacagc tgatggggtc   141120
ccgtttgtaa ttttcgaccc gactactgtt gtaggtgcaa accgacttac tgtaatgggt   141180
gatatccttg gtcgacagat taaagatgaa tctggaagag tgttttctcc agggaatacc   141240
ccgacaaaag cccaagtcgg attaagtgat gtggataacg caaaacaggt ccaaataaat   141300
aatagtaaca tacaatctat ggctggcgtt ctttcagccc cgaatttcat atctaggaac   141360
ccaggtacat tgaacgaaca cgttcctcgt attgaccagg ttgttcttag aggtacatct   141420
gaagattttg gatattatta agaggcatta tggctacttt aaaatcgata caatttaaaa   141480
gaagtaaaac accaggagcc aagcctactg cagctcagtt agatgaaggc gaactggcta   141540
ttaacttgcg tgaccgcact atttttacta aatcagacca gggacagatt atcgatttgg   141600
gctttgcaaa aggcggacaa gttgatggcg atgttaatat taacgggacc ctgaatttaa   141660
atggtcctga aattgttgcc tccggtggtt atatagaatt taactatcgt acgacaggta   141720
gtggctcttg ggcgggtcag cacaatgcca aagctcctat ttttgctgat ttaagtgcgg   141780
ctgcatctac ttcagaatac aacccactga ttaaacaacg ctttaaagat ggaacatttt   141840
cagcaggtac actagtaagc gaaggcagtt ttaaattcca ttatattaat gaagccggtg   141900
attcgaaata ttgaccctt aatcgtaatg gtaattttca agttgatact ggcggcttga   141960
cagttacagg cggtagtatt tccacttcag gaaacgtagc tgcttccggc tttttatcag   142020
caccacaggt taatagtaaa aatattattc ttgattcgaa aaatttcgga cagtatgacg   142080
tccaatcttt agttaactac gtataccag gcacaggcga aacgaatggt gtaaactatc   142140
ttcgtaaagt tcgcgccaaa tccggcggca ctatgtggca tgagctttgt actgctcaat   142200
```

```
taggccaagc agatgaattg tcttggtgga caggtaatac tccatcatct aaacaatttg  142260
gcattcgtaa tgacggacga atggctggcc gtaatagcct tgcattaggt acattcacta  142320
cagatttccc gtctagtgat tatggtaacg tcggtgtaat gggcgataag tatcttgttc  142380
tcggtgacac tgtaactggt ctgaaatata ttaaacaata tgtttatgat ttagttggtg  142440
gaggttattc agttgcttct attactccag atagtttccg tagtactcgt aaaggtttat  142500
ttggtcgttc agaagaccaa ggcgctactt ggattatgcc aggtacgaat gccgcatttt  142560
tatcagccca aactcaggct gacgggaata cagctggcga tggtcagacg catattggtt  142620
ataactccgg tggaaaaatg tcgcactatt ccgcggtaa aggtcaaaca atattaaca  142680 cccaagaagg catggagctt aacccaggta ttcttaaact ggtaaccggt gcaaataatg  142740
tgcagtttta tgctgatgga actatttctt ctattcaacc tattaaattg gataatgaga  142800
tatttttaac tacctctaat aatactgcag gccttaaatt tggcgcccct agcggagtta  142860
atgaaacaag agctatccag tggaacggtg gtactcgtga aggacagaat aaaaactatg  142920
tgattgttaa agcatggggt aactcattta atgccgccgg tgataaatct cgcgaaacgg  142980
ttttccaagt atcagatggt caaggatatt attttttatgc ccatcgtaaa gctccaaccg  143040
gcgacgaaac tattggacgt attgaagctc agtttgctgg agctcttaat gctaaaagta  143100
ttaatgccat cgaaaatttt aaagttaatg gattaagcac tttagtcggc ggagttacaa  143160
tgagcaatgg acttaattta actggcggtg ctaatatcag cgggccagtt aaaatcggcg  143220
gcgtcaccaa tgcattaaga atttgggact ctcgctatgg cgccatttc cgtcgctcag  143280 aaacatcatt acatattatc ccaactaatg aaaatgaagg ggaaaacggt gcaataagca  143340
accttcgtcc gtttagtatt gagttaggca ccggtacggt tataatgggg gataaatcta  143400
cgggcggacc gcttttcacg gtcgacaacg taagtaaatt cgtccagacg gactgtagat  143460
tccgtgttaa catggattct gatggtattg ttgttaacgc ctcatctcaa gcagcatcta  143520
actttattca aggtcgtaag gctgatgtga ctaaatggta tttgggtatt ggcgatggcg  143580
gcaacgtcgt tcgtatgcac aactacacat attctcacgg tattgcgtta aactctgata  143640
ctgtcgatat tactaagcct cttaaagttg gaaatgccca actaggaact gacggtaata  143700
ttacaggtgg tagtggtaat ttcggtaatt taaatactac catcgagaat atgaaagccg  143760
atattgttac cagttacccca gtcggtgccc ctattccatg gccaagtgat tcagttcctg  143820
atggatttgc tttgatggaa ggtcagacct ttgataccgc agcttatcct aagctcgcta  143880
tagcatatcc taccggtact attccggata tgcgtggaca aactatcaag ggtaaaccta  143940
gtggacgggc cgtgttaagc gcagaagcag atggtgttaa gtctcataac cactccgcat  144000
cggcatcaac tactgctttg acaggcacaa ccaatggtac ggacttgggt acaaaaactg  144060
tcagcactgt tgatataggg cgtaagtata ctaataacgc aggagcgcat actcacacgt  144120
tctcaggaac aactagtacg aacggcgacc ataaccaccc agcttcactt ggtaacaacg  144180
ccaacgttca atcaggtcgt tttgcagcat ctaactcagg tcagtctgct atagcatata  144240
ccaacaacgc tggtaaccac agtcacacgt tctcaggaac tacgtctgca ggcccagagc  144300
acagtcacta cgttgatata ggtactcata accataccgt agcaatgggt tcgcataccc  144360
atacgttctc tattgcggct catggtcata ccatcactgt aaataacact ggtaatacag  144420
aaaacacagt taaaaacatt gcttttaact atattgttcg tttagcttaa ggagagggac  144480
ctcggtccct tttaaatatg aaaatttatc acttttattt tgatactaaa gaattttaca  144540
```

```
aagaagaaga ttataaacct attaagggtt taggtctccc ggcccattcc acagctaaaa   144600
aacctttaga acctaaagaa ggatacgcgg tagtttttga cgaaagaatt caagattgga   144660
tttacgaaga agaccaccgc ggtaaagatg tttggactta aataaagaa catcttatta    144720 taaattctat tggaagttta tatggggtca catttgacga gcccggcgaa tttgatatat   144780
ggactgatga cggttggaaa gaagacgagg cttataaacg agtaaccatc cgaaataaga   144840
aaatagcctt gctacataaa gaattccagg tattaagtaa tatggttgaa gcttcagtcg   144900
cagataaaaa ggaaaaattc tatcatcaaa accttaaacg gttctttgct cttttagaaa   144960
agcatgagca tttaggtggt gaattccctg cgtggcctga aaagaacgg aagccttggt    145020 ataagagatt tttcaaataa tacttctgta ttataaatat ctttaaagga gaaaagtatg   145080
gaaccaaaag taggaatatc attatcagac ctactttttg gacttcttga tagaattttt   145140
aaagatactt cttccgggaa agtagttttt tcccgggtcc tagtcgtgat attattgttc   145200
tttatggccc tggtttggta taaggcgaa tatattctaa acttttacaa agagacaact    145260
tatgcctctt atactgaaat gattagacaa gaccaggaca atagatttaa aattgcggct   145320
atcgagcagc tccgaatagt gcattcttct tcaggtgcag acttcacagc aatatattct   145380
tttaggccga ccaacatgaa ttattttgtg gatatgtag cttatgaggg taaattaccg    145440
gaaacggtag acgcaaaaaa cacgggaggg tttccaattg acaaaacgtc agtagaatat   145500
atggcgggag ttaacgggaa ctattttgaa tcaagtaccg aaactgtatt ccttcctaca   145560
aagaagaaaa cacaattcac gtatatgttt tcatgcccgt tttttaattt ggataacgtc   145620
tacgccggct cgatatcgtt gtactggtat gatatcaaac cggatttagg atttcctaga   145680
ctttcgtcta tgtgtggtca agccggaagg acattaggtc gaactcgtta gaaattggag   145740
gtatacatca ttaagtaacg gtgtatatct tcatatcctt cattaaattg ctcaataaga   145800
gtgtcacgct catcttcagt taatgactta acaatttgt tataagacaa accattaagt    145860
tcctttccat gttcattacg aatacctaac tcattcaaaa aggcaataaa ctcatcacga   145920
cgttgcatga tgtcttcaca atccgttta atcaaaatgg aaacaatagt ggcaatttcg    145980
gaaacgattt caattttagt cataatattc tcttcaattc agtacgacat tatctgatag   146040
ggctatacta acatatcctt agggattgta aacatgttct tcgttctttt taacatattc   146100
ctgatacatc tcttctattg gttcctggaa cttaaaatca gctcccagga attcctcaaa   146160
ggacgcctgt tcacgtgtac gcatacctgt tacggtattc tctaagttat gactcatagc   146220
ctttacccct atgtttctgc ttacgcttgg actctttaaa attttcttc ttgtcttat     146280 gaacagaagc cttattgaaa tcgtgcttag ctaccagatt gttcacgtaa tttccttaat   146340
tgatattcaa gagagccgat aatttcttta ttagttgcaa tatacatatc acgtaggaat   146400
ggcttcaacc cttccatatt cccatggatt gtcttggaac taatattctt tatatattca   146460
tggtctaaag catcccaagc cggttggttg acataagttc cccaattatc ttccaccgtg   146520
acattcagtc gtttaacatg attaatatgg gcttcgattg catcaatctg gagttgttta   146580
agattcatta gtaaaggtcc tcagagtaaa gttcttttc actaccacca cgttcaatac    146640
gtacttgatt agcataagta gcaataatca ttgcttcttc gcgagtccaa taattgctgt   146700
attggtcgat aaatccttgg tcatcgccac aaacatggtc tgacacaagt ttatcactta   146760
cttggtcaag cacttctgcc atatctttgg aataatgacg agctcctgga ataactagag   146820
tcccaccgtc cttcagttta aaacggttgg ctgcgcatac aatcctgcgc tgatattttt   146880
cattgttgtt ccaatgtgca atctgccaac agatttcagg gacttcattc aaaacatctt   146940
```

```
gttctgtata ttcgtatcca tatgactgta atttggcagc cagactttca ggggtctcac  147000
gtgacagagc tttatctaac agagctaaac gttcttcaaa agtttcatt tgaaccatcc  147060
tttaacacgt tgccagaggc ttttctgttg agctttattg acaccgatcg agcgaataac  147120
aggttgtgat tcttggtatt ctttatagtc agctttataa acttcgtatg cggcatcaac  147180
aaaggaagaa atagcagcca tataatttt acgaatacca actgaggcat tatcatttc  147240
gcgaataatc agatattggc ctgctttaac cttaacgata gaaccgagat aagcgccatg  147300
gtaccagatg tcccaacctt cttgagtagg ttctgcacaa cgacgaagtt cattaacaat  147360
attcagcttg ttcataataa tttcctcagt cagttaaatt gcgttggtta cggctttgat  147420
aacttcagat gatacgtttt ggaagtcgat ataagtattc ttaccaccag tcttaatctt  147480
aacatcaaga ttcaaggaag taaacacttg tttttcttta tcagtcatat tataaccgaa  147540
gatgcgcatc attccatcac ggcgaacttc gatttggcga ataccattgg tacgtttggc  147600
gaatctaact tcaaggttgc tacggttttc agctatttca cggatttcaa tacggtcttc  147660
taataaagct ttaacttcat cagcaaatac caccatttca ggagtaacgc cacgtgaact  147720
acgtgtttta cgttttttcca gcatctctgg ggcattttca gaagcgaaca aatcagcagc  147780
ttttgaact aggtccattg cttcacctgt agccactaaa ccatcgccag attttcgat  147840
gaatcctttc ttaatcaaca caccgatgtt agagttaact accgcagcac taaattgctc  147900
actcagggct tcacggactt cgcctgaagt gatgaagtta tgcttgatga tatgtactaa  147960
gatcgaagca gtttttcat tcaggacgtc ttcagaagct ttgatgatat aagtaatttt  148020
agacatttta atctccgata accatttatt tgataggtct atagtatcat gtttaaagca  148080
gaagtaaaca ctttttttcac taaacccaaa aaaggaaccc gaaggttcct tactttttaa  148140
agtgggctgc tattaaacct atagctaagc ctgttgccag gcctagaata acagcaaaga  148200
tacagagtaa caagaactcg actccaaggc tcatagagcc tccaaatctt taacatactc  148260
agttaccaca tcagtggttt tccagtattg gtgctcttct ttcttagctt tagcttcgag  148320
ggccagtttc ttggcttcat cggaagtgat atggaaaatg ttcatggcca ctagtttatc  148380
agcatattcg ccgtagactt tattaccagc caattcttcg gttaaaacct tacgagtctt  148440
accttggata accactacgc cgtcaataac atctttgatg aatgtggctt tagccaatgc  148500
cagtttaaaa gcttcttcgg tttcgatgat ttaccatca atacgtttct gtacaaaggt  148560
cttacggacc tcaacgaaat cacgaatcag ttcaactgca tcttcgtaaa ccttaagttt  148620
accttttca ttaatgacgg tcaggttttg tgaacgacgt tcgattaacc caaagtcctt  148680
catgatttt tcatgcttct tattttcttc ggagggcaat tcgtattctt tacgaatctt  148740
aaccttgaag ccaaaaccat tctcgtcaca gtcatcatca tatgtgatat acctttgtc  148800
ttccagaggg tctaatatct tggccacata tgtttcacgg tcatatttgt acgggatttc  148860
cgtgatatgc atttgggttc gagatgtgaa cttataggtt ccgcgaatct cataactacc  148920
tggttcaatc tcaaccactt caccacggaa ttctggataa gccactttag gcttggttac  148980
tcgttttttcc tgaagaactt gtagtacagc tttcttaaca gaatcaaaac tatgaggaag  149040
aatattagtt gcataaccag ttgcaatacc ggaaatacca ttaagaagaa cagtaggaat  149100
aataggcaga taaaaagccg gtggcttatg ttcgacatcc gcatgaaccg gagcatattc  149160
tgtgtcctta taaactttg caaagttact tccaatacgt gcaaagatat aacgagaggc  149220
cgcagctttt tgaaccaatc gggaaccaaa gttaccttga ccgtccaaca aaggataatt  149280
```

```
gttattccat gtgttagcca ttagtgctaa agcttcttgg gccgaattct caccatgatg   149340
ataacccaag tcggcaacac caccggcaat agaagctagt ttatggaatt tgtctttatt   149400
tcctttaccc atttccaaag ctctacaaac accgaaacgt tggactggtt taaagccgtc   149460
aatcatatta ggaatggctc ggttttcaac cgtatacatt gcataggcca gggcttcgtt   149520
gtcaataatg cttttttaaat cacgagttgt taattccata gcaatcctct ttaaattgat   149580
ttatcaatct agtataacta atattatcat atcccatagg aataataact ttttttaaagg   149640 ctttatcacc cggtttattt aatttaatcc ataaattgta aagcgtatta taattttccc   149700
aatgtttacc ttttctaaat gctttcttta atgcttttaga atgtcgttct ttaactttag   149760
ggtccttaaa agcctttttta acagaatcgg ataactttttt aactgattcc gggttttgcc   149820
acgtgtcttt tgctcttaaa gaagcttcta atctttcttc ttcgccccac cattcttttta   149880 cagatttcga taatttatct cttttttctt gagagctcca aacagattta gaattcaacg   149940
atatttttag tctaacttca ggtgaattca tggcctctaa atggttcttt acatattccg   150000
ggttcttaaa aagagcttta gtagcatcag acttttttctt tctggtttta tctgtattgg   150060
cttgtctttt tattccttttg gagtgcgatt cttttattttat tgggtctgcc caataaaattc   150120 tcattttttc agatagaatt ttagaagcct tttcttttagc tatagaatat cctatagaat   150180
tcaaccttat tccttttagga ctgcctgaag tataaaatga ccaatatgct aaataaagac   150240
cattagaatt gggataaatc tttgttagta tccaatgggc tatataatgc tctctagcgc   150300
ttaaaagaac tttatttttca ggagtatcgg ggcctcctat gcattccggg attatatgat   150360
gaacttccga ataaaaatcc aatttgcctt ttttgagccc tcttccttta ccctatcaa   150420 ttattgcttt gtacaaatta tgataattca tttataattt taccatacta gtgaatgaat   150480
agccataata acatcggaaa taaaaagcac aacttggata agtccgaaca ttactccata   150540
atacagtgct actaataaag cagcaagggc tactgagtag cccaagattt gtttaatcat   150600
ttttaatcat cttaagtaaa ccgacagaag tagaaagaat ccagccaata aacagaaaac   150660
ttaagaatac cggaccaggg gtccacacac ctaaaaagaa gcaaaccgaa cagacaatag   150720
ccataataag ctcaataaaa actagaataa ccatattttc ctcattagcg tccgaagacg   150780
cctttagttt taagattgtt acgatagaac tgcatcacat gttcgttatg gaaattgctc   150840
attagtatgc ctgcagaatg aatttaaagt tatcagccaa catgcggttc atttcttcca   150900
gtgtctggag gtcggaacta tgattgcgag tgaaagccgt tgcaatttga cccttaccaa   150960
aacctgtagt cagaggtttc attttagaag ccggtacata aagaacttca tacacaaacac   151020 cattcactgc catagtgcgg gctgattgag aacgtttctt acgaatgtta gccacgatac   151080
cgtcgagacc ttgagccgaa cgttgattac cgacataaaa acgagccgct acgacacgag   151140
aatcagctcc gcctttaaca aagaagtaga agcctggctg agcagagatt tctttagaag   151200
gtttaccatt ttgatattca ccgttcttaa cataagcaac ggtagtagca ccagcagaca   151260
gaacgttacg gcgagtcata taagtattca tatcaatttc ctcagtagat taatgttttg   151320
ttatccagtc aacgagaacc attataacat gattctcgag gttgtaaact attttttgtag   151380 ctgttctaaa ataaatccgc tggtatataaa ggtagcatta taaaccttgt tcagcgggct   151440
caaagcctgt ccgtaagtat cacgtagttc tttgataaca ttttcataac tcacataata   151500
gccgctatga taatacgggt ccatactcat acggaattta atgaaccgat aaaagcctgt   151560
ttccgggtct tgaacgaaaa cgaaatcagc actcgtcata atttttgaat ctacgccggg   151620
aatcatactt tgattgaatg ccaccgatgc atcctgaagg ctgagttgtt taagaacat   151680
```

```
taccttagca ttaccaaaaa agattttaga catgataatt tccttattca acgtcaacag   151740
aaatagccat cagttcatca acagtaagac actgtacact ggggcctaca caaaaacgct   151800
tagtcgaatc ataaaggtct gtagcattaa caggttgtaa ttcggtccca acttgcaaag   151860
gagaaatgcg aatcagttgt tggccgttat gcaatacaaa gctctcacca actgcaacat   151920
ctttaaaaag tttcataata ttttccttag aagttaaaga atacacgtac atggtcaatc   151980
ataaaaacga ttgggaaaat gctcaacacc attaacaaca caaacatgtt ccaaattgct   152040
ttaagtaagt ttttcataat catctccatt agttgatagg tctataatat catgattaat   152100
ggagatgtat actgatttat gccaatttcc acaacaataa actaaaacat acgcaaatca   152160
ctgggataca ggccatccaa ataaggcacc acattttgct actcaaaaca ccacctcttt   152220
tatctcaatc aatcccctgt acaatgcagt gcggaggtca taagaatat ctatgccgtc    152280 gacattatct agtttaccgt cgataagttt ttgtaaatct tcctttgatg cgattaaggg   152340
acggagaaat ttacattcag aaagagataa ctctgtagta acatcatcac cttcacctga   152400
cgcgtcatac atagcggcaa caaccatacc tgtaactttg tgtttagcgt aatataattt   152460
gatatccatt ttgttctcct ctcaagttga taggaagata gtaacaccat ccgtggtgta   152520
tgtaaacact tattttaaaa aattataagg cgagatacca gccgttgtaa ttgctcttac   152580
ggactagctt tttgatggct tctctgtcac cagagaactt aggagtgaac aggacgtcgc   152640
ctgcctcatt tactgaagtg tcgaatataa ttatacagtc tgcaacttta tgattcaaga   152700
gcggccccag gttaatccct gttccatacg ggaagtcacc cgagtatcct gtagtacagg   152760
aaatccactt agaatctgat tgatgggtct tgacctctac acgtagtcca caatacatag   152820
gatgggctaa aacgtcccat gcataggtat aagggtcatc atggtcttcc aaaccactat   152880
taacataccc tttcaaccaa tcagcaacca tgtactcggc gtacgttgca atgacacacc   152940
gagtcaatac ttctttctta tcttgggacg ggtcttgact taaggaatac aatacgtat    153000 ccttaatctt aaccttcatt tcgcctgtta aatcagatgt cttcagggta aatgtcggca   153060
tcgctgccaa tcggagtagc cccggggttcg tcttcaccat aaatgcctcg aatatgaagt   153120
tcgccgtaat aaattcggtc gtcgggttct aaagtatcag aatcaattaa aggaaattca   153180
ccttcgacca cctcatcgca ttctaaaaaa gcgtaatgaa catcaccagg gtgtttaaca   153240
agcttagcac aataaacagt acctgcttta tggaacccac gcaaattaga atcttgata    153300 tcacgttcac cgacattcag ataattaatc attttactca ccgaaataag aaatacgaac   153360
ctctaaacaa tgagcatatg cacccatcgc atccagttgg gcaatcagta accccttgttg  153420 acggatatca agagtttcaa aaacaccgcc tttaataaag gtttctagtg cattaatttt   153480
aagaactaac tggtcgtatt cttcaattaa acgtgcttgg taacctaaca taatttcctc   153540
ttaggaggcc gaagcctccg tttagtttta acgtaaatct gatttaaact gttcggtaac   153600
gtcttccaga acttcataat aacatacgcg cattttagca tcgccataat caacaggaat   153660
actaacaaca tcacgtgggt taactttaca tgaaactaca cggttgtttg aattaccaaa   153720
tgcaccgata tagctacgag agcaaacgtg tagaccgctt gaacaagtta ctgtgtcgtc   153780
attgtttaca cgtgaacgag gcattttaac cggtttgcct ggtgagttat caaacgtacc   153840
agtacggcag tcggtgtaat cggagttaac caccttccac gtaataaagt ggccatcttc   153900
agtaattttg atatcgtttg caaccaggaa gtcgaacaaa cgttgtacag cttttttcgct  153960 tgggttttct aacaggttct caaggaacgg caggtagaat tcgaagtctt cgccatttc    154020
```

```
cattgaagca ataatacggc caatcaaccc tgaacgcaat tcaacgcctt ggtaaaccag   154080
acgtccacct tcaatacgaa cgttacccttt gacgaagacc ttaacagctt ctttaatgga   154140
aatcagttta atcgcgtcgt caaaacggga ttctttaaga gcctgtacga tggcatcaaa   154200
atgtttattc ttattagtgg tgttccatac tgtacggcct tcggtgatgg acacgaattt   154260
agaactggca ttccaaataa tttcagggcg agaaccaccg atagtaatat caaccggaac   154320
tacacgaggc tcgttaggaa ccgttacttt gatatttccg gtaataacca cttctgttgg   154380
ggcattaaga ggtacagtag gcgcttttt aagcgattcg gctaattctt tagccacttg   154440
agaacgttta gcttcttcag cattttcag gactttacga atggtatcaa ccgaaacact   154500
gtaccaatcg gctagttctt gctgagtata attaccggat ttatagaggg aaactacttt   154560
ctcttgttca gatttagcca gacacttaat attgtacata atatttcctt agattaagcc   154620
gcttccacgg ctttcatgaa tttaacgatt tgagctacag aagcctcggt aatggatgtt   154680
ccacgacgat acatgtagtc cgaaactaaa tggtaatcag attcaaactg taaagtcatt   154740
ttatcattgt tgcttgaagc attattggtt aacgtattaa acgtggtgtt acaaattttc   154800
ttgataacag aaagcttgtc atcagtgata taaccatgga aattcatata acggaatata   154860
tcatagaaat tactcagacg agtatatgct tcagtcaccg gcttatcact aaaatacttg   154920
gtcatgaaac cgagctcagg gaacttggca atgatttcaa ggtaataccg agcacgggta   154980
ttactaccaa ggtagtcatc aacatctacc gcgtctaggg cttcagcata ggcttctaat   155040
gtagcttcca tcaggcattc acactggcct aacttttaa tcttttttggc aatctgaggg   155100 cgaatgatat ggaattctgt tacaccaatc aaattagcca tacgacacat ggtagtggta   155160
ttgatgtcaa agataccata agcttcgtcc attcccatga tatcagaacg actgccaaac   155220
agaacataac ctgtaatttc ttctgcttct gcggcggtca aatacatggt ctctgtttgc   155280
caacgtccat ctttaatgaa ccaacgataa gcactcggtg ttttaggacg aggttctgat   155340
gagcgaacag taactggaat ccatggctta acaattttat tcagttcaga gactttataa   155400
aaatgaattg tgtcaccttt aaaaagttct ttaaccttt caagctgctg catttgcagc   155460
aaagaattag ggtcgacaaa aataaggtct gttccgtatt taggaatatt gtgctcttta   155520 acaatttct tggctgaagc actgttgtcc attgccagag cccaaagtcc tcgaactaat   155580
ggaacacggc ccttttcatc atcataaaca acatggattt cttttcttatt aatgcctaat   155640 aaattactaa gtcctgctac tgaagaagta ttaccgcttg acttaattcg tttcaaacgt   155700
gggtctgaaa cgacttcgta aaccacacct aaattaataa ggtcgttttg aagggtataa   155760
cgctggtata atttctcata tgtcaatttt tctgtagtaa acaggctagt tccaccttt   155820 ttagtaagat agtcacgagc gctgtagcca aggttagaaa ggtcacgata acatggcgt   155880 ggattatcag attcaaccca ttcctgtgta tcgttttaa agactaccgc atccagtgct   155940
tcgatacggg ttgcaatatt ttccatcgta cgtttatcaa gagacaacac ttcacgagac   156000
ggagcaatat ccagtgaacc catagggaac ttaatataaa ccacatcatg gcgagtacgc   156060
atccatgtgc ctttaatata ggcggaatcc aatggataaa caataccacc gtaaacagca   156120
taaagtcctg aacgttcgaa gctgccataa tttgtagtgg ttacaggatg gtaatcgtca   156180
aattcaggga aataatcaac ttcaacacca tcgacatcac caagaccaac aaatggacgc   156240
atgatataac gaatttcggt ttcaaactta cggaaatctg attcatctac aggaactgtg   156300
atttcaatgc ctgtttttatc acctggctgc ataggttcga cgaaagtggg tttaatctgt   156360
gggccatcac cgtccatata agctacataa ccacgaactt caccattatg ccatgacgtg   156420
```

```
atattaaacg tttccgtata actaaatgga gattttgaac caagtccaaa gccgccgatg  156480
aaatcattag aagaggtttt agaagaagca aataagaat  tatacagacc tggttcttca  156540
tcattaccac gaatctggaa atcactcatg cctggaccaa atcacggca  tacgaaacgt  156600
gggtccagtt taccaggaac ctgtactttc cagcgttctg tattaccatt cagcatatgg  156660
gcatcaatca tgttagtaat cagttcacgt actacagcac gtactttatt actataaagg  156720
tctgatgaca gaattttaaa gaccttaggc gaggcctgga tagtaaagcc tgtggactta  156780
gcgccattac caatgatttg ttcttttcg  gtttcaataa tcatatttt  ctcaattcag  156840
gttacgttta aaaatgtctg ccacttcaag gagctcgtcc ttagtagcga tgtcgttgag  156900
tattttatat ctgatttctt taaagcgttc tttaaaatcc tcagctgcat tgatatcaaa  156960
aaatcgctgg attagccgga attctttatg gacggcttta tcgaacaaat caatattcac  157020
tttaaagttt gtcatttta  actacctcat gttgaacata ttctctggta gaacctagtt  157080
cagccagaat tcttctcata gaacccattg tacttttgtg ctctctgtgg cgatacatta  157140
tctctaaaac cttttcctgg acaacaggag agagcgcctg ttatcttta  atctttaagg  157200
caatagattt tacagccttt aagtattcga gtcccttacc gcttgtagtc actactcctt  157260
catctttaca gttacgaata gccgtttcca taaggataa  agccaggttg tcagtattca  157320
ctatactgtt atcttgcata atcatattct cacctctaga taatcctatc acagttttgt  157380
tatgttgtaa accccgaaaa gggcccgaag gcccttaatt attcaatttt gtagacttgt  157440
cctcgaactt gataaaattc gccttccag  gtttctacca taatggtcac gtactctgcg  157500
aacaaaggtc tcttctcagc ccagagatat ccaaattcac cggtggctag cgttatccag  157560
tactttctca taaagtctcc taattgtatg gcactcatgt accatacata tttattacga  157620
catccaggcc ttacggagtt gagggtcgtt tcctaggagc atttcgaact gttcttcca   157680
atcttcaggc aattgaacta catcaaattt agggtcttga atcattcgac ggtattcaac  157740
tttctcaaga gaaccgagac ctttgatata acgaatggag tgttttggta gagagtcctt  157800
agctttggta taactaggga catcgtagaa ccattcctgt tctttaccaa cctgagcaat  157860
aatcactgga gttttacaga accgcactcg gccttgttcg aacaattcag gccattgact  157920
aaagaaggct agcaatgatg gataaatcga acccgtacca tccacatcgg catcggtcat  157980
gatggcaata ttacgatagt tagttttctc tgcaggttca ccaataacca gtccagtgat  158040
tgcacagata tcaaatagtt ccttgttctt catgatatct gttgctgtca ttccccaggt  158100
attcataacc ttaccacgta atggataacc accttgaagg tctttattac gaacttcaat  158160
gaaaggaccc atagcggaat caccttcggt taggaacagg gttgtatctg catctttgcc  158220
gtataagtta gctttaatat gcttatggac cttggcttta gaagctttct tagcggcttt  158280
agtttcagct gccttttcag ctgctaattt acgtgctaaa gccgcttcaa cgataggcat  158340
aatcaaccct tcgtctttaa gaatatactg tgagattttc tttgcatcaa tttgaatatg  158400
gttacgaatt tcaccgaatg gtgacgtcaa acgttcttta gtctgggaat caaaacgcat  158460
attactcata tcgcgaatga acatcagcat agttaagcat tctttaactc gtgccttact  158520
tacttcgatg cctttatatt tcttcttgat gcctggcaag atgttcgc  agatatcatc  158580
aaacacacat tcaacatgat gaccaccatt cttagtatga atattgttca cataagttag  158640
gtgacggaat ccatccggag atgtagtaaa tgccattgag acattatcgg tttcttgaat  158700
tactacatct ttaccaaatt gattagcata ctttttaaag ttaccatcta cttttttacc  158760
```

```
attaaaagta aattggatac taggataaat tacagctaga gttttaagac gatctagagt    158820
aatatccaga taaatttgtg atagagagtt ctcttcaaaa tgattaaagt ctggagtgaa    158880
tataaccgaa gtacccttac ctttagattt cttagtagac caacctttgt tttccattcc    158940
attggaacag ttaactgtaa tttcattctc gccatcagag gtgatgcctg tgaacaaaac    159000
agagaagata ttagttaaac tactaccgac accattcatg ccgcctgtct tacgctcagc    159060
gtcatctcca aagttaccgc cagcctttgg aatagtccat gcagctacag gacctggaat    159120
ctgttcacca ttttggtcgg tgaccattgc ttgtggaata ccacgaccat tatcagaaac    159180
cgaaacctgg ttattcttaa tttgaacatc aatttattt  gcgaatttaa aattggtacg    159240
aatagcttca tcgacagagt tatcaatgat ttcgtcaatt aatttaacca gtccaggaac    159300
atagtttacc tgtgtaaaat taccaaacag gaatcgaccg tgggcttcat tagcactgga    159360
gccaatatac atcccactac gttttttgat atgttcaatg tcggacagta ctttaatttc    159420
attcttaatc atgttatttc ctcatgtagt aggagaatat tatcccattt cacttaaagc    159480
ataaaagggc cgaagcccct aatcaaatcg aatggtcgac tttttaaaga ataatccaga    159540
acaaacagtt ccttcaaccc ttttacccgt cggacccaca gcaataaagc ctgtacgttg    159600
gaaatcatct tcagaacagc caaataggtt atatcctgtg atttggattt gttcgtagcc    159660
atttgcatcc aatacacggg tagcattatc agcatcagta caaccgacca acgaaaccgc    159720
cagtaccagc gcggcaatag aactattaat gtatttcata atttctcact tagtcagcag    159780
gtcgtaaaaa ccgccattaa catgtttagg agccgagact aaccgaacag ccagccgatg    159840
gcagtcaggg caaacatcat tatctctttc agagattttc ttgattttt  cgtattcttt    159900
tgcacagtct tcagattggc atttgtaatc ataaagtggc attataagtc ccttccaga     159960
attcagtgcc ttcagcagtg atttcacgga acactgcata gataggggtt ttatcacctt    160020
gattttcgta tacataaacc gatgataaat gagaaaacgt atcagaatgt tccttttgaa    160080
ccacgattaa atctggggttg aacagaacat cttcaaattc ttcacgagtc gagttcatag    160140
taactttagc catttttattt tcctctcatt tgttgatagg gtaatcttat cactaccta     160200
ccatattgta tactgttttt ttaaacttta tgcaaaatga atatcagcat actcaacgat    160260
aaagctctca ggaacaacct taaaggttcc aaggaacacg atgttataga gcttaacgcc    160320
ttcttcaacc cactggtcgg tgatgtaacc ggacatacta gtggtttcat aagtcggacc    160380
gtacttgcac ttgtattcaa acggtttagg tgaaacgaaa aagacaccatt tacctaatt     160440
ccatttgaaa tcaacaccaa catgagattg gtcaatagtt tcaacgtctt gagctactac    160500
gccacggata tcattgcttt cacatacata cccatcatgg gattcaactt cttcaactac    160560
aggagcgatg tatccagtga attcagtcga ttccaagaat ttagcacgca cataagcgaa    160620
ttgagtttca gtctggccat ttttaggaat gatacgcact tttacttcag aattttctac    160680
actgacacct tctttaagtt ggatactaac aacttcaact aaacggcctg cagcttttga    160740
acgagacttt ttggatacac gaacgatacc gccgatatcg gaaatagtaa tcataatttt    160800
tctctcttgg ttaaaggttt attctccatg agagccatta aacatggct  ctcgataaag    160860
taaactatta attcaataca ttaaccactg cactacgagg tactacacta aaatcaccag    160920
catgtacaac gttcaggagc tcaacaccgt cttcaatcca ttggtctgtt acccaaccac    160980
agataggatt atcaaaagga cgacggatag acacagcagc acacaacagg tcggtagggc    161040
cttgttcttc aacttcttgg aacaggatga actcatcttc ataaaccagg gttttctcta    161100
ttttgttatt atctaaccgg cgaccgtgga tgacgtaaga tttagtaaac cagtcacttt    161160
```

```
tggcaaattc ttcaacaata aattcgcctt cgccaaaaac atcagtcaga gttttataac  161220
cagaaatcaa ggccttagtt ttaatttcag gttcaaccag tttgtaggtt ttgccgattt  161280
cgatagtctg agtagtcata ggtgattcct taatttccag tggtttaaca gggcatacat  161340
aagtgcttaa aacatcaaaa tcaatcagtt tagctgccgg attcggggta tatttagggt  161400
tataattaaa tttcatattg ttctcaattc aataaaatct acgagttcgg catgggattt  161460
gcggaacatt acttggcggc caccaatgac aacctcatct tctggtattt cgtaaacagc  161520
aaggtagaat cctttagaag ataattcttc acgctcttca cgagtgaacc agcgcatcat  161580
atcatactca ctggcaaaag caaaatggta gaggttaaca aaccaacctg gaatataatc  161640
gtcagagcct tcataatcag gccgtttcca cttagttcta atggctttat tagaattttc  161700
taccaacaac ttatcttgac ttggtagtgg aatatttta ttgacggtat gatggtgcct  161760
aaacttaggt ctgtcgaaac ctacttccaa taaccatcct tcactccatg agtccattgt  161820
acttctatat ggagtcattt gggtacagag gtctcgtcgt attgttatag catcttcaca  161880
atctaggata ctgaacgatg actccactcg ataaattttc attttgttct cctcatgttg  161940
atagggtaga taatatcatg tcatgaggag aagtaaacac ttttatcgat tttttatact  162000
taatgggtcg ggattctcag ggacatcttc caggcccaag gcgtatcgtt gggcatattt  162060
aagcatcaag atatccttag cacagtcatg gatggagtca tgagcaacaa agccgttcaa  162120
tgttccgtta ggcagaggac acatgctcaa tccacgagtc aatgaatatg cttcaatagc  162180
cgtacggatg tcacgttggt tccagaattt aaccggttct aatttgctgg tatcgatttc  162240
attctcaggg acaccttcag aacgataagc atcgcgaata aggtcgacta agataggaaa  162300
gtcaaaggac attccacggc accacatctg agatttccat tggtctactt cgttttacg  162360 gcagtattcc aggaaattac caaggccgat agaagtggtc acatcaattt cggacggcgc  162420
caggttttta cgtgcttcag gcccttgctc tttccaccac tgcaacgtgc ttttagaaaa  162480
cagtcgttta tcacgttgag aagcgaggtc aaatttaata cgaaggcctc gttgagtaag  162540
ctcttcaaac gtttctacaa cctctggatt ggggtcataa gcaattacag cgaggtcgat  162600
aaccgcggca ttttgggttg tggcaaaggt ttcaaagtca ataattatat cttcattta   162660 acgtacctca taaggtctcg gatttggccg acggtgtagt cttcaatata aaccgaagag  162720
atattgtcgt ccattagacg ctgtattgca ataaaatcgt attcaatctc tttaagagaa  162780
tgcaagacct tatgggcctt gccacggata ttggtatcgt cttggttgac cttaataata  162840
tattcagttt caaatttcaa cttataaaat tggtctttgg ttactttaat catattttcc  162900
tcaaacgtaa taagcgtcag tacgagcacg agtaatacta acataagcca gctgtgaagc  162960
taaactcaca tcagccatat gcatacacgc cgtatagatg aaactgttct ggactgtgag  163020
gccctgggat ttatgaacgg tgctcaccgg aagagctcga accttagtaa acattctctt  163080
agctttccaa aaatcggccc acttaggttt cttaccacta ccacgcatgg ctttgtattc  163140
agtagcaacc ttagccaaga aataatggaa cttctcgact gaagcctcat ctataacctt  163200
taagtgctct acgtaaatact catcatcttc atcgatagat tctacttgca ggtcccagta  163260
attaatcatt tgacgggtgc ctacatcctt agcagacaag aacaatgagg tgtggttcac  163320
atccagaata cgaaccattt gaccgttatt aaaaatggtt tcagagaatt tcttaccgtc  163380
gtattcaagt tccttcataa aaggctcttg catcaccagg atttcaccct tgatataagg  163440
tgcgtcggtt tcataaagct ttttacgaat aatgctattc agcttttcaa ccgatttatt  163500
```

```
tgtataagca aacatcctat tctcaaacag tgcatcagca tcctttacaa tggaaaaata  163560
attcatcata aaatctttta atgctgtttg agatttaaaa ccatggacac catgtccttc  163620
gaatacacaa tctctaaacc acccaccatt acggatttca gtagcaacct caatgatagg  163680
ggcattacta cgcattactt cggtcaaatg caattgcttg attttttggat gagtaaagaa  163740 cggagacaac tgcggactac catcacttcc aggttccact ggctgtagct gagctcggtc  163800
gccaatccct aatacagtac accatggagg cacggaagat tcgataatct taaacagctt  163860
accatcaatc atcgagcctt catcaacaac taacacatta catttgctca agtcaggagc  163920
ttcgcgttgt tcaaagatat cctggtcttc gtatgtagta gggttaatct ttagaattct  163980
gtggattgtt gatgcttctt gacctgcgag tttcgacaac acctttttgg ccgcatgggt  164040
aggtgcagtc aaaataactc cgagttcacc attcttgact agatggtcaa gaataaattt  164100
ggtaagggtt gttttacctg taccagcagg gccattcaat gtaatccatt cgcccttacg  164160
tcgtttaata gcttcaatga tttctttaaa agccgtcctc tggccgatgt tcaagtcttc  164220
aaatgtaatc atgccaattt tactcgctta acatataaag tgtctaaaac taatttaagt  164280
tctcgggctc gttcttcggt aggatacacg gttttagttt cccacttatc aaaccaccat  164340
tttctaggtg tgcacaccgt ttcaaggcgt ccaagccgaa gatatctttt tgtcgccatt  164400
tcataaacgg atagagcggt atcggctcca atctttgtcg aatacaaagt cacttcacca  164460
gcctcttcta atggaatttc gtacccgtct ttgtccttgt gaactaatac gtatgcatag  164520
tacatcacgt taacctctaa tcagtgaaaa aattgaagca ttcagcggaa gaccttttt  164580 caacttcatt ttgtcaataa aagaaaggtg ttctaaacgc tccagacctt ggataatttt  164640
atcatacata tcgtaacgcg tttctgcttc agacaattta aacttgacgc gccaatcagg  164700
cccaccaatt aaagatttaa gacccttttc catagtaccg attgaagcgt tagaaccatg  164760
gatacgagcc ttaaccgcga tgacagaagg ggtcttatca gtagctcctg atttaataag  164820
gtccttaaga cgttttttcac gcttttttaag gcctctttga gtatctttaa tattttttaac  164880 tattttacga attttataat aattatcggg ggttacttta aaactattag gcattttaga  164940
actacctgaa atacgaccg ctaaacgggt ttgtgcacgt ttcaattcat ctagagacaa  165000
atcggcacgt aagctattgt acttgacttt aactgggatt acattaccct caatatagcc  165060
gatatcatta ttaaaacgtt caaatgaaat cttatcacta actgaattct catcaaagct  165120
ctcgcctgaa taagcacaca cttttttgttc gagaagtcta cgaatgtact tactagacag  165180
gttaaagtcc ttaccacgtt tcttggcaga ggctttagtg tgttcgcgac gtttgtaaac  165240 cttaactca aattcagtag tcatgatatt tctcatctta cggacgattg gttgataggt  165300
ctatagtatc atgttgcccg ataaagtaaa caacttttt gctttaaatt ttcgacggta  165360
taatgaatca aggactttgt ctttcaatta aaccgggagg ttcagtaaga aagaacggaa  165420
agattccaaa tggtgtaatt attccattta ggatttctct caatagagtc tacgcgcagc  165480
gtagttcccg cagggaacat catctcatct tcatcattga ttaattgtaa gtttgctaca  165540
cgggtagatt caggaaatgc gcctgggaac tcttcagggg gcgcagcaca taacattta  165600 aagatttctt cctgataatt gtacacaaat ggtgcatcat taatacaaaa gatattaaat  165660
gtgccgtaga agttataaga cgcgaaattc cttgccacgt tgaagtcttt agagaagctc  165720
atcacgcggt cgaattcaat taccgcacct acacacattg tggactctag atacttcata  165780
gtctttttag atatgccacg atagagctta tcaggcacta cagaagtcag attcttacgg  165840 ataatttat tcagagtttc ctggatagta tctggtttat tttccataca ctgccagagc  165900
```

```
gtgctctgtt ctaaatcaga atacacctca tcaatttcta tctgagtatt ctcacggaaa  165960
tcatcgcatt tagcgttgtt gataaattct gctaatttat ggcttgggta taacatatta  166020
ttctcctcag ttgatataaa gatagtacca caagcctcct tgcctgtaaa ctaaaaatcc  166080
aacattttta aatgaattgt tttatactcg atttcgtacg ggtctctttt gacggtttcg  166140
attgcaacaa tctcaaatcg cgattggctg gagaccatga actcacattc ggtttcgacc  166200
atatcataga ggtcaatacg ggtttcatca atttcaaggt cgtctacatt acctgcaaga  166260
acaaggtcaa tagcatggtt gtagtagtca aaatgaatg gtgcattcct gagacttaaa  166320
atggttttgg ttccatattc ccatgcccct gcaaactgac gagcctgaga gtattgtgta  166380
ctaaaagaag taacgcgacc aggagaccat tgacaaccta ctgaaaggag ctctaattgc  166440
tcaagttctc tgggggtaat cccacgatac aactctactg gaaccgctga gtaacatgc  166500 ttgcgaacca gtttgtcgag gtcgtaatgg aagttagggt cctttttagc atccagacat  166560
ttctctaaca aggcttgttc agattttgaa aatttggaat tgattcggtc ttgataaaga  166620 cattttgtt cgatgttcat atgacctcca gtgatttaga ggtcattata acatgaaggg  166680
aggaggtgta aactacttaa acacaccaag tgggacgcca aacactgcaa tgtcagcagc  166740
catgcctaat gaggattggg tatatgaagt ataggagctt tttgattcat acgagctttt  166800
tgtttctggc ttctcggctt caatcttaag agctttcgcc tgaatatttt tttgctcggt  166860
ttccttacga gcctgtttac ggtcgatatc caacgccgat gtaggtatat tagtcagcca  166920
attcattatt ttacccaagg agcccatggt ggagggtcta agtaataaga agcaaggtca  166980
ctaaggacct ctttaggcaa cttaaaaccg tgcttctgta taatcatatc aagttcgttg  167040
acaaggtcaa caggcggctc ctgggttgtt tcaggctcag ggtccggaat gacaaacata  167100
tcaaataagt ccattagtag ccacctatag gaccgtactc gtacatacga gctcgcacct  167160
tagcatcacg aatagcgtct tcagtcatgg taaagcgcaa tccaatatca aagtgcttcc  167220
aaatctgacg ttcaacttca ataaggtctt cggtagcgga aataagataa gtacgacctt  167280
taagacgttc gttggacatt ctatcggtat ctttatagaa aatgtccatt gttccttcgc  167340
catacgggtc cggatggcga taaccttga tatgcaatgc ttcagccagg ctaaaaggac  167400
aatcttcagc aacatcaaca ttttttgttat ggtaagcctt catcataata ttttctggca  167460
gcttaatatc ttttaatcgt gtttctaact gggttataga attcgtacca ttatcgacaa  167520
ggataagaca cgctgtagca tcataaggtc gcgtttgtcc ggcagaatca cgaacaaaga  167580
attctagttc ataaactttc attatgtttt cctcttctta gtttacctac taaaggacca  167640
tccggaattt tattttcttg gatgtatttc tcgttttctt ccatcatttt actaccaatt  167700
ttaagaagca aatccagtgc ctctttagcg tgtttttcag cctcttcagt agtcatgatt  167760
tatccccata gatgtcacgc ataatcctaa gggcctcgcg ttctaatttc ttttcgcgtt  167820
cttcacggat acctttaaga atccattctt cggagtcacg tttcatttct gcattggctt  167880
ggtctaacca cccgtcatca agataatcac taggacggtc cagccaatct ttaagccatg  167940
ataaaggttt cattaatcac acgagctaga cgacgagtca cagcttcctg agtcataaga  168000
cgaataagaa gaatcaccag tccaagaact gacagcagcc gcaaccataa taggagtggt  168060
atcaatatgg cttgtgcgac gagcttctaa atgttctttt aacttttag atttcaaagg  168120 aagagcgccc gggcctacat taccagcttt ttcaggttga cgaataactt cttccatcat  168180
accatcgcct acataaacat attcccttaa cttaacgtct gatggactaa taggaaccgg  168240
```

```
cccttcgcca ggggtaatct tgaaaaaatt cttaagccaa caaatcataa gaaacctcgt  168300
ttaaattcaa ccttatcaat atcatcagtc tcgtgacgga tttcggcatt aaattcgata  168360
gaaccgtctt catgcatcat aaatgaatgg acaataactt cggtatacca aggagtataa  168420
aagtactttt tcaatacatg attagcgata atttcatcca aagttttatt tggtttaatc  168480
caacgattta acatagtgtt ctcctctata agataagacc atcttaacac aaccttccta  168540
aaaagtaaac ccttaagacc aaaaaaagga acccgaaggt tccttataat taaactactg  168600
gggtcggcgt gaacattgct gcgttcttag ttcgccaatc ggctgcatca gtcactacag  168660
tagtataggc tgcaacggcc gaagggaaag tctgataatg agagtctgca atacggtgct  168720
cgtttgaata aatctcaaac gggaccgaaa cctcagtacc tttaacttct ttaccttcac  168780
cagctggatg cgtaaaagtt ttgatattaa cgaaaccacc cataattaac tcctttgttg  168840
tttaattaca ggtgtattta ttacgcatat ttcttatcaa tataaaagtg tccaccgcct  168900
ttaacaaaga cccagaatag atttctatcg tctgtatccc gacaataaaa atcatctaac  168960
tggaaatagt tttcttcagg gaattcaaga tgccggccga gttctattgc atcagaacca  169020
aacgctttag tagcgggacg accatcatcg tcccatttct tgaaattgaa tttcattaat  169080
aaccacggtc ctgacgagca aagttctcag cgttttcag gtaatacaat ttaaagattt  169140
cttcagcagt cagaccgaga ccttggaaca tgttcagaac gaaatggaga atatcaatca  169200
tttcgaattt aatttcgagc tggtcttcag gagacaaatc gttaatcagg gtttcacgac  169260
gttcagcatg ttgagctttc caaggcttcc atactgcaga tgcatctttt tcgccattgc  169320
tcatgccacc aagagaagtc agaagttcac ggaattcatc atcaatataa tctttctgat  169380
tacgcaacca atcaacaact tcacctgcag tggccaaatc atcaggatga cggttatatt  169440
caggtttatc tttagccaaa cgggcctgta atgatttctg catatcaagc ataacctgca  169500
gagggtcttt atcttcgtga atcagagcat taaaataagc ttcctcagct ttatcaacac  169560
cagcaatcaa accactacat tcattaaaat gagccattat attttccttt ttcaattcat  169620
taataagtta gataattata acattaaaat ttataagcaa ttaggaagac cacccggtga  169680
atttgcgttg tcctgaatcc cagtgaacac ccacgtcagg agaataccta taattaaaat  169740
caccatagga ttctgaaatt tctaaaatat atcttacaaa atattcacaa agctcattag  169800
accatgaatc agaatacacc acgaagtgga aagatgattg gtcctcatca tcgacatcaa  169860
tccacacacg ttttaattta ccttccggcg aatcataaac acctgaaata tattcacctt  169920
taaccgaaag gctcccttct tcaaaagcgg tattcaaaac aagccctaat tctccagggc  169980
tagattcttc tacccaatca tcatgggtat tcaataaaat cttaatcata atatttcctt  170040
aaaaatcaaa tatgtctaat aacgaattgg tggtattaat atgaaccacc ggagctacat  170100
aatcatccat ccattctgga tatttacgcc cttcagatcg gtcattaggg tctaatgtat  170160
ttgcatatgc aaagttatat gaaattatat ctcgatgttc tttagtatca ccaacaatat  170220
ttaagatacg ttggcataaa aaatcatagt tatctttcat atactcaata caatatatat  170280
cttttaaagc ttgggttggt gatactccaa tttccaattt cttacggata atggcttcaa  170340
caagattacc atctccctgct gaaggttcaa agaatgtatt acccgcctta aaagattctt  170400
caccgcaaag ctttaaaaga atttttgtac agtaatcatt agtgaatacc tcatcagtag  170460
atttctggcg ttctcttgtt atttcaccgt ttttcttga ttcatcaatt gctaatttca  170520
tcaaggctca ccccattcac aacattttct gcatactgcc attctaaatc ggtaatgttg  170580
aagcgttctt gaatcatttc acgagtccat ttcttagtaa aatcgaccac aggagcattt  170640
```

```
tcaaccattt ttttgcctgc agtaccacca ccaagtccgg cataataagt gcatgctact 170700
ttaataggag gcatattata gaatgctata gcattttcag cttcttcaac agtatcaaac 170760
gaggcccaac attttttgta attacctgaa ttatccccac cgtgtggatg tgaattctcg 170820
attttggttg ctccgttcac aagaccgtta tagaaatcat tacccattat aattttagaa 170880
cctgctaaat gtactgataa tttacggttg aagtttacat aaaccggttt ttcaataccg 170940
ttataaccat ttaatttctc ttcagtgcga gttttatctg caatagattt tgcactaata 171000
ttgttaagaa ttaatgaaac aaactcatta ttcatatact cgtatttggc tttagagcac 171060
ccgttaacca aggtataact aggggattca tctttagtaa atttagccaa agccagatga 171120
gttcctacgt tagccgagaa atatttgtta tcacggttat cgtcaataat tgctattttc 171180
aaacgttttt tagcttcagg ccggtgagca ttgacaccca ttgtgtggag atatgaagcc 171240
ggggttatgg caataacgtt atcagcacaa gctaaggctt tatcaataaa tgctgtatca 171300
tattggaaag gcgggttcat aataattgta ttgaatttca ttttcttagg ggccttaatg 171360
aattcaaatc cagagaaaca tccgaaagta tcaaatacat aacgggcctt atctgaatca 171420
gttgaaatga ataagatatc ggaagtatca taaccgataa gagataataa tgaaactact 171480
tcaagggatt ctataacac                                              171499
```

BACTERIOPHAGE AND COMPOSITION COMPRISING SAME

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present invention relates to a novel bacteriophage having a specific ability to kill enterotoxigenic *Escherichia coli* (ETEC), a composition including the same, and a method for preventing or treating infectious diseases of animals using the novel bacteriophage or the composition.

BACKGROUND ART

*Escherichia coli* (hereinafter also referred to as *E. coli*) is a Gram-negative, short rod bacterium of genus *Escherichia*, family Enterobacteriaceae, and one of normal flora found in intestines of various animals including mammals. Most strains of *Escherichia coli* are non-pathogenic and can cause opportunistic infection, but some highly pathogenic strains cause various intestinal diseases and sepsis in animals including humans.

*Escherichia coli* can be classified into enterotoxigenic *Escherichia coli* (ETEC), enteropathogenic *Escherichia coli* (EPEC), enterohemorrhagic *Escherichia coli* (EHEC), enteroaggregative *Escherichia coli* (EAEC), enteroinvasive *Escherichia coli* (EIEC), necrotoxigenic *Escherichia coli* (NTEC), and the like, and, particularly, enterotoxigenic *Escherichia coli* is known to cause infectious disease in pigs.

Currently, with the trend toward large-scale group housing in pig farming, porcine colibacillosis has emerged as the most frequent and bothering disease in pig farms. Recently, outbreaks of porcine colibacillosis, which stunts piglet growth due to diarrhea and mortality, have been increasing in Korea, causing enormous economic loss to pig farmers.

For prevention and treatment of porcine colibacillosis, although various antibiotics have been applied to pigs in the related art, abuse or misuse of antibiotics can induce antibiotic resistance in pigs or can cause the antibiotics to remain in the pigs' body, leading to global restrictions on administration of antibiotics.

A bacteriophage refers to a bacterium specific virus that prevents and inhibits growth of a bacterium infected with a specific bacteriophage. As bacteriophages have stronger host specificity than antibiotics, and recent emergence of bacteria resistant to antibiotics is a growing problem, application of bacteriophages has drawn great interest.

Studies on bacteriophages have been actively performed in many countries, and there has been an increasing tendency to obtain approval from the Food and Drug Administration (FDA) for compositions using bacteriophages in addition to patent applications for bacteriophages.

However, bacteriophage related technologies for prevention and/or treatment of infectious diseases, which are important issues in the aviculture industry including poultry farming, due to enterotoxigenic *Escherichia coli* are still insufficient, and therefore there is a need for such bacteriophages and development of relevant technologies.

DISCLOSURE

Technical Problem

As a result of earnest investigation aimed at overcoming the emergence of bacteria resistant to antibiotics and residual antibiotics in animals and at effectively preventing and treating infectious diseases caused by *Escherichia coli*, the present inventors isolated a novel bacteriophage ΦCJ28 (KCCM11466P) having a specific ability to kill enterotoxigenic *Escherichia coli* from natural sources.

In addition, the present inventors identified morphological, biochemical, and genetic properties of the novel bacteriophage, confirmed that the bacteriophage has excellent acid resistance and heat resistance, and developed antibiotics, disinfectants, additives for feeds, and other compositions using the bacteriophage, a composition for preventing or treating infectious diseases caused by *Escherichia coli*, and a method for preventing or treating diseases using the same.

It is an object of the present invention to provide a novel bacteriophage ΦCJ28 (KCCM11466P) having a specific ability to kill enterotoxigenic *Escherichia coli*.

It is another object of the present invention to provide a composition for preventing and/or treating infectious diseases caused by enterotoxigenic *Escherichia coli*, including the bacteriophage ΦCJ28 (KCCM11466P) as an active ingredient.

It is a further object of the present invention to provide antibiotics, additives for feeds, additives for drinking water, feed, drinking water, disinfectants or detergents, including the bacteriophage ΦCJ28 (KCCM11466P) as an active ingredient.

It is yet another object of the present invention to provide a method for preventing and/or treating infectious diseases caused by enterotoxigenic *Escherichia coli* in non-human animals using the bacteriophage ΦCJ28 (KCCM11466P) or the composition including the bacteriophage ΦCJ28 (KCCM11466P) as an active ingredient.

Technical Solution

One aspect of the present invention provides a novel bacteriophage ΦCJ28 (KCCM11466P) having a specific ability to kill enterotoxigenic *Escherichia coli*.

Another aspect of the present invention provides a composition for preventing and/or treating infectious diseases caused by enterotoxigenic *Escherichia coli*, including the bacteriophage ΦCJ28 (KCCM11466P) as an active ingredient.

A further aspect of the present invention provides antibiotics, additives for feeds, additives for drinking water, feed, drinking water, disinfectants or detergents, including the bacteriophage ΦCJ28 (KCCM11466P) as an active ingredient.

Yet another aspect of the present invention provides a method for preventing and/or treating infectious diseases caused by enterotoxigenic *Escherichia coli*, including: administrating the bacteriophage ΦCJ28 (KCCM11466P) or the composition including the bacteriophage ΦCJ28 (KCCM11466P) as an active ingredient to a non-human animal.

Advantageous Effects

The bacteriophage ΦCJ28 (KCCM11466P) according to the present invention has an effect of having a specific ability to kill enterotoxigenic *Escherichia coli*.

Further, the bacteriophage ΦCJ28 (KCCM11466P) according to the present invention has excellent acid resistance and heat resistance, and thus can be employed not only as an agent for preventing or treating infectious diseases caused by enterotoxigenic *Escherichia coli* at various ranges of temperature and pH, but also as antibiotics, additives for feeds, additives for drinking water, feed, drinking water, disinfectants, detergents, and the like, including the bacteriophage ΦCJ28 (KCCM11466P) as an active ingredient.

Further, the present invention provides the bacteriophage ΦCJ28 (KCCM11466P) or antibiotics including the same as an active ingredient, and the antibiotics have effects in that the antibiotics have specificity for enterotoxigenic *Escherichia coli* as compared to prior antibiotics and thus selectively kill specific pathogenic bacteria; and that the antibiotics do not induce antibiotic resistance, resulting in extension of lifetime of products as compared to prior antibiotics.

Further, the present invention has effects of preventing or treating infectious diseases caused by enterotoxigenic *Escherichia coli* by administrating the bacteriophage ΦCJ28 (KCCM11466P) or the composition including the bacteriophage ΦCJ28 (KCCM11466P) as an active ingredient to a non-human animal.

DESCRIPTION OF DRAWINGS

FIG. 1 is an electron microscope image of a novel bacteriophage ΦCJ28 (KCCM1466P) (hereinafter referred to as 'ΦCJ28').

FIG. 2 shows results of pulsed field gel electrophoresis (PFGE) of a novel bacteriophage ΦCJ28.

FIG. 3 shows results of sodium dodecyl sulfate polyacrylamide gel electrophoresis (SDS-PAGE) of a novel bacteriophage ΦCJ28.

FIG. 4 is a graph depicting results of acid resistance experiment of a novel bacteriophage ΦCJ28.

FIG. 5 is a graph depicting results of heat resistance experiment of a novel bacteriophage ΦCJ28 at 60° C.

EMBODIMENTS

Hereinafter, embodiments of the present invention will be described in more detail. Description of details apparent to a person having ordinary knowledge in the art will be omitted herein.

One embodiment of the present invention provides a novel bacteriophage ΦCJ28 (KCCM11466P) (hereinafter referred to as 'ΦCJ28') having a specific ability to kill enterotoxigenic *Escherichia coli* (ETEC).

Enterotoxigenic *Escherichia coli* is a Gram-negative *bacillus* and an aerobic or facultative anaerobic bacterium which decomposes lactose and fructose to generate acids and gases. Enterotoxigenic *Escherichia coli* grows well on common media and is capable of growing at a temperature of about 7° C. to about 48° C. with ideal growth temperature ranging from about 35° C. to about 37° C. Further, enterotoxigenic *Escherichia coli* can grow at pH ranging from pH 4.5 to pH 9.

Since enterotoxigenic *Escherichia coli* produces enterotoxins similar to those produced from *Vibrio cholera*, a patient infected with enterotoxigenic *Escherichia coli* exhibits symptoms similar to a patient infected with *Vibrio cholera*. The produced enterotoxins can be broadly classified into heat-labile enterotoxin (LT) and heat-stable enterotoxin (ST). The heat-labile enterotoxin loses its activity when heated at about 60° C. for about 10 minutes, whereas the heat-stable enterotoxin does not lose its activity when heated at about 100° C. for about 30 minutes.

Enterotoxigenic *Escherichia coli* proliferates in an upper portion of the small intestine, and when the concentration of enterotoxigenic *Escherichia coli* approaches about $10^7$ colony forming units (cfu) to about $10^8$ cfu per unit volume (1 ml) of intestinal juices, enterotoxigenic *Escherichia coli* can cause infectious diseases including colibacillosis caused by *Escherichia coli*.

A bacteriophage is a bacteria-specific virus capable of infecting a specific bacterium and inhibiting growth of the bacterium, and is a virus including single or double-stranded deoxyribonucleic acid (DNA) or ribonucleic acid (RNA) as a genetic material.

Specifically, the bacteriophage ΦCJ28 according to the embodiment of the present invention is a bacteriophage that has species specificity of selectively infecting enterotoxigenic pathogenic *Escherichia coli* and morphologically belongs to Myoviridae having an icosahedral capsid structure with a contractile tail (see FIG. 1). Homology between a nucleotide sequence of the bacteriophage ΦCJ28 and decoded nucleotide sequences of other bacteriophages is compared and results are shown in Table 1. The bacteriophage ΦCJ28 shows stable acid resistance at pH 3.0 to pH 5.0 without losing activity (FIG. 4), and in terms of heat resistance, the bacteriophage ΦCJ28 shows activity decline of about 1 log or less when exposed to 60° C. for 30 minutes, and activity decline of about 3 log or more when exposed for 60 minutes or more at the same temperature (FIG. 5). DNA nucleotide sequence of the bacteriophage ΦCJ28 is set forth in SEQ ID NO: 1 of Sequence List.

The bacteriophage ΦCJ28 is a novel bacteriophage isolated by the present inventor, and was deposited at the Korean Culture Center of Microorganisms (KCCM) (361-221, Hongje 1-dong, Seodaemun-gu, Seoul, Korea) on Oct. 25, 2013 under accession number KCCM 11466P.

Another embodiment of the present invention provides a composition for preventing or treating infectious diseases caused by enterotoxigenic *Escherichia coli*, including the bacteriophage ΦCJ28 as an active ingredient.

Since the bacteriophage ΦCJ28 exhibits antibacterial activity capable of specifically killing enterotoxigenic *Escherichia coli*, the bacteriophage ΦCJ28 can be utilized in prevention or treatment of diseases caused by infection with enterotoxigenic *Escherichia coli*. Examples of infectious diseases caused by enterotoxigenic *Escherichia coli* to be prevented or treated using the bacteriophage ΦCJ28 include colibacillosis, specifically porcine colibacillosis, without being limited thereto.

Herein, the term "colibacillosis" refers to a disease occurring due to infection with a pathogenic *Escherichia coli* in animals, and symptoms thereof include sepsis, diarrhea (infant diarrhea and post weaning diarrhea), toxemia (edema and cerebrospinal angiopathy), and the like. Thereamong, sepsis is an acute systemic infection with high mortality which occurs mainly in infancy within two to three days after birth. Diarrhea is a gastrointestinal infection symptom frequently occurring during suckling within one week old to two weeks old and directly after weaning, which is a cause of mortality or stunted development. Toxemia mainly occurs after weaning in piglets at 8 week old to 12 week old and can frequently cause sudden death after exhibiting edema and neurological symptoms.

Herein, the term "preventing" or "prevention" refers to all actions to inhibit the diseases or delay occurrence of the diseases by administering the bacteriophage ΦCJ28 and/or the composition including the bacteriophage ΦCJ28 as an active ingredient to an animal.

Herein, the term "treating" or "treatment" refers to all actions to improve or ameliorate symptoms of infectious diseases by administering the bacteriophage ΦCJ28 and/or the composition including the bacteriophage ΦCJ28 as an active ingredient to an animal.

The composition for preventing or treating infectious diseases caused by enterotoxigenic *Escherichia coli* according to this embodiment may include the bacteriophage ΦCJ28 in amounts of $5\times10^2$ pfu/ml to $5\times10^{12}$ pfu/ml, specifically, $1\times10^6$ pfu/ml to $1\times10^{10}$ pfu/ml.

The composition for preventing or treating infectious diseases caused by enterotoxigenic *Escherichia coli* according to this embodiment may further include pharmaceutically acceptable carriers, and may be formulated with the carriers to provide foods, medicines, additives for feeds or additives for drinking water, and the like. Herein, the term "pharmaceutically acceptable carriers" refers to carriers or diluents that do not stimulate an organism and do not inhibit biological activity and properties of administered compounds.

Types of carriers applicable to this embodiment are not particularly limited and any pharmaceutically acceptable carriers commonly used in the art may be utilized. Examples of the carriers may include saline, distilled water, Ringer's solution, buffered saline, an albumin injection solution, a dextrose solution, a maltodextrin solution, glycerol, and ethanol, without being limited thereto. These may be used alone or in combination thereof.

Furthermore, as needed, other common additives such as antioxidants, buffered solutions and/or cytostatics may be added to the composition according to the present invention, and diluents, dispersants, surfactants, binders and/or lubricants may be further added to the composition according to the present invention to formulate injectable formulations such as aqueous solutions, suspensions and emulsions, pills, capsules, and granules.

Methods for administering the composition for preventing or treating infectious diseases caused by enterotoxigenic *Escherichia coli* according to this embodiment are not particularly limited, and any methods commonly used in the related art may be used. One example of the administration method may include oral administration or parenteral administration.

Examples of dosage forms for oral administration may include troches, lozenges, tablets, water soluble suspensions, oil-based suspensions, formulated powder, granules, emulsions, hard capsules, soft capsules, syrups, and elixirs.

In order to formulate the composition according to this embodiment into dosage forms such as tablets or capsules, binders such as lactose, saccharose, sorbitol, mannitol, starches, amylopectin, cellulose and gelatin; excipients such as dicalcium phosphate; disintegrators such as corn starch and sweet potato starch; lubricants such as magnesium stearate, calcium stearate, sodium stearyl fumarate and polyethylene glycol wax may be further included, and for capsule formulation, liquid carriers such as fatty oils may be further included in addition to the aforementioned substances.

Methods for parenterally administering the composition of this embodiment may include, for example, intravenous injection, intraperitoneal administration, intramuscular administration, subcutaneous administration, and topical administration, and a method of applying or spraying the composition according to the present invention to an affected region, without being limited thereto.

In order to formulate parenteral dosage forms, for example, the composition of this embodiment may be formulated into dosage forms for injection such as subcutaneous injection, intravenous injection and intramuscular injection; suppositories; or dosage forms for spraying such as aerosols so as to permit inhalation through inhalers, without being limited thereto. In order to formulate dosage forms for injection, the composition of this embodiment may be mixed with stabilizers or buffering agents in water to prepare solutions or suspensions, which are formulated into dosage forms for unit administration such as ampoules or vials. When the composition is formulated into dosage forms for spraying such as aerosols, the composition may be formulated with propellants and the like together with additives such that a concentrate dispersed in water or wetted powder is dispersed therein.

Suitable amounts of applying, spraying or administering the composition for preventing or treating infectious diseases caused by enterotoxigenic *Escherichia coli* according to this embodiment may differ according to factors such as age, body weight and sex of animals, degree of disease symptoms, ingested foods, rate of excretion, and the like in addition to a method for formulating the composition, an administration method, administration time and/or routes for administration, and a generally skilled veterinarian can easily determine and prescribe dose amounts effective for intended treatment.

A further embodiment of the present invention provides antibiotics including the bacteriophage ΦCJ28 as an active ingredient.

Herein, the term "antibiotics" refers to a preparation that is administered to animals including humans in medicine form and exhibits efficacy of sterilizing bacteria, and is used as a general term for antiseptics, germicides and antibacterial agents.

Antibiotics of this embodiment including the bacteriophage ΦCJ28 as an active ingredient have effects in that the antibiotics have specificity for enterotoxigenic *Escherichia coli* as compared to typical antibiotics and thus kill specific pathogenic bacteria, but not beneficial bacteria; and in that the antibiotics do not induce antibiotic resistance, causing extension of lifetime of products as compared to typical antibiotics.

Yet another embodiment of the present invention provides an additive for feeds or drinking water, which includes the bacteriophage ΦCJ28 as an active ingredient.

The additives for feeds or the additives for drinking water may be used by separately preparing additives for feeds or additives for drinking water using the bacteriophage ΦCJ28 or the composition including the same and mixing feed or drinking water with the additives, or directly adding the bacteriophage ΦCJ28 or the composition including the same in a process of preparing feed or drinking water.

The bacteriophage ΦCJ28 or the composition including the bacteriophage ΦCJ28 as an active ingredient used in the form of additives for feeds or additives for drinking water according to this embodiment may be a liquid form or a dried form, for example, a dried powder form.

For example, the bacteriophage ΦCJ28 according to the present invention is mixed in powder form in amounts of 0.05% by weight (wt %) to 10 wt %, specifically 0.1 wt % to 2 wt %, based on the weight of additives for feeds.

Methods for drying the additives for feeds or additives for drinking water according to this embodiment to yield dried powder are not particularly limited, and any methods commonly used in the related art may be utilized. Examples of the drying method may include air drying, natural drying, spray drying, and lyophilization, without being limited thereto. These methods may be used alone or in combination thereof.

The additives for feeds or additives for drinking water according to this embodiment may further include other non-pathogenic microorganisms. The microorganisms may be selected from the group consisting of *Bacillus* sp. such as *Bacillus subtilis* capable of producing proteases, lipases and/or glycosyltransferases; lactic acid bacteria such as *Lactobacillus* sp. having physiological activity and organic material decomposing capability under anaerobic conditions like the stomach of cattle; filamentous bacteria such as *Aspergillus oryzae* having effects of weight gain in animals, increase in milk production, and increase of digestion-absorption rate of feed; and yeasts such as *Saccharomyces cerevisiae* and the like. These microorganisms may be used alone or in combination thereof.

The additives for feeds or additives for drinking water according to this embodiment including the bacteriophage ΦCJ28 as an active ingredient may further include other additives as needed. Examples of usable additives may include binders, emulsifiers, and preservatives added for prevention of quality deterioration of feed or drinking water; amino acid, vitamin, enzyme, probiotics, flavoring agents, non-protein nitrogen compounds, silicate, buffering agents, coloring agents, extracting agents or oligosaccharides that are added in order to increase utility of feed or drinking water; and other supplements to feed, and the like. These additives may be used alone or in combination thereof.

The additives for feeds according to the present invention may be present in amounts of 0.05 parts by weight to 10 parts by weight, specifically 0.1 parts by weight to 2 parts by weight, based on 100 parts by weight of feed. The additives for drinking water according to the present invention may be present in amounts of 0.0001 parts by weight to 0.01 parts by weight, specifically 0.001 parts by weight to 0.005 parts by weight, based on 100 parts by weight of drinking water. Within these ranges, the additives allow activity of the bacteriophage ΦCJ28 against enterotoxigenic *Escherichia coli* to be sufficiently displayed.

Yet another embodiment of the present invention provides feeds or drinking water prepared by adding the additives for feeds or the additives for drinking water including the bacteriophage ΦCJ28 as an active ingredient to feeds or drinking water, or directly adding the bacteriophage ΦCJ28 thereto.

Feeds used in this embodiment are not particularly limited, and any feeds commonly used in the related art may be used. Examples of the feeds may include vegetable feeds such as grains, root vegetables, food processing byproducts, algae, fibers, pharmaceutical byproducts, oils and fats, starches, residues or byproducts of grain, and the like; and animal feeds such as proteins, inorganic substances, oils and fats, minerals, single cell proteins, and animal planktons or foods. These feeds are used alone or in combination thereof.

Drinking water used in this embodiment is not particularly limited, and any drinking water commonly used in the related art may be used.

Yet another embodiment of the present invention provides disinfectants or detergents including the bacteriophage ΦCJ28 as an active ingredient. Dosage forms of the disinfectants or detergents are not particularly limited, and any dosage forms commonly used in the related art may be used.

In order to remove enterotoxigenic *Escherichia coli*, the disinfectants may be sprayed to habitats of animals, slaughterhouses, dead regions, kitchens, and cooking equipment, without being limited thereto.

The detergents may be used to wash a surface of the dermis or body parts of animals that are exposed to or can be exposed to enterotoxigenic *Escherichia coli*, without being limited thereto.

Yet another embodiment of the present invention provides a method for preventing and/or treating infectious diseases caused by enterotoxigenic *Escherichia coli* using the bacteriophage ΦCJ28 or the composition including the bacteriophage ΦCJ28 as an active ingredient.

Specifically, the prevention method or treatment method of this embodiment includes administering a pharmaceutically effective amount of the bacteriophage ΦCJ28 or the composition including the bacteriophage ΦCJ28 as an active ingredient to a non-human subject that is exposed to or can be exposed to enterotoxigenic *Escherichia coli*. Suitable total amounts of the bacteriophage ΦCJ28 or the composition including the same per day may be determined by a physician within proper medicinal judgment, as apparent to those skilled in the art.

A concrete pharmaceutically effective amount of the bacteriophage ΦCJ28 or the composition including the bacteriophage ΦCJ28 as an active ingredient may be determined by taking into account the sorts and degree of reaction to achieve, age, body weight, general health condition, sex or diet of corresponding individuals, administration time and administration routes of bacteriophage ΦCJ28 or a composition including the same, and secretion rate of the composition, treatment period, and the like, and may differ depending upon various factors and similar factors well known in the field of medicine including ingredients of medicines that are used simultaneously or at different times.

The bacteriophage ΦCJ28 or the composition including the bacteriophage ΦCJ28 as an active ingredient may be administered in the form of a pharmaceutical preparation to an animal by intranasal spraying, or directly added to feeds or drinking water for animals so as to be digested, and may be mixed in the form of additives for feeds or additives for drinking water with feeds or drinking water and then administered to an animal.

Routes and methods for administration of the bacteriophage ΦCJ28 or the composition including the bacteriophage ΦCJ28 as an active ingredient are not particularly limited, and the administration may be realized by any routes and methods so long as the administration allows the bacteriophage ΦCJ28 or the composition including the same to reach desired tissues. Namely, the bacteriophage ΦCJ28 or the composition including the bacteriophage ΦCJ28 as an active ingredient may be administered by various oral or parenteral routes, and examples of administration may include oral, rectal, topical, intravenous, intraperitoneal, intramuscular, intra-arterial, trans-dermal, intranasal, and inhalation, without being limited thereto.

Hereinafter, the present invention will be described in more detail with reference to a preferred example. It should be understood that these examples are not to be construed in any way as limiting the present invention.

[Example 1]—Isolation of Bacteriophage that Infects Enterotoxigenic *Escherichia coli*

Example 1-1

Bacteriophage Screening and Single Bacteriophage Isolation 50 ml of a specimen obtained from pig feces collected around Samwhawonjong farm in Gwangcheon, Hongsung-gun, Chungcheong Province and environmental samples was centrifuged at 4,000 rpm for 10 minutes, and the resulting supernatant was filtered through a 0.45 μm filter to prepare a specimen liquid, which in turn was used to perform a soft agar overlay method. The soft agar overlay method refers to a method of observing bacteriophage lysis using a host cell growing on top-agar (attached to a solid medium using 0.7% agar).

Specifically, 150 μl of a shaking culture solution ($OD_{600}$=2) of enterotoxigenic *Escherichia coli* (2618) separated by veterinary infectious disease laboratory of the Department of Veterinary Medicine, Seoul National University and 2 ml of 10×LB medium (10 g/l of tryptophan; 5 g/l of yeast extract; 10 g/l of NaCl) were mixed with 18 ml of the filtered specimen liquid, followed by culturing at 30° C. for 18 hours, and the resulting cultured solution was centrifuged at 4,000 rpm for 10 minutes, and the resulting supernatant was filtered through a 0.45 μm filter. Subsequently, a mixed solution consisting of 3 ml of 0.7% (w/v) agar and 150 μl of a shaking culture solution ($OD_{600}$=2) of enterotoxigenic *Escherichia coli* (2618) was poured and solidified on an LB medium plate, to which 10 μl of the specimen liquid was added dropwise, followed by culturing at 30° C. for 18 hours, thereby identifying formation of plaques.

Since it is known that one sort of bacteriophage is present per plaque, the inventors tried to isolate single bacteriophages from the formed plaques. Specifically, 400 μl of SM solution (5.8 g/l of NaCl; 2 g/l of $MgSO_4 7H_2O$; 50 ml of 1M Tris-HCl (pH 7.5)) was added to the plaques and left at room temperature for 4 hours, thereby obtaining a bacteriophage solution. Subsequently, 100 μl of the bacteriophage solution was mixed with 5 ml of 0.7% (w/v) agar and 150 μl of a shaking culture solution ($OD_{600}$=2) of enterotoxigenic *Escherichia coli* (2618), which was used to perform a soft agar overlay method using an LB medium plate having a diameter of 150 mm wherein cultivation was performed until the bacteriophage was completely lysed. After completion of cultivation, 5 ml of SM solution was added to the LB medium plate and left at room temperature for 4 hours, thereby obtaining a bacteriophage solution.

To the obtained solution, 1% (v/v) chloroform was added and mixed for 10 minutes, followed by centrifugation at 4,000 rpm for 10 minutes, thereby obtaining a supernatant, which in turn was filtered through a 0.45 μm filter, thereby obtaining a final specimen.

Example 1-2

Large Scale Culture and Purification of Bacteriophage

Bacteriophage obtained in Example 1-1 was cultured at large scale using enterotoxigenic *Escherichia coli* (2618), and then the bacteriophage was purified therefrom.

Specifically, enterotoxigenic *Escherichia coli* (2618) was shaking cultured, and inoculated at $1.0 \times 10^{10}$ cfu, followed by centrifuging at 4,000 rpm for 10 minutes and re-suspending in 4 ml of SM solution. To this solution, the bacteriophage was added at $1.0 \times 10^7$ pfu with multiplicity of infection (MOI) of 0.001, and then left at room temperature for 20 minutes. 150 ml of LB medium was inoculated therewith, and cultured at 30° C. for 5 hours.

After completion of cultivation, chloroform was added to a volume of 1% (v/v) of the final volume, followed by stirring for 20 minutes, to which DNase I and RNase A as restriction enzymes were added in a final concentration of 1 μg/ml, respectively, and left at 30° C. for 30 minutes. Subsequently, sodium chloride and polyethylene glycol were added to a final concentration of 1M and 10% (w/v), respectively, and left at 4° C. for 3 hours, followed by centrifuging at 4° C. and 12,000 rpm for 20 minutes, thereby obtaining a precipitate.

The obtained precipitate was suspended in 5 ml of SM solution and then left at room temperature for 20 minutes, 1 ml of chloroform was added thereto with stirring, followed by centrifugation at 4° C. with 4,000 rpm for 20 minutes, thereby obtaining a supernatant. The supernatant was filtered through a 0.45 μm filter, followed by ultracentrifugation (35,000 rpm, 1 hour, 4° C.) using a glycerol density gradient method (density: 40%, 5% glycerol), thereby purifying a bacteriophage.

The present inventors isolated a bacteriophage having a specific ability to kill enterotoxigenic *Escherichia coli* from samples collected from pig feces, which was designated as "Bacteriophage ΦCJ28" and deposited at the Korean Culture Center of Microorganisms (KCCM) (361-221 Hongje 1-dong, Seodaemun-gu, Seoul, Korea) on Oct. 25, 2013 under accession number KCCM11466P.

Example 2

Morphology Examination of ΦCJ28

The bacteriophage ΦCJ28 purified in Example 1 was diluted in 0.01% gelatin solution, and then fixed with a 2.5% glutaraldehyde solution. The resulting bacteriophage was added dropwise to a carbon-coated mica plate (ca. 2.5 mm×2.5 mm), acclimated for 10 minutes, and then washed with distilled water. The carbon film was mounted on a copper grid, and stained with 2% uranyl acetate for 60 seconds, dried, and examined under a transmission electron microscope (JEM-1011, 80 kV, magnification of ×200,000) (FIG. 1).

FIG. 1 is a transmission electron microscope image of bacteriophage ΦCJ28, in which the bacteriophage ΦCJ28 had morphological characteristics of an icosahedral capsid with a contractile tail, indicating that the bacteriophage belongs to family Myoviridae.

Example 3

Total Genomic DNA Size Analysis of ΦCJ28

Genomic DNA was extracted from the bacteriophage ΦCJ28 purified in Example 1.

Specifically, to a cultured solution of the purified bacteriophage ΦCJ28, 20 mM ethylenediaminetetraacetic acid (EDTA), 50 μg/ml protease K and 0.5% (w/v) sodium dodecyl sulfate (SDS) were added and left at 50° C. for one hour, to which an equal amount of phenol (pH 8.0) was added with stirring, followed by centrifugation at room temperature and 12,000 rpm for 10 minutes, thereby obtaining a supernatant.

The supernatant was mixed with an equal amount of PC (phenol:chloroform=1:1), followed by centrifugation at room temperature and 12,000 rpm for 10 minutes, thereby obtaining a supernatant. The supernatant was mixed with an equal amount of chloroform, followed by centrifugation at room temperature and 12,000 rpm for 10 minutes, thereby obtaining a supernatant. The supernatant was mixed with 10% (v/v) of 3M sodium acetate based on the total volume, followed by the addition of 2 volumes of 95% cold ethanol, mixing, and standing at −20° C. for 1 hour. The resulting substance was centrifuged at 0° C. and 12,000 rpm for 10 minutes, from which a supernatant was removed to obtain a precipitate, which was dissolved in 50 μl of TE buffered solution (Tris-EDTA, pH 8.0). The extracted DNA was diluted 10 fold, and then concentration of DNA was determined by measuring absorbance at $OD_{260}$.

Next, 1 μg of DNA was loaded on a 1% PFGE (pulsed field gel electrophoresis) agarose gel, and developed using BIORAD PFGE SYSTEM NO. 7 PROGRAM (size ranging from 25 kb to 100 kb; switch time ramp 0.4 seconds to 2.0 seconds, linear shape; forward voltage, 180 V; reverse voltage, 120 V) at room temperature for 20 hours (FIG. 2).

FIG. 2 is an electrophoresis gel photograph of genomic DNA of the bacteriophage ΦCJ28, and it could be seen that the genomic DNA size of the bacteriophage ΦCJ28 was 98 kb or more. In FIG. 2, M corresponds to DNA ladder as a standard for size measurement.

Example 4

Protein Pattern Analysis of CJ28

15 μl of purified bacteriophage ΦCJ28 solution ($10^{10}$ pfu/ml titer) was mixed with 3 μl of 5×SDS sample solution, and then boiled for 5 minutes to perform 12% SDS-PAGE (FIG. 3).

FIG. 3 is an electrophoresis photograph of SDS-PAGE results performed on the bacteriophage ΦCJ28, and it could be seen that main proteins had a size of about 67.9 kDa, about 50.8 kDa and about 6 kDa.

Example 5

Analysis of Genetic Properties of ΦCJ28

In order to determine genetic properties of the bacteriophage ΦCJ28 purified in Example 1, DNA of the bacteriophage ΦCJ28 was analyzed using an FLX Titanium Sequencer (Roche) as a gene analyzer. Genes were recombined using GS and de novo assembler software (Roche) by Macrogen Inc. Open reading frame was identified using GeneMark.hmm, Glimmer v3.02 and FGENESB software. Open reading frame was annotated using BLASTP and InterProScan.

Nucleotide sequence of the bacteriophage ΦCJ28 showed similarity to nucleotide sequence of previously reported bacteriophage (Enterobacteria phage Bp7), but it could be seen that there were no bacteriophages in which all fragments 100% coincide. Accordingly, it could be seen that the bacteriophage was a novel isolated bacteriophage.

The following Table 1 shows comparison results between nucleotide sequence of the bacteriophage ΦCJ28 and decoded nucleotide sequence of the prior reported bacteriophage in the art.

TABLE 1

| | Query | | | Subject | | Identities | |
|---|---|---|---|---|---|---|---|
| Name | Length | Start | End | Description | E-Value | Match/Total | Pct. (%) |
| SEQ ID NO: 1 | 171499 | 94429 | 108404 | Enterobacteria phage Bp7, complete Genome | 0 | 13319/14021 | 94 |

DNA of the prepared bacteriophage CJ28 was analyzed using a DNA sequencer and total nucleotide sequence is set forth in SEQ ID NO: 1.

Example 6 pH Stability of ΦCJ28

In order to identify whether the bacteriophage ΦCJ28 can maintain stability at low pH like stomach conditions, stability of the bacteriophage ΦCJ28 was examined at various pH (pH 2.0, 3.0, 4.0, 5.0).

For the experiment, various pH solutions (sodium acetate buffer solutions (pH 4.0 and pH 5.0) and sodium citrate buffer solutions (pH 2.0 and pH 3.0)) were prepared at a concentration of 2M.

180 μl of each pH solution was mixed with 20 μl of a bacteriophage solution with $2.9 \times 10^9$ PFU/ml titer to allow each pH solution to have a concentration of 1M, and then the resulting solution was left at room temperature for 2 hours. For a control group, 20 μl of a bacteriophage solution with $2.9 \times 10^9$ PFU/ml titer was mixed with 180 μl of SM solution by the same method, and the resulting solution was left at room temperature for 2 hours. Thereafter, the solutions were serially diluted, and 10 μl of each of solutions in each dilution step was cultured by the soft agar overlay method at 30° C. for 18 hours to determine bacteriophage titer based on whether the bacteriophage was lysed (FIG. 4).

FIG. 4 shows experimental results of acid resistance of the bacteriophage CJ28. In FIG. 4, it could be seen that the bacteriophage CJ28 did not lose its activity and maintained stability from pH 3.0 to pH 5.0, as compared with the control group.

Example 7

Heat Stability of Bacteriophage ΦCJ28

If bacteriophages are formulated into additives for feeds among dosage forms of bacteriophages, heat can be generated during formulation procedures, and thus, the following experiment was performed in order to determine heat stability of bacteriophages.

Specifically, 200 μl of bacteriophage ΦCJ28 solution with $2.9 \times 10$ PFU/ml was left at 60° C. for 0 minute, 30 minutes, 60 minutes and 120 minutes, respectively. Thereafter, the resulting experimental culture solution was serially diluted, and 10 μl of each of solutions in each dilution step was cultured by the soft agar overlay method at 30° C. for 18 hours to determine bacteriophage titer based on whether the bacteriophage was lysed (FIG. 5).

FIG. 5 shows experimental results of heat resistance of bacteriophage ΦCJ28. As shown in FIG. 5, it could be seen that bacteriophage ΦCJ28 showed activity loss of about 1 log or less until bacteriophage ΦCJ28 was exposed to 60° C. for 30 minutes and activity loss of 3 log or more when bacteriophage ΦCJ28 was exposed for 60 minutes or more.

Example 8

Examination of Infection Range of Bacteriophage ΦCJ28 on a Wild-Type Isolated Strain, Enterotoxigenic *Escherichia coli*

Lytic activity of bacteriophage ΦCJ28 was tested for 99 strains of the wild-type enterotoxigenic *Escherichia coli* isolated by College of Veterinary Medicine, Seoul National University (SNU), College of Veterinary Medicine, Konkuk University and Korea Animal and Plant Quarantine Agency (KAPQA), in addition to enterotoxigenic *Escherichia coli* (2618) used in the present experiment. The isolated strains consist of 37 strains of F-serotype F4 type, 30 strains of F5 type, 7 strains of F6 type, 20 strains of F18 type and 5 strains of other type.

Specifically, 150 μl of a shaking culture solution of each strain ($OD_{600}$=2) was mixed, and 10 μl of bacteriophage ΦCJ28 solution with $10^9$ pfu/ml titer was dropped thereto and cultured by the soft agar overlay method at 30° C. for 18 hours, and then plaque formation was examined.

The results are shown in Table 2.

TABLE 2

| No. | Type | Strains | ΦCJ28 | No. | Type | Host cell | ΦCJ28 |
|---|---|---|---|---|---|---|---|
| 1 | F4 | 345 |   | 51 | F5 | UK21 |   |
| 2 |   | 105 | 0 | 52 |   | UK23 |   |
| 3 |   | 122 | 0 | 53 |   | UK24 |   |
| 4 |   | 0149 |   | 54 |   | UK25 |   |
| 5 |   | JG280 |   | 55 |   | UK26 |   |
| 6 |   | F4 | 0 | 56 |   | 1-1 |   |
| 7 |   | 162 | 0 | 57 |   | 6-1 |   |
| 8 |   | 160 | 0 | 58 |   | 9 |   |
| 9 |   | 107 |   | 59 |   | 10 | 0 |
| 10 |   | R08 |   | 60 |   | 14 | 0 |
| 11 |   | 193 |   | 61 |   | 16 | 0 |
| 12 |   | 271 |   | 62 |   | 17 | 0 |
| 13 |   | 3220 | 0 | 63 |   | 30 |   |
| 14 |   | UK1 |   | 64 |   | 31 |   |
| 15 |   | UK3 |   | 65 |   | 34 | 0 |
| 16 |   | UK4 |   | 66 |   | 35 | 0 |
| 17 |   | UK7 | 0 | 67 |   | 21 |   |
| 18 |   | UK8 |   | 68 | F6 | 23 |   |
| 19 |   | UK9 | 0 | 69 |   | F6 | 0 |
| 20 |   | UK11 |   | 70 |   | 626 | 0 |
| 21 |   | UK14 |   | 71 |   | P87 (SNU) | 0 |
| 22 |   | UK15 |   | 72 |   | S127 |   |
| 23 |   | UK16 |   | 73 |   | 132 |   |
| 24 |   | UK17 |   | 74 |   | 133 |   |
| 25 |   | UK18 |   | 75 | F18 | 135 | 0 |
| 26 |   | UK19 |   | 76 |   | UK5 |   |
| 27 |   | UK20 |   | 77 |   | UK6 |   |
| 28 |   | 0105 |   | 78 |   | UK10 |   |
| 29 |   | UK24 |   | 79 |   | UK12 | 0 |
| 30 |   | UK25 |   | 80 |   | UK13 | 0 |
| 31 |   | UK26 |   | 81 |   | UK22 |   |
| 32 |   | UK29 |   | 82 |   | UK27 |   |
| 33 |   | UK30 |   | 83 |   | E2-4 |   |
| 34 |   | UK31 |   | 84 |   | 5 | 0 |
| 35 |   | 66-1 |   | 85 |   | 8 | 0 |
| 36 |   | K43 (KAPQA) |   | 86 |   | 11 | 0 |
| 37 |   | K45 (KAPQA) |   | 87 |   | 12 | 0 |
| 38 | F5 | 2618 | 0 | 88 |   | 23 | 0 |
| 39 |   | 2617 |   | 89 |   | 24 | 0 |
| 40 |   | 1 | 0 | 90 |   | 25 | 0 |
| 41 |   | 2 | 0 | 91 |   | 28 | 0 |
| 42 |   | 3 | 0 | 92 |   | 31 | 0 |
| 43 |   | 4 | 0 | 93 |   | 35 | 0 |
| 44 |   | 5 | 0 | 94 |   | 42 | 0 |
| 45 |   | 6 |   | 95 |   | 49 | 0 |
| 46 |   | F5041 |   | 96 | Other | UK32 |   |
| 47 |   | 645 |   | 97 |   | UK33 |   |
| 48 |   | K99 (KAPQA) |   | 98 |   | UK34 |   |
| 49 |   | S192 (SNU) |   | 99 |   | UK35 | 0 |
| 50 |   | UK2 | 0 | 100 |   | UK36 |   |

As shown in table 2, the bacteriophage ΦCJ28 exhibits infection ability to F-serotype F4, F5, F6, F18 types, which are major causative bacteria of pig diarrhea in general pig farms, and thus is anticipated to exhibit excellent efficacy.

The invention claimed is:

1. A composition comprising bacteriophage CJ28 deposited under accession number KCCM11466P and a binder selected from the group consisting of lactose, saccharose, sorbitol, mannitol, starch, amylopectin, cellulose, and gelatin, wherein the composition is in a dried state, wherein the bacteriophage ΦCJ28 is present in the composition in an amount of from $5 \times 10^{12}$ pfu/ml to $5 \times 10^{12}$ pfu/ml, and the binder is present in the composition in an amount of from 0.05 parts by weight to 10 parts by weight.

2. The composition according to claim 1, further comprising a pharmaceutically acceptable carrier.

3. The composition according to claim 1, wherein the dried state is a dried powder state.

4. The composition according to claim 1, wherein the composition is formulated into a form selected from a group consisting of pills, capsules, granules, and tablets.

5. The composition according to claim 1, wherein the composition is an additive for an animal feed or animal drinking water.

* * * * *

UNITED STATES PATENT AND TRADEMARK OFFICE
CERTIFICATE OF CORRECTION

PATENT NO. : 11,785,948 B2
APPLICATION NO. : 16/803710
DATED : October 17, 2023
INVENTOR(S) : Eun Mi Shin It is certified that error appears in the above-identified patent and that said Letters Patent is hereby corrected as shown below:

On the Title Page

Column 2, Line 27, item [56] Delete ""nterotoxigenic" and insert -- enterotoxigenic --.

Column 2, Line 5, item [56] Delete "enterotoxic" and insert -- enterotoxigenic --.

Page 2, Column 1, Line 2, item [56] Delete ":;haracteristics," and insert -- characteristics, --.

Page 2, Column 1, Line 14, item [56] Delete "{ETEC)" and insert -- (ETEC) --.

Page 2, Column 2, Line 3, item [56] Delete "{EHEC and STEC)" and insert -- (EHEC and STEC) --.

In the Specification

Column 3, Line 29, Delete "(KCCM1466P)" and insert -- (KCCM11466P) --.

Column 8, Lines 66-67, Delete "Hongsung-gun," and insert -- Hongseong-gun, --.

Column 11, Line 15, Delete "CJ28" and insert -- ΦCJ28 --.

Column 11, Line 56, Delete "CJ28" and insert -- ΦCJ28 --.

Column 12, Line 19, Delete "CJ28." and insert -- ΦCJ28. --.

Column 12, Line 20, Delete "CJ28" and insert -- ΦCJ28 --.

Column 12, Line 33, Delete "2.9×10" and insert -- $2.9 \times 10^8$ --.

Signed and Sealed this
Twenty-seventh Day of February, 2024

Katherine Kelly Vidal
*Director of the United States Patent and Trademark Office*

CERTIFICATE OF CORRECTION (continued)
U.S. Pat. No. 11,785,948 B2

In the Claims

Column 159, Line 31, Claim 1, delete "CJ28" and insert -- ΦCJ28 --.

Column 159, Line 37, Claim 1, after "from" delete "$5\times10^{12}$" and insert -- $5\times10^2$ --.